(12) United States Patent
Bent et al.

(10) Patent No.: US 10,995,342 B2
(45) Date of Patent: May 4, 2021

(54) RHG1 MEDIATED RESISTANCE TO SOYBEAN CYST NEMATODE

(71) Applicants: Wisconsin Alumni Research Foundation, Madison, WI (US); The Board of Trustees of the University of Illinois, Urbana, IL (US)

(72) Inventors: Andrew Bent, Madison, WI (US); Matthew Hudson, Urbana, IL (US); Brian Diers, Urbana, IL (US); Sara Melito, Sassari (IT); David Cook, Madison, WI (US); Teresa Hughes, Lafayette, IN (US); Adam Bayless, Madison, WI (US); Jianping Wang, Gainesville, FL (US); Tong Geon Lee, Champaign, IL (US); Xiaoli Guo, Madison, WI (US)

(73) Assignees: WISCONSIN ALUMNI RESEARCH FOUNDATION, Madison, WI (US); THE BOARD OF TRUSTEES OF THE UNIVERSITY OF ILLNOIS, Urbana, IL (US)

( * ) Notice: Subject to any disclaimer, the term of this patent is extended or adjusted under 35 U.S.C. 154(b) by 0 days.

(21) Appl. No.: 13/843,447

(22) Filed: Mar. 15, 2013

(65) Prior Publication Data
US 2013/0305410 A1 Nov. 14, 2013

Related U.S. Application Data

(60) Provisional application No. 61/676,854, filed on Jul. 27, 2012, provisional application No. 61/646,017, filed on May 11, 2012.

(51) Int. Cl.
*C12N 15/82* (2006.01)
*C07K 14/415* (2006.01)

(52) U.S. Cl.
CPC ........ *C12N 15/8285* (2013.01); *C07K 14/415* (2013.01); *Y02A 40/146* (2018.01)

(58) Field of Classification Search
CPC .................................................. C12N 15/8285
See application file for complete search history.

(56) References Cited

U.S. PATENT DOCUMENTS

| | | | | |
|---|---|---|---|---|
| 7,154,021 B2* | 12/2006 | Hauge | ............. | C07K 14/415 800/265 |
| 7,767,882 B2 | 8/2010 | Lu et al. | | |
| 8,692,064 B2* | 4/2014 | Nguyen | ............. | A01H 1/00 800/260 |
| 2002/0144310 A1 | 10/2002 | Lightfoot et al. | | |
| 2004/0031072 A1 | 2/2004 | La Rosa et al. | | |
| 2006/0253919 A1 | 11/2006 | Hauge et al. | | |
| 2011/0083234 A1* | 4/2011 | Nguyen | ............. | A01H 1/00 800/301 |
| 2011/0214199 A1 | 9/2011 | Coffin | | |
| 2011/0271409 A1 | 11/2011 | Baley | | |
| 2012/0192315 A1* | 7/2012 | Lightfoot | ............. | C07K 14/415 800/298 |

FOREIGN PATENT DOCUMENTS

WO WO 2011/066384 6/2011

OTHER PUBLICATIONS

Diers et al 2006, Crop Science 46: 1384.*
Butler et al Phytopathology Publication PHYTO-07-19-0225-R Published online Aug. 12, 2019 53 Pages (Year: 2019).*
Nature Communications Publication 8:14822 11 pages (Year: 2016).*
Cook et al Science vol. 338, pp. 1206-1209 (Year: 2012).*
Cook et al Plant Physiology Preview DOI:10.1104/ppl.114.235952 54 pages (Year: 2014).*
Concibido et al Crop Science vol. 44, pp. 1121-1131 (Year: 2004).*
Schmutz et al Nature vol. 463, pp. 178-183 (Year: 2010).*
Cregan et al Crop Science vol. 39, pp. 1464-1490 (Year: 1999).*
Mitchum Phytopathology vol. 106, No. 12, pp. 1444-1450 (Year: 2016).*
Kim et al Theor. Appl. Genet. vol. 129, pp. 2295-2311 (Year: 2016).*
Larking et al The Plant Cell vol. 6, pp. 1065-1076 (Year: 1994).*
Barnard, et al., "Domains of α-SNAP required for the stimulation of exocytosis and for N-ethylmalemide-sensitive fusion protein (NSF) binding and activation," (1996) Mol. Biol. Cell. 7(5):693-701.
Clary, et al., "SNAPs, a family of NSF attachment proteins involved in intracellular membrane fusion in animals and yeast ," (1990) Cell 61:(4):709-721.
Concibido, V.C. et al. "A decade of QTL mapping for cyst nematode resistance in soybean," (2004) Crop Sci. 44:1121-1131.
Cook, D.E. et al., "Copy number variation of multiple genes at Rhg1 mediates nematode resistance in soybean," (2012) Science 338:1206-1209.
Dodds, P.N., et al., "Plant immunity: towards an integrated view of plant-pathogen interactions," (2010) Nat Rev Genet 11, 539-548.
Gheysen, G. et al., "How nematodes manipulate plant development pathways for infection," (2011) Current Opinion in Plant Biology 14, 415-421.

(Continued)

*Primary Examiner* — David H Kruse
(74) *Attorney, Agent, or Firm* — McDonnell Boehnen Hulbert & Berghoff LLP

(57) ABSTRACT

Methods of increasing the resistance of plants, in particular soybeans, to nematodes, in particular soybean cyst nematodes, are provided herein. The methods include increasing the expression of Glyma18g02580, Glyma18g02590 and/or Glyma18g2610 in cells of a plant and in particular in root cells of a plant to increase the resistance of the plant and plant cells to nematodes. The methods include increasing the expression using constitutive promoters or by increasing the copy number of the polynucleotides. Constructs for expressing these polypeptides, transgenic cells, transgenic plants and methods of generating the same are also provided. Methods of screening plant cells for resistance or susceptibility to nematodes are also provided.

23 Claims, 23 Drawing Sheets
Specification includes a Sequence Listing.

(56) References Cited

OTHER PUBLICATIONS

Hyten, D.L. et al., "Highly variable patterns of linkage disequilibrium in multiple soybean populations," (2007) Genetics 175: 1937-1944.

Hyten, D.L. et al., "A high density integrated genetic linkage map of soybean and the development of a 1536 universal soy linkage panel for quantitative trait locus mapping," (2010) Crop Science 50:960-968.

Kim, M., et al., "Fine mapping of the SCN resistance locus rhg1-b from PI 88788," (2010) The Plant Genome 2:81-89.

Kim, M., et al., "Stacking Resistance Alleles from Wild and Domestic Soybean Sources Improves Soybean Cyst Nematode Resistance," (2011) Crop Science 51, 934-943.

Logemann, J. et al. "Differential expression of genes in potato tubers after wounding," (1988) Proc. Natl. Acad. Sci. USA 85:1136-1140.

Matsye, P.D. et al., "The expression of a naturally occurring, truncated allele of an alpha-SNAP gene suppresses plant parasitic neamtode infection," (2012) Plant Mol Biol. DOI 10.1007/s11103 012-9932-z.

Melito, S. et al., "A nematode demographics assay in transgenic roots reveals no significant impacts of Rhg1 locus LRR-Kinase on soybean cyst nematode resistance," (2010) BMC Plant Biology 10:104-118.

Narayanan, R. et al., "Expression of soybean cyst nematode resistance in transgenic hairy roots of soybean," (1999) Crop Science 39, 1680-1686.

Punta, M. et al., "The Pfam protein families database," (2012) Nucleic Acids Research Database 40:D290-D301.

Ruben, E. et al., "Genomic analysis of the rhg1 locus: candidate genes that underlie soybean resistance to the cyst nematode," (2006) Mol. Gen. Genomics. 276:503-516.

Schultz, J.L. et al., The soybean genome database (SoyGD): A browser for display of duplicated, polyploidy, regions and sequence tagged sites on the integrated physical and genetic maps of Glycine max (2006) Nucleic Acids Research 34:D758-D765, Database issue, doi: 10.1093/nar/gkj050.

Yen, et al., "Environmental and developmental regulation of the wound-induced cell wall protein W112 in the halophyte ice plant," (2001) Plant Physiology 127:517-528.

You, F.M. et al., "RJPrimers: Unique transposable element insertion junction discovery and PCR primer design for marker development," (2010) Nucleic Acids Research 38:W313-W320.

International Search Report and Written Opinion for International Application No. PCT/US2013/040773 dated Oct. 25, 2013 (17 pages).

* cited by examiner

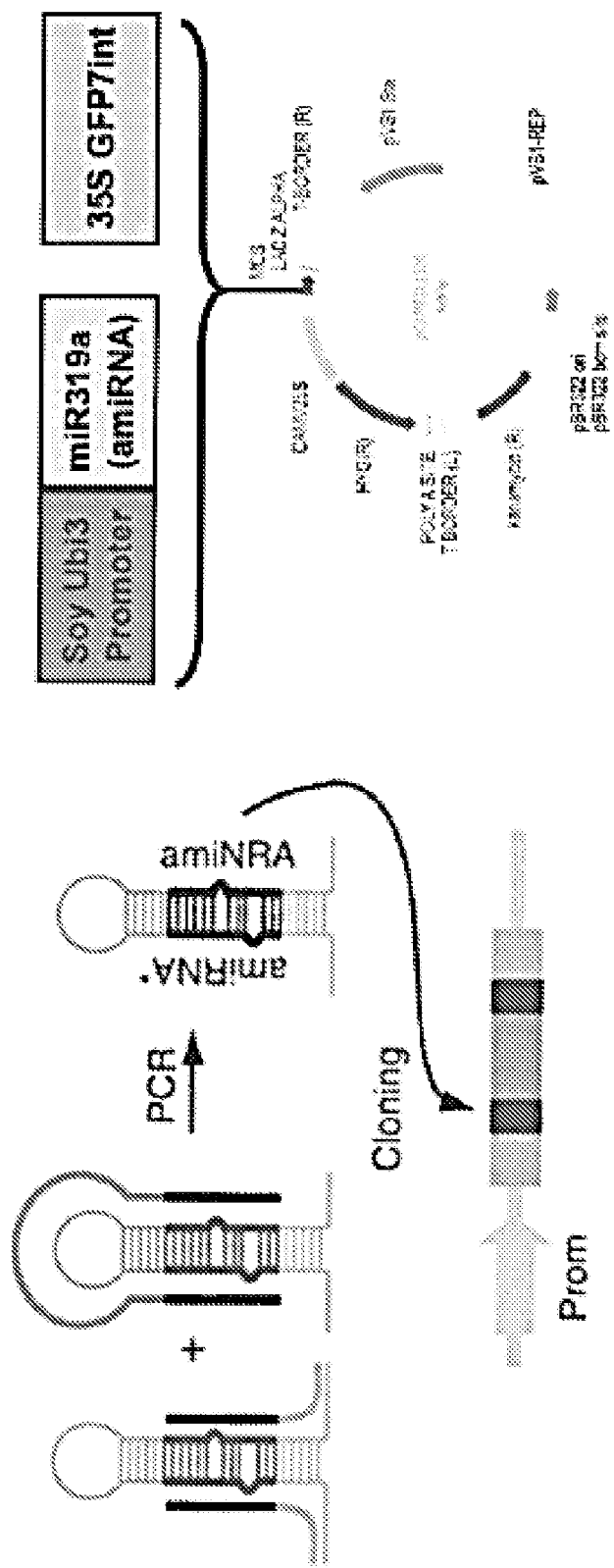
FIG. 2 Silencing strategy: artificial miRNAs
Replace the miR319a sequence with amiRNA sequence targeting gene of interest, under control of a strong soybean promoter

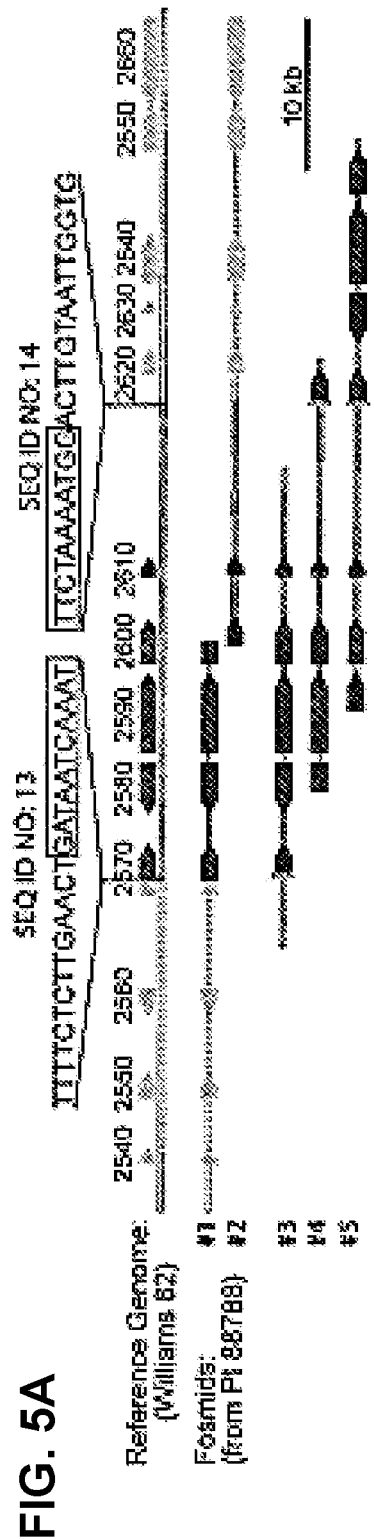
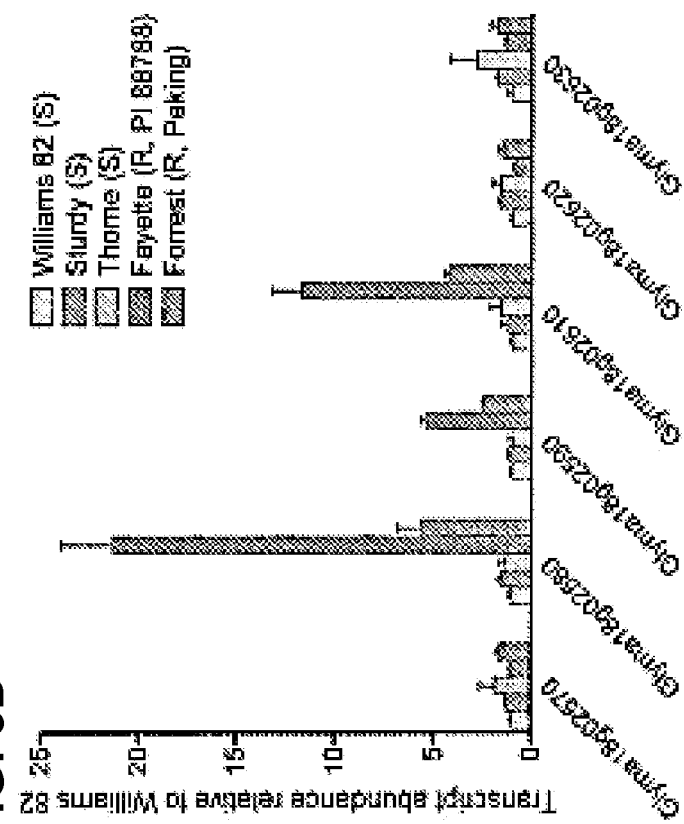
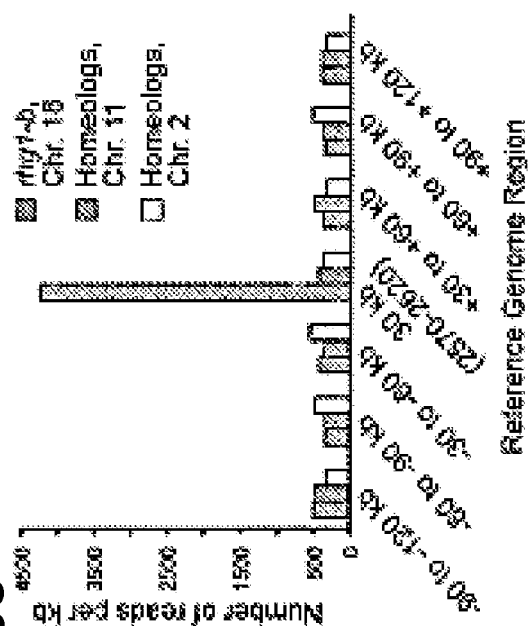
FIG. 5A
FIG. 5B
FIG. 5C
FIG. 5D

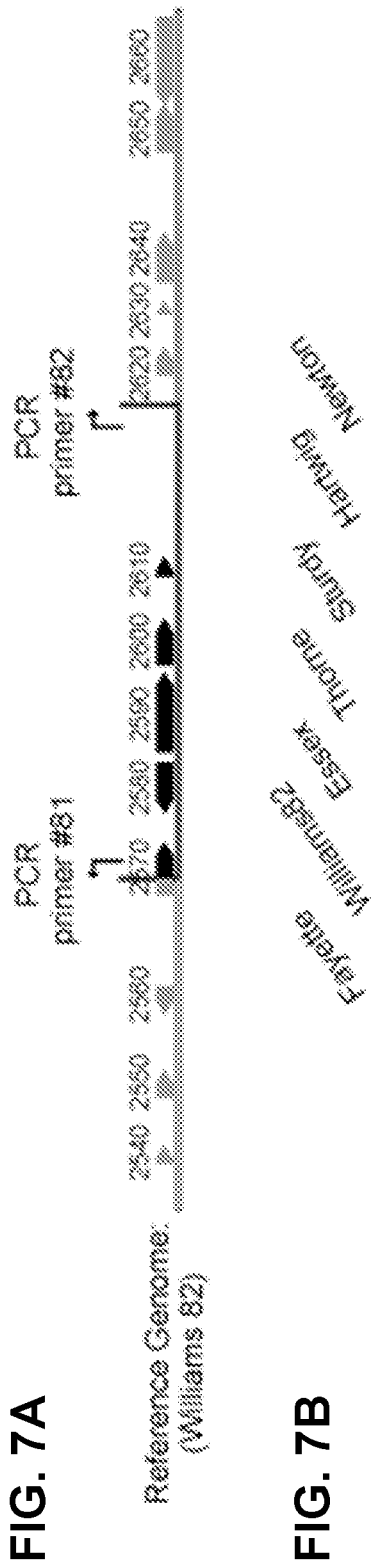
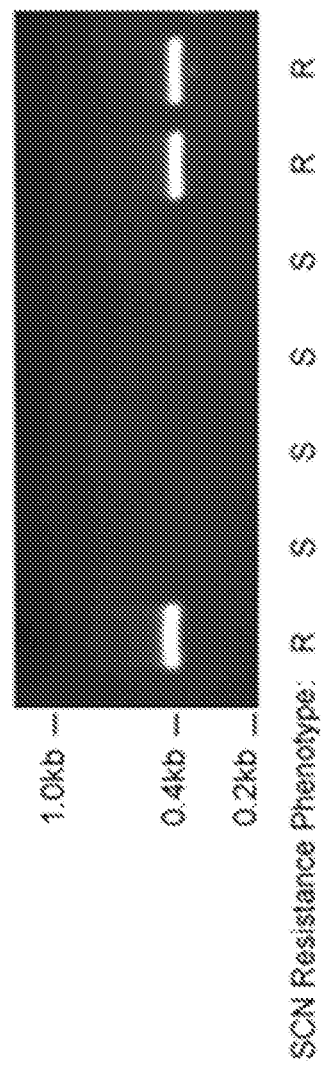
FIG. 7A
FIG. 7B

FIG. 9C

| Region Analyzed (nt position relative to ATG) | DNA treatment | Presence of Methylation | | | | | Polymorphic Methylation |
|---|---|---|---|---|---|---|---|
| | | Fayette | Forrest | Hartwig | Williams82 | Essex | |
| Gm18:2570 | | | | | | | |
| -770 to -1415 | McrBC | Yes | Yes | | Yes | Yes | No |
| -115 to -650 | McrBC | Yes | Yes | | Yes | Yes | No |
| Gm18:2580 | | | | | | | |
| 58 to -72 | McrBC & HpaII | No | No | No | No | No | No |
| 1203 to -72 | McrBC | No | No | No | No | No | No |
| 2639 to 1633 | McrBC | No | No | No | No | No | No |
| Gm18:2580/2590 (relative to 2590 ATG) | | | | | | | |
| -1692 to -1042 | McrBC | Yes | No | No | No | No | Yes |
| -1255 to -709 | McrBC | Yes | No | No | No | No | Yes |
| -798 to -154 | McrBC | Yes | No | No | No | No | Yes |
| Gm18:2590 | | | | | | | |
| 3649 to 4230 | McrBC | No | No | No | No | No | No |
| Gm18:2600 | | | | | | | |
| -230 to 455 | McrBC | No | No | No | No | No | No |
| Gm18:2610 | | | | | | | |
| -2050 to -1301 | McrBC | Yes | Yes | Yes | No | No | Yes |
| -1324 to -184 | McrBC | Yes | Yes | No | No | No | Yes |
| -132 to 757 | McrBC | Yes | No | Yes | No | No | Yes |
| -132 to 179 | HpaII | Yes | Yes | Yes | No | No | Yes |
| -216 to 5 | HpaII | Yes | Yes | Yes | Yes | Yes | No |
| 138 to 256 | HpaII | Yes | Yes | Yes | No | No | Yes |
| Gm18:2620 | | | | | | | |
| -1080 to -1060 | McrBC | No | No | No | No | No | No |
| -880 to -80 | McrBC | No | No | No | No | No | No |

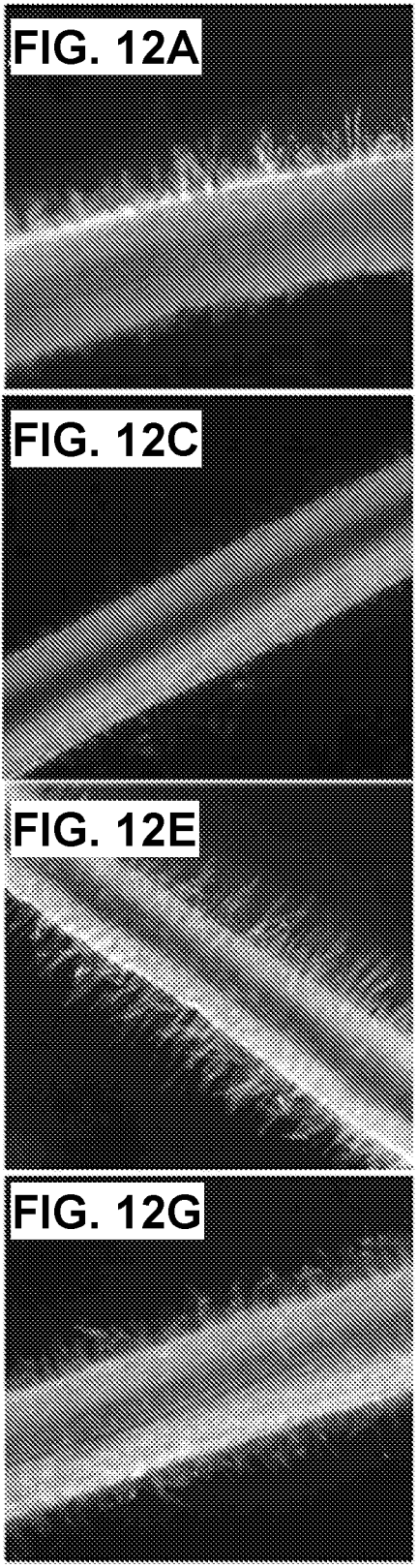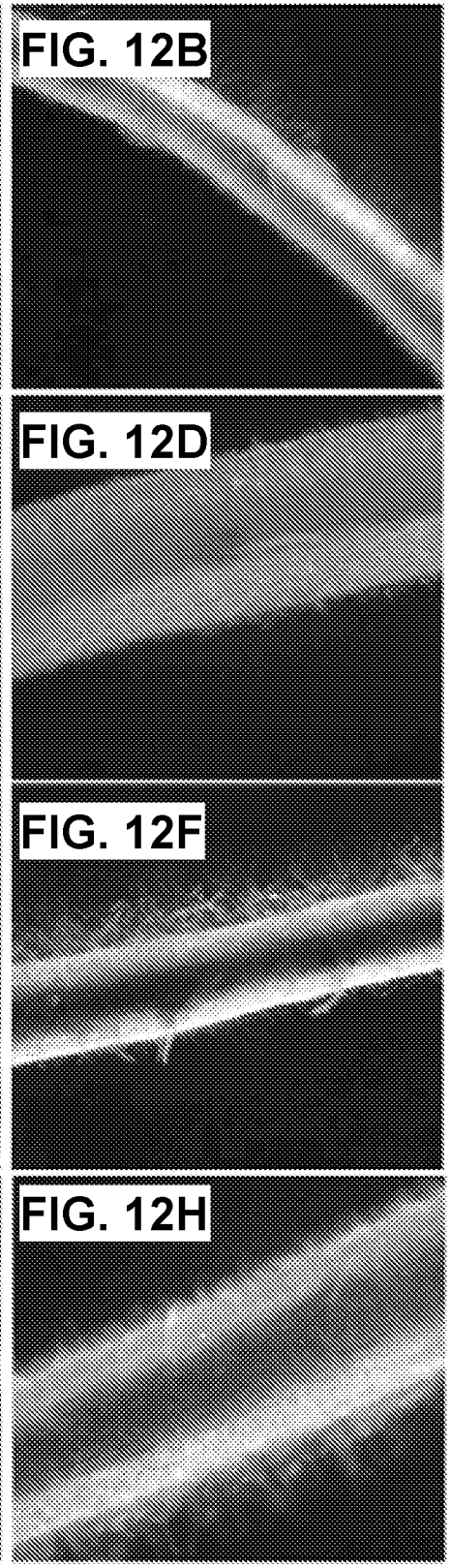

FIG. 13

```
Williams      1   GGTTGCGGCTTGTTTGGCTCCAAGTATGAAGATGCCGCCGATCTCTTCGATAAAGCCGCC
Pek.isoform   1   ............................................................
Fayette       1   ............................................................
Peking        1   ............................................................

Williams     61   AATTGCTTCAAGCTCGCCAAATCATGGGACAAGGCTGGAGCGACATACCTGAAGTTGGCA
Pek.isoform  61   ............................................................
Fayette      61   ............................................................
Peking       61   ............................................................

Williams    121   AGTTGTCATTTGAAGTTGGAAAGCAAGCATGAAGCTGCACAGGCCCATGTCGATGCTGCA
Pek.isoform 121   ............................................................
Fayette     121   ............................................................
Peking      121   ............................................................

Williams    181   CATTGCTACAAAAGACTAATATAAACGAGTCTGTATCTTGCTTAGACCGAGCTGTAAAT
Pek.isoform 181   ............................................................
Fayette     181   ............................................................
Peking      181   ............................................................

Williams    241   CTTTTCTGTGACATTGGAAGACTCTCTATGGCTGCTAGATATTTAAAGGAAATTGCTGAA
Pek.isoform 241   ............................................................
Fayette     241   ............................................................
Peking      241   ............................................................

Williams    301   TTGTACGAGGGTGAACAGAATATTGAGCAGGCTCTTCTTTACTATGAAAAATCAGCTGAT
Pek.isoform 301   ............................................................
Fayette     301   ............................................................
Peking      301   ............................................................

Williams    361   TTTTTTCAAAATGAAGAAGTGACAACTTCTGCGAACCAATGCAAACAAAAGTTGCCCAG
Pek.isoform 361   ............................................................
Fayette     361   ............................................................
Peking      361   ............................................................

Williams    421   TTTGCTGCTCAGCTAGAACAATATCAGAAGTCGATTCACATTTATGAAGAGATAGCTCGC
Pek.isoform 421   ............................................................
Fayette     421   ............................................................
Peking      421   ............................................................

Williams    481   CAATCCCTCAACAATAATTGCTGAAGTATGGAGTTAAAGGACACCTTCTTAATGCTGGC
Pek.isoform 481   ............................................................
Fayette     481   ............................................................
Peking      481   ............................................................

Williams    541   ATCTGCCAACTCTGTAAAGAGGACGTTGTTGCTATAACCAATGCATTAGAACGATATCAG
Pek.isoform 541   .........................▒▒▒▒▒▒▒▒▒▒▒▒▒▒▒▒▒▒▒▒▒▒▒▒▒▒▒▒▒▒▒▒▒-
Fayette     541   ......A.....................................................
Peking      541   ...........................G................................

Williams    601   GAACTGGATCCAACATTTTCAGGAACACGTGAATATAGATTGTTGGCGGACATTGCTGCT
Pek.isoform 565   ............................................................
Fayette     601   ............................................................
Peking      601   ............................................................
```

FIG. 13 - continued

```
Williams      661 GCAATTGATGAAGAAGATGTTGCAAAGTTTACTGATGTTGTCAAGGAATTTGATAGTATG
Pek.isoform   625 ............................................................
Fayette       661 ............................................................
Peking        661 ............................................................

Williams      721 ACCCCTCTGGATTCTTGGAAGACCACACTTCTCTTAAGGGTGAAGGAAAAGCTGAAAGCC
Pek.isoform   685 ............................................................
Fayette       721 ............................................................
Peking        721 ............................................................

Williams      781 AAAGAACTTGAGGAGGATGATCTTACTTGA---       (SEQ ID NO: 9)
Pek.isoform   745 ................T....GG...T.ACTTGA      (SEQ ID NO: 10)
Fayette       781 ..........C..C....GGC..T.ACTTGA         (SEQ ID NO: 8)
Peking        781 ................T....GG...T.ACTTGA      (SEQ ID NO: 11)
```

FIG. 13 - continued

```
peking     MADQLSKGEEFEKKAEKRLSCWKGLFGSKYEDADLFDKAANCFKLAKSWDKAGATYLKLA 60
pekingiso  MADQLSKGEEFEKKAEKRLSCWKGLFGSKYEDADLFDKAANCFKLAKSWDKAGATYLKLA 60
fayette    MADQLSKGEEFEKKAEKRLSCWKGLFGSKYEDADLFDKAANCFKLAKSWDKAGATYLKLA 60
williams   MADQLSKGEEFEKKAEKRLSCWKGLFGSKYEDADLFDKAANCFKLAKSWDKAGATYLKLA 60
           ************************************************************ peking     SCHLKLESHHEAAQAHVDAAHCYKRTNINESVSCLDRAVMLFCDIGRLSMAARYLKEIAE 120
pekingiso  SCHLKLESHHEAAQAHVDAAHCYKKTNINESVSCLDRAVMLFCDIGRLSMAARYLKEIAE 120
fayette    SCHLKLESHHEAAQAHVDAAHCYKKTNINESVSCLDRAVMLFCDIGRLSMAARYLKEIAE 120
williams   SCHLKLESHHEAAQAHVDAAHCYKKTNINESVSCLDRAVMLFCDIGRLSMAARYLKEIAE 120
           ************************************************************ peking     LYEGEQNIEQALVYYEKSADFQNEEVTTSANQCKQKVAQFAAQLEQYQKSIDIYEEIAR 180
pekingiso  LYEGEQNIEQALVYYEKSADFQNEEVTTSANQCKQKVAQFAAQLEQYQKSIDIYEEIAR 180
fayette    LYEGEQNIEQALVYYEKSADFQNEEVTTSANQCKQKVAQFAAQLEQYQKSIDIYEEIAR 180
williams   LYEGEQNIEQALVYYEKSADFQNEEVTTSANQCKQKVAQFAAQLEQYQKSIDIYEEIAR 180
           ************************************************************ peking     QSLMNNLLKYGVRCHLLNAGICQLCKEEVVAITNALERYQELDPTFSGTFEYRLLADIAA 240
pekingiso  QSLMNNLLKYGVRCHLLNAGICQLCKEB------------SLDPTFSGTFEYRLLADIAA 228
fayette    QSLMNNLLKYGVRCHLLNAGICKLCKEDVVAITNALERYQELDPTFSGTFEYRLLADIAA 240
williams   QSLMNNLLKYGVRCHLLNAGICQLCKEDVVAITNALERYQELDPTFSGTFEYRLLADIAA 240
           ******************** *                *********************** peking     AIDEDVAKFTDVVKEFDSWTPLDSWKTTLILRVKEKLKAKELEBYEVIT--  290 (SEQ ID NO:6)
pekingiso  AIDEDVAKFTDVVKEFDSWTPLDSWKTTLILRVKEKLKAKELEBYEVIT--  278 (SEQ ID NO:7)
fayette    AIDEDVAKFTDVVKEFDSWTPLDSWKTTLLIRVKEKLKAKELEQHEAII--  290 (SEQ ID NO:5)
williams   AIDEDVAKFTDVVKEFDSWTPLDSWKTTLLIRVKEKLKAKELEQDEDL--  289 (SEQ ID NO:2)
           ****************************** **********    
```

FIG. 14

SEQUENCE LISTING

```
<160> NUMBER OF SEQ ID NOS: 113

<210> SEQ ID NO 1
<211> LENGTH: 436
<212> TYPE: PRT
<213> ORGANISM: Glycine max
<220> FEATURE:
<221> NAME/KEY: misc_feature
<222> LOCATION: (1)..(436)
<223> OTHER INFORMATION: Glyma18g02580 protein sequence, Variety:
      Williams 82

<400> SEQUENCE: 1

Met Ser Pro Ala Ala Gly Val Ser Val Pro Leu Leu Gly Asp Ser Lys
1               5                   10                  15

Gly Thr Pro Pro Pro Ala Ser Val Pro Gly Ala Val Phe Asn Val Ala
            20                  25                  30

Thr Ser Ile Val Gly Ala Gly Ile Met Ser Ile Pro Ala Ile Met Lys
        35                  40                  45
```

Val Leu Gly Val Val Pro Ala Phe Ala Met Ile Leu Val Ala Val
         50                  55                  60

Leu Ala Glu Leu Ser Val Asp Phe Leu Met Arg Phe Thr His Ser Gly
 65                  70                  75                  80

Glu Thr Thr Thr Tyr Ala Gly Val Met Arg Glu Ala Phe Gly Ser Gly
                 85                  90                  95

Gly Ala Leu Ala Ala Gln Val Cys Val Ile Thr Asn Val Gly Gly
            100                 105                 110

Leu Ile Leu Tyr Leu Ile Ile Gly Asp Val Leu Ser Gly Lys Gln
            115                 120                 125

Asn Gly Gly Glu Val His Leu Gly Ile Leu Gln Gln Trp Phe Gly Ile
130                 135                 140

His Trp Trp Asn Ser Arg Glu Phe Ala Leu Leu Phe Thr Leu Val Phe
145                 150                 155                 160

Val Met Leu Pro Leu Val Leu Tyr Lys Arg Val Glu Ser Leu Lys Tyr
                165                 170                 175

Ser Ser Ala Val Ser Thr Leu Leu Ala Val Ala Phe Val Gly Ile Cys
            180                 185                 190

Cys Gly Leu Ala Ile Thr Ala Leu Val Gln Gly Lys Thr Gln Thr Pro
            195                 200                 205

Arg Leu Phe Pro Arg Leu Asp Tyr Gln Thr Ser Phe Phe Asp Leu Phe
210                 215                 220

Thr Ala Val Pro Val Val Thr Ala Phe Thr Phe His Phe Asn Val
225                 230                 235                 240

His Pro Ile Gly Phe Glu Leu Ala Lys Ala Ser Gln Met Thr Thr Ala
                245                 250                 255

Val Arg Leu Ala Leu Leu Leu Cys Ala Val Ile Tyr Leu Ala Ile Gly
            260                 265                 270

Leu Phe Gly Tyr Met Leu Phe Gly Asp Ser Thr Gln Ser Asp Ile Leu
            275                 280                 285

Ile Asn Phe Asp Gln Asn Ala Gly Ser Ala Val Gly Ser Leu Leu Asn
            290                 295                 300

Ser Leu Val Arg Val Ser Tyr Ala Leu His Ile Met Leu Val Phe Pro
305                 310                 315                 320

Leu Leu Asn Phe Ser Leu Arg Thr Asn Ile Asp Glu Val Leu Phe Pro
                325                 330                 335

Lys Lys Pro Met Leu Ala Thr Asp Asn Lys Arg Phe Met Ile Leu Thr
            340                 345                 350

Leu Val Leu Leu Val Phe Ser Tyr Leu Ala Ala Ile Ala Ile Pro Asp
            355                 360                 365

Ile Trp Tyr Phe Phe Gln Phe Leu Gly Ser Ser Ser Ala Val Cys Leu
370                 375                 380

Ala Phe Ile Phe Pro Gly Ser Ile Val Leu Arg Asp Val Lys Gly Ile
385                 390                 395                 400

Ser Thr Arg Arg Asp Lys Ile Ile Ala Leu Ile Met Ile Ile Leu Ala
                405                 410                 415

Val Val Thr Ser Val Leu Ala Ile Ser Thr Asn Ile Tyr Asn Ala Phe
            420                 425                 430

Ser Ser Lys Ser
            435

<210> SEQ ID NO 2
<211> LENGTH: 289
<212> TYPE: PRT

<213> ORGANISM: Glycine max
<220> FEATURE:
<221> NAME/KEY: misc_feature
<222> LOCATION: (1)..(289)
<223> OTHER INFORMATION: Glyma18g02590 protein sequence, Variety: Williams 82

<400> SEQUENCE: 2

Met Ala Asp Gln Leu Ser Lys Gly Glu Glu Phe Glu Lys Lys Ala Glu
1               5                   10                  15

Lys Lys Leu Ser Gly Trp Gly Leu Phe Gly Ser Lys Tyr Glu Asp Ala
            20                  25                  30

Ala Asp Leu Phe Asp Lys Ala Ala Asn Cys Phe Lys Leu Ala Lys Ser
        35                  40                  45

Trp Asp Lys Ala Gly Ala Thr Tyr Leu Lys Leu Ala Ser Cys His Leu
50                  55                  60

Lys Leu Glu Ser Lys His Glu Ala Ala Gln Ala His Val Asp Ala Ala
65                  70                  75                  80

His Cys Tyr Lys Lys Thr Asn Ile Asn Glu Ser Val Ser Cys Leu Asp
                85                  90                  95

Arg Ala Val Asn Leu Phe Cys Asp Ile Gly Arg Leu Ser Met Ala Ala
            100                 105                 110

Arg Tyr Leu Lys Glu Ile Ala Glu Leu Tyr Glu Gly Glu Gln Asn Ile
        115                 120                 125

Glu Gln Ala Leu Val Tyr Tyr Glu Lys Ser Ala Asp Phe Phe Gln Asn
130                 135                 140

Glu Glu Val Thr Thr Ser Ala Asn Gln Cys Lys Gln Lys Val Ala Gln
145                 150                 155                 160

Phe Ala Ala Gln Leu Glu Gln Tyr Gln Lys Ser Ile Asp Ile Tyr Glu
                165                 170                 175

Glu Ile Ala Arg Gln Ser Leu Asn Asn Asn Leu Leu Lys Tyr Gly Val
            180                 185                 190

Lys Gly His Leu Leu Asn Ala Gly Ile Cys Gln Leu Cys Lys Glu Asp
        195                 200                 205

Val Val Ala Ile Thr Asn Ala Leu Glu Arg Tyr Gln Glu Leu Asp Pro
210                 215                 220

Thr Phe Ser Gly Thr Arg Glu Tyr Arg Leu Leu Ala Asp Ile Ala Ala
225                 230                 235                 240

Ala Ile Asp Glu Glu Asp Val Ala Lys Phe Thr Asp Val Val Lys Glu
                245                 250                 255

Phe Asp Ser Met Thr Pro Leu Asp Ser Trp Lys Thr Thr Leu Leu Leu
            260                 265                 270

Arg Val Lys Glu Lys Leu Lys Ala Lys Glu Leu Glu Glu Asp Asp Leu
        275                 280                 285

Thr

<210> SEQ ID NO 3
<211> LENGTH: 107
<212> TYPE: PRT
<213> ORGANISM: Glycine max
<220> FEATURE:
<221> NAME/KEY: misc_feature
<222> LOCATION: (1)..(107)
<223> OTHER INFORMATION: Glyma18g02610 protein sequence, Variety: Williams 82

<400> SEQUENCE: 3

Met Arg Met Leu Thr Gly Asp Ser Ala Ala Asp Asn Ser Phe Arg Phe

```
1               5                  10                 15
Val Pro Gln Ser Ile Ala Ala Phe Gly Ser Thr Val Ile Val Glu Gly
            20                 25                 30

Cys Asp Ser Ala Arg Asn Ile Ala Trp Val His Ala Trp Thr Val Thr
            35                 40                 45

Asp Gly Met Ile Thr Gln Ile Arg Glu Tyr Phe Asn Thr Ala Leu Thr
            50                 55                 60

Val Thr Arg Ile His Asp Ser Gly Glu Ile Val Pro Ala Arg Ser Gly
65                  70                 75                  80

Ala Gly Arg Leu Pro Cys Val Trp Glu Ser Ser Val Ser Gly Arg Val
                85                 90                 95

Gly Lys Ser Val Pro Gly Leu Val Leu Ala Ile
                100                105

<210> SEQ ID NO 4
<211> LENGTH: 536
<212> TYPE: PRT
<213> ORGANISM: Glycine max
<220> FEATURE:
<221> NAME/KEY: misc_feature
<222> LOCATION: (1)..(536)
<223> OTHER INFORMATION: Glyma18g02600 protein sequence, Variety:
      Williams 82

<400> SEQUENCE: 4

Met Val Ser Val Asp Asp Gly Ile Val Asn Pro Asn Asp Glu Ile Glu
1               5                  10                 15

Lys Ser Asn Gly Ser Lys Val Asn Glu Phe Ala Ser Met Asp Ile Ser
            20                 25                 30

Ala Thr Gln Lys Ser Tyr Leu Asn Ser Glu Asp Pro Gln Arg Arg Leu
            35                 40                 45

Gln Gly Thr Leu Ile Ser Ser Val Thr Asn Arg Ile Asn Phe Leu
            50                 55                 60

Lys Phe Gly Ser Ala Ser Ala Lys Phe Lys Arg Leu Thr Glu Arg
65                  70                 75                  80

Asp Gln Val Ser Ile Ser Val Pro Ser Pro Arg Ser Lys Ser Leu Arg
                85                 90                 95

Ser Arg Phe Ser Gly Met Phe Ala Gln Lys Leu Asp Trp Ala Ser Val
                100                105                110

Lys Lys Met Cys Met Glu Trp Ile Arg Asn Pro Val Asn Met Ala Leu
            115                120                125

Phe Val Trp Ile Ile Cys Val Ala Val Ser Gly Ala Ile Leu Phe Leu
            130                135                140

Val Met Thr Gly Met Leu Asn Gly Val Leu Pro Arg Lys Ser Lys Arg
145                 150                155                 160

Asn Ala Trp Phe Glu Val Asn Asn Gln Ile Leu Asn Ala Val Phe Thr
                165                170                175

Leu Ile Pro Asn Asp Ile Ser Ser Leu Arg Lys Val Tyr Cys Lys Asn
            180                185                190

Val Thr Tyr Lys Pro His Glu Trp Thr His Met Met Val Val Ile
            195                200                205

Leu Leu His Val Asn Cys Phe Ala Gln Tyr Ala Leu Cys Gly Leu Asn
            210                215                220

Leu Gly Tyr Lys Arg Ser Glu Arg Pro Ala Ile Gly Val Gly Ile Cys
225                 230                235                 240

Ile Ser Phe Ala Ile Ala Gly Leu Tyr Thr Ile Leu Ser Pro Leu Gly
```

```
            245                 250                 255
Lys Asp Tyr Asp Cys Glu Met Asp Glu Glu Ala Gln Val Gln Ile Thr
        260                 265                 270

Ala Ser Gln Gly Lys Glu Gln Leu Arg Glu Lys Pro Thr Glu Lys Lys
    275                 280                 285

Tyr Ser Phe Ala Ser Lys Asp Gln Gln Arg Val Val Glu Asn Arg Pro
290                 295                 300

Lys Trp Ser Gly Gly Ile Leu Asp Ile Trp Asn Asp Ile Ser Leu Ala
305                 310                 315                 320

Tyr Leu Ser Leu Phe Cys Thr Phe Cys Val Leu Gly Trp Asn Met Lys
                325                 330                 335

Arg Leu Gly Phe Gly Asn Met Tyr Val His Ile Ala Ile Phe Met Leu
                340                 345                 350

Phe Cys Met Ala Pro Phe Trp Ile Phe Leu Leu Ala Ser Val Asn Ile
                355                 360                 365

Asp Asp Asp Asn Val Arg Gln Ala Leu Ala Ala Val Gly Ile Ile Leu
370                 375                 380

Cys Phe Leu Gly Leu Leu Tyr Gly Gly Phe Trp Arg Ile Gln Met Arg
385                 390                 395                 400

Lys Arg Phe Asn Leu Pro Ala Tyr Asp Phe Cys Phe Gly Lys Pro Ser
                405                 410                 415

Ala Ser Asp Cys Thr Leu Trp Leu Pro Cys Cys Trp Cys Ser Leu Ala
                420                 425                 430

Gln Glu Ala Arg Thr Arg Asn Asn Tyr Asp Leu Val Glu Asp Lys Phe
                435                 440                 445

Ser Arg Lys Glu Thr Asp Thr Ser Asp Gln Pro Ser Ile Ser Pro Leu
    450                 455                 460

Ala Arg Glu Asp Val Val Ser Thr Arg Ser Gly Thr Ser Ser Pro Met
465                 470                 475                 480

Gly Ser Thr Ser Asn Ser Ser Pro Tyr Met Met Lys Thr Ser Ser Ser
                485                 490                 495

Pro Asn Ser Ser Asn Val Leu Lys Gly Tyr Tyr Ser Pro Asp Lys Met
                500                 505                 510

Leu Ser Thr Leu Asn Glu Asp Asn Cys Glu Arg Gly Gln Asp Gly Thr
                515                 520                 525

Met Asn Pro Leu Tyr Ala Gln Lys
                530                 535

<210> SEQ ID NO 5
<211> LENGTH: 290
<212> TYPE: PRT
<213> ORGANISM: Glycine max
<220> FEATURE:
<221> NAME/KEY: misc_feature
<222> LOCATION: (1)..(290)
<223> OTHER INFORMATION: Glyma18g02590 protein sequence, Variety:
      Fayette

<400> SEQUENCE: 5

Met Ala Asp Gln Leu Ser Lys Gly Glu Glu Phe Glu Lys Lys Ala Glu
1               5                   10                  15

Lys Lys Leu Ser Gly Trp Gly Leu Phe Gly Ser Lys Tyr Glu Asp Ala
                20                  25                  30

Ala Asp Leu Phe Asp Lys Ala Ala Asn Cys Phe Lys Leu Ala Lys Ser
            35                  40                  45

Trp Asp Lys Ala Gly Ala Thr Tyr Leu Lys Leu Ala Ser Cys His Leu
```

```
            50                  55                  60
Lys Leu Glu Ser Lys His Glu Ala Ala Gln Ala His Val Asp Ala Ala
 65                  70                  75                  80

His Cys Tyr Lys Lys Thr Asn Ile Asn Glu Ser Val Ser Cys Leu Asp
                 85                  90                  95

Arg Ala Val Asn Leu Phe Cys Asp Ile Gly Arg Leu Ser Met Ala Ala
             100                 105                 110

Arg Tyr Leu Lys Glu Ile Ala Glu Leu Tyr Glu Gly Glu Gln Asn Ile
         115                 120                 125

Glu Gln Ala Leu Val Tyr Tyr Glu Lys Ser Ala Asp Phe Phe Gln Asn
130                 135                 140

Glu Glu Val Thr Thr Ser Ala Asn Gln Cys Lys Gln Lys Val Ala Gln
145                 150                 155                 160

Phe Ala Ala Gln Leu Glu Gln Tyr Gln Lys Ser Ile Asp Ile Tyr Glu
                165                 170                 175

Glu Ile Ala Arg Gln Ser Leu Asn Asn Asn Leu Leu Lys Tyr Gly Val
            180                 185                 190

Lys Gly His Leu Leu Asn Ala Gly Ile Cys Lys Leu Cys Lys Glu Asp
        195                 200                 205

Val Val Ala Ile Thr Asn Ala Leu Glu Arg Tyr Gln Glu Leu Asp Pro
    210                 215                 220

Thr Phe Ser Gly Thr Arg Glu Tyr Arg Leu Leu Ala Asp Ile Ala Ala
225                 230                 235                 240

Ala Ile Asp Glu Glu Asp Val Ala Lys Phe Thr Asp Val Val Lys Glu
                245                 250                 255

Phe Asp Ser Met Thr Pro Leu Asp Ser Trp Lys Thr Thr Leu Leu Leu
            260                 265                 270

Arg Val Lys Glu Lys Leu Lys Ala Lys Glu Leu Glu Gln His Glu Ala
        275                 280                 285

Ile Thr
    290

<210> SEQ ID NO 6
<211> LENGTH: 290
<212> TYPE: PRT
<213> ORGANISM: Glycine max
<220> FEATURE:
<221> NAME/KEY: misc_feature
<222> LOCATION: (1)..(290)
<223> OTHER INFORMATION: Glyma18g02590 protein sequence, Variety: Peking

<400> SEQUENCE: 6

Met Ala Asp Gln Leu Ser Lys Gly Glu Glu Phe Glu Lys Lys Ala Glu
  1               5                  10                  15

Lys Lys Leu Ser Gly Trp Gly Leu Phe Gly Ser Lys Tyr Glu Asp Ala
             20                  25                  30

Ala Asp Leu Phe Asp Lys Ala Ala Asn Cys Phe Lys Leu Ala Lys Ser
         35                  40                  45

Trp Asp Lys Ala Gly Ala Thr Tyr Leu Lys Leu Ala Ser Cys His Leu
     50                  55                  60

Lys Leu Glu Ser Lys His Glu Ala Ala Gln Ala His Val Asp Ala Ala
 65                  70                  75                  80

His Cys Tyr Lys Lys Thr Asn Ile Asn Glu Ser Val Ser Cys Leu Asp
                 85                  90                  95

Arg Ala Val Asn Leu Phe Cys Asp Ile Gly Arg Leu Ser Met Ala Ala
            100                 105                 110
```

Arg Tyr Leu Lys Glu Ile Ala Glu Leu Tyr Glu Gly Glu Gln Asn Ile
            115                 120                 125

Glu Gln Ala Leu Val Tyr Tyr Glu Lys Ser Ala Asp Phe Phe Gln Asn
        130                 135                 140

Glu Glu Val Thr Thr Ser Ala Asn Gln Cys Lys Gln Lys Val Ala Gln
145                 150                 155                 160

Phe Ala Ala Gln Leu Glu Gln Tyr Gln Lys Ser Ile Asp Ile Tyr Glu
                165                 170                 175

Glu Ile Ala Arg Gln Ser Leu Asn Asn Asn Leu Leu Lys Tyr Gly Val
            180                 185                 190

Lys Gly His Leu Leu Asn Ala Gly Ile Cys Gln Leu Cys Lys Glu Glu
        195                 200                 205

Val Val Ala Ile Thr Asn Ala Leu Glu Arg Tyr Gln Glu Leu Asp Pro
210                 215                 220

Thr Phe Ser Gly Thr Arg Glu Tyr Arg Leu Leu Ala Asp Ile Ala Ala
225                 230                 235                 240

Ala Ile Asp Glu Glu Asp Val Ala Lys Phe Thr Asp Val Val Lys Glu
                245                 250                 255

Phe Asp Ser Met Thr Pro Leu Asp Ser Trp Lys Thr Thr Leu Leu Leu
            260                 265                 270

Arg Val Lys Glu Lys Leu Lys Ala Lys Glu Leu Glu Glu Tyr Glu Val
        275                 280                 285

Ile Thr
    290

<210> SEQ ID NO 7
<211> LENGTH: 278
<212> TYPE: PRT
<213> ORGANISM: Glycine max
<220> FEATURE:
<221> NAME/KEY: misc_feature
<222> LOCATION: (1)..(278)
<223> OTHER INFORMATION: Glyma18g02590 protein sequence, Variety: Peking
      Iso

<400> SEQUENCE: 7

Met Ala Asp Gln Leu Ser Lys Gly Glu Glu Phe Glu Lys Lys Ala Glu
1               5                   10                  15

Lys Lys Leu Ser Gly Trp Gly Leu Phe Gly Ser Lys Tyr Glu Asp Ala
            20                  25                  30

Ala Asp Leu Phe Asp Lys Ala Ala Asn Cys Phe Lys Leu Ala Lys Ser
        35                  40                  45

Trp Asp Lys Ala Gly Ala Thr Tyr Leu Lys Leu Ala Ser Cys His Leu
    50                  55                  60

Lys Leu Glu Ser Lys His Glu Ala Ala Gln His Val Asp Ala Ala
65                  70                  75                  80

His Cys Tyr Lys Lys Thr Asn Ile Asn Glu Ser Val Ser Cys Leu Asp
                85                  90                  95

Arg Ala Val Asn Leu Phe Cys Asp Ile Gly Arg Leu Ser Met Ala Ala
            100                 105                 110

Arg Tyr Leu Lys Glu Ile Ala Glu Leu Tyr Glu Gly Glu Gln Asn Ile
        115                 120                 125

Glu Gln Ala Leu Val Tyr Tyr Glu Lys Ser Ala Asp Phe Phe Gln Asn
    130                 135                 140

Glu Glu Val Thr Thr Ser Ala Asn Gln Cys Lys Gln Lys Val Ala Gln
145                 150                 155                 160

```
Phe Ala Ala Gln Leu Glu Gln Tyr Gln Lys Ser Ile Asp Ile Tyr Glu
                165                 170                 175

Glu Ile Ala Arg Gln Ser Leu Asn Asn Leu Leu Lys Tyr Gly Val
            180                 185                 190

Lys Gly His Leu Leu Asn Ala Gly Ile Cys Gln Leu Cys Lys Glu Glu
        195                 200                 205

Glu Leu Asp Pro Thr Phe Ser Gly Thr Arg Glu Tyr Arg Leu Leu Ala
    210                 215                 220

Asp Ile Ala Ala Ala Ile Asp Glu Glu Asp Val Ala Lys Phe Thr Asp
225                 230                 235                 240

Val Val Lys Glu Phe Asp Ser Met Thr Pro Leu Asp Ser Trp Lys Thr
                245                 250                 255

Thr Leu Leu Leu Arg Val Lys Glu Lys Leu Lys Ala Lys Glu Leu Glu
            260                 265                 270

Glu Tyr Glu Val Ile Thr
        275
```

```
<210> SEQ ID NO 8
<211> LENGTH: 309
<212> TYPE: DNA
<213> ORGANISM: Glycine max
<220> FEATURE:
<221> NAME/KEY: misc_feature
<222> LOCATION: (1)..(309)
<223> OTHER INFORMATION: Glyma18g02590 nucleotide sequence partial,
      Variety: Fayette

<400> SEQUENCE: 8
aagtatggag ttaaaggaca ccttcttaat gctggcatct gcaaactctg taaagaggac      60
gttgttgcta taaccaatgc attagaacga tatcaggaac tggatccaac attttcagga     120
acacgtgaat atagattgtt ggcggacatt gctgctgcaa ttgatgaaga agatgttgca     180
aagtttactg atgttgtcaa ggaatttgat agtatgaccc ctctggattc ttggaagacc     240
acacttctct aagggtgaa ggaaaagctg aaagccaaag aacttgagca gcatgaggct     300
attacttga                                                           309
```

```
<210> SEQ ID NO 9
<211> LENGTH: 306
<212> TYPE: DNA
<213> ORGANISM: Glycine max
<220> FEATURE:
<221> NAME/KEY: misc_feature
<222> LOCATION: (1)..(306)
<223> OTHER INFORMATION: Glyma18g02590 nucleotide sequence partial,
      Variety: Williams 82

<400> SEQUENCE: 9
aagtatggag ttaaaggaca ccttcttaat gctggcatct gccaactctg taaagaggac      60
gttgttgcta taaccaatgc attagaacga tatcaggaac tggatccaac attttcagga     120
acacgtgaat atagattgtt ggcggacatt gctgctgcaa ttgatgaaga agatgttgca     180
aagtttactg atgttgtcaa ggaatttgat agtatgaccc ctctggattc ttggaagacc     240
acacttctct aagggtgaa ggaaaagctg aaagccaaag aacttgagga ggatgatctt     300
acttga                                                              306
```

```
<210> SEQ ID NO 10
<211> LENGTH: 273
<212> TYPE: DNA
```

```
<213> ORGANISM: Glycine max
<220> FEATURE:
<221> NAME/KEY: misc_feature
<222> LOCATION: (1)..(273)
<223> OTHER INFORMATION: Glyma18g02590 nucleotide sequence partial,
      Variety: Peking Iso

<400> SEQUENCE: 10
aagtatggag ttaaaggaca ccttcttaat gctggcatct gccaactctg taaagaggag      60
gaactggatc caacattttc aggaacacgt gaatatagat tgttggcgga cattgctgct     120
gcaattgatg aagaagatgt tgcaaagttt actgatgttg tcaaggaatt tgatagtatg     180 accccctctgg attcttggaa gaccacactt ctcttaaggg tgaaggaaaa gctgaaagcc     240
aaagaacttg aggagtatga ggttattact tga                                   273

<210> SEQ ID NO 11
<211> LENGTH: 309
<212> TYPE: DNA
<213> ORGANISM: Glycine max
<220> FEATURE:
<221> NAME/KEY: misc_feature
<222> LOCATION: (1)..(309)
<223> OTHER INFORMATION: Glyma18g02590 nucleotide sequence partial,
      Variety: Peking

<400> SEQUENCE: 11
aagtatggag ttaaaggaca ccttcttaat gctggcatct gccaactctg taaagaggag      60
gttgttgcta taaccaatgc attagaacga tatcaggaac tggatccaac attttcagga    120
acacgtgaat atagattgtt ggcggacatt gctgctgcaa ttgatgaaga agatgttgca    180
aagtttactg atgttgtcaa ggaatttgat agtatgaccc ctctggattc ttggaagacc    240
acacttctct aagggtgaa ggaaaagctg aaagccaaag aacttgagga gtatgaggtt      300
attacttga                                                              309

<210> SEQ ID NO 12
<211> LENGTH: 309
<212> TYPE: DNA
<213> ORGANISM: Glycine max
<220> FEATURE:
<221> NAME/KEY: misc_feature
<222> LOCATION: (1)..(309)
<223> OTHER INFORMATION: Glyma18g02590 nucleotide sequence
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t

<400> SEQUENCE: 12
aagtatggag ttaaaggaca ccttcttaat gctggcatct gccaactctg taaagaggan      60
gttgttgcta taaccaatgc attagaacga tatcaggaac tggatccaac attttcagga    120
acacgtgaat atagattgtt ggcggacatt gctgctgcaa ttgatgaaga agatgttgca    180
aagtttactg atgttgtcaa ggaatttgat agtatgaccc ctctggattc ttggaagacc    240
acacttctct aagggtgaa ggaaaagctg aaagccaaag aacttgagga gnatgaggnt      300
attacttga                                                              309
```

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide: Glycine max,
      Junction 1Williams 82

<400> SEQUENCE: 13
ttttctcttg aactgataat caaat                                         25

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide: Glycine max,
      Junction 2 Williams 82

<400> SEQUENCE: 14
ttctaaaatg gacttgtaat tggtg                                         25

<210> SEQ ID NO 15
<211> LENGTH: 41
<212> TYPE: DNA
<213> ORGANISM: Artificial Sequence
<220> FEATURE:
<223> OTHER INFORMATION: Synthetic oligonucleotide: Glycine max,
      Junction resistant varieties

<400> SEQUENCE: 15
atagaagttt ctaaaatgga ctgataatca aatagttatt g                       41

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 16

Glu Glu Asp Leu Thr
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 17

Gln His Glu Ala Ile Thr
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 18

Tyr Glu Val Ile Thr
1               5

<210> SEQ ID NO 19
<211> LENGTH: 39
<212> TYPE: DNA
<213> ORGANISM: Artificial Sequence
<220> FEATURE:
<223> OTHER INFORMATION: Synthetic oligonucleotide: 2570 hpRNAi _F

<400> SEQUENCE: 19
aggatccatt taaatcaagt actcttcccc acaaaagct                                      39

<210> SEQ ID NO 20
<211> LENGTH: 40
<212> TYPE: DNA
<213> ORGANISM: Artificial Sequence
<220> FEATURE:
<223> OTHER INFORMATION: Synthetic oligonucleotide: 2570 hpRNAi _R

<400> SEQUENCE: 20
acctaggagg cgcgcctggg gccatttcag taattaggtc                                     40

<210> SEQ ID NO 21
<211> LENGTH: 37
<212> TYPE: DNA
<213> ORGANISM: Artificial Sequence
<220> FEATURE:
<223> OTHER INFORMATION: Synthetic oligonucleotide: 2580 hpRNAi _F

<400> SEQUENCE: 21
acctaggagg cgcgcctcat gaaggttctc ggcgtag                                        37

<210> SEQ ID NO 22
<211> LENGTH: 36
<212> TYPE: DNA
<213> ORGANISM: Artificial Sequence
<220> FEATURE:
<223> OTHER INFORMATION: Synthetic oligonucleotide: 2580 hpRNAi _R

<400> SEQUENCE: 22
aggatccatt taaatccacc agtgaattcc aaacca                                         36

<210> SEQ ID NO 23
<211> LENGTH: 36
<212> TYPE: DNA
<213> ORGANISM: Artificial Sequence
<220> FEATURE:
<223> OTHER INFORMATION: Synthetic oligonucleotide: 2590 hpRNAi _F

<400> SEQUENCE: 23
gacctaggcg cgccggactt ggtcgtcaac acagtc                                         36

<210> SEQ ID NO 24
<211> LENGTH: 36
<212> TYPE: DNA
<213> ORGANISM: Artificial Sequence
<220> FEATURE:
<223> OTHER INFORMATION: Synthetic oligonucleotide: 2590 hpRNAi _R

<400> SEQUENCE: 24
gcggatccat ttaaatgagc agcaaactgg gcaact                                         36

<210> SEQ ID NO 25
<211> LENGTH: 37
<212> TYPE: DNA
<213> ORGANISM: Artificial Sequence
<220> FEATURE:
<223> OTHER INFORMATION: Synthetic oligonucleotide: 2600 hpRNAi _F

<400> SEQUENCE: 25
acctaggagg cgcgccgcca aattcaaaag gcttgct            37

<210> SEQ ID NO 26
<211> LENGTH: 36
<212> TYPE: DNA
<213> ORGANISM: Artificial Sequence
<220> FEATURE:
<223> OTHER INFORMATION: Synthetic oligonucleotide: 2600 hpRNAi _R

<400> SEQUENCE: 26
aggatccatt taaatcacca ttcaacatgc ctgtca             36

<210> SEQ ID NO 27
<211> LENGTH: 41
<212> TYPE: DNA
<213> ORGANISM: Artificial Sequence
<220> FEATURE:
<223> OTHER INFORMATION: Synthetic oligonucleotide: 2610 hpRNAi _F

<400> SEQUENCE: 27
taacctagga ggcgcgccac aactccttcc gattcgttcc g       41

<210> SEQ ID NO 28
<211> LENGTH: 40
<212> TYPE: DNA
<213> ORGANISM: Artificial Sequence
<220> FEATURE:
<223> OTHER INFORMATION: Synthetic oligonucleotide: 2610 hpRNAi _R

<400> SEQUENCE: 28
caggatccat ttaaatagat acaaccacct gaatacgccc         40

<210> SEQ ID NO 29
<211> LENGTH: 38
<212> TYPE: DNA
<213> ORGANISM: Artificial Sequence
<220> FEATURE:
<223> OTHER INFORMATION: Synthetic oligonucleotide: 2620 hpRNAi _F

<400> SEQUENCE: 29
aggatccatt taaatctcgc aacaccatat ccagagta           38

<210> SEQ ID NO 30
<211> LENGTH: 39
<212> TYPE: DNA
<213> ORGANISM: Artificial Sequence
<220> FEATURE:
<223> OTHER INFORMATION: Synthetic oligonucleotide: 2620 hpRNAi _R

<400> SEQUENCE: 30
acctaggagg cgcgccggtg ttaaggtcga acctgcgaa          39

<210> SEQ ID NO 31
<211> LENGTH: 40
<212> TYPE: DNA
<213> ORGANISM: Artificial Sequence
<220> FEATURE:
<223> OTHER INFORMATION: Synthetic oligonucleotide: 2590-1 I miR-s

<400> SEQUENCE: 31
gatattggtt atagcaacac cgttctctct tttgtattcc         40

<210> SEQ ID NO 32

```
<211> LENGTH: 37
<212> TYPE: DNA
<213> ORGANISM: Artificial Sequence
<220> FEATURE:
<223> OTHER INFORMATION: Synthetic oligonucleotide: 2590-1 II miR-a

<400> SEQUENCE: 32
gaactttgct ataaccaata tcaaagagaa tcaatga                              37

<210> SEQ ID NO 33
<211> LENGTH: 40
<212> TYPE: DNA
<213> ORGANISM: Artificial Sequence
<220> FEATURE:
<223> OTHER INFORMATION: Synthetic oligonucleotide: 2590-1 III miR*s

<400> SEQUENCE: 33
gaacagtgtt gctattacca atttcacagg tcgtgatatg                           40

<210> SEQ ID NO 34
<211> LENGTH: 40
<212> TYPE: DNA
<213> ORGANISM: Artificial Sequence
<220> FEATURE:
<223> OTHER INFORMATION: Synthetic oligonucleotide: 2590-1 IV miR*a

<400> SEQUENCE: 34
gaaattggta atagcaacac tgttctacat atatattcct                           40

<210> SEQ ID NO 35
<211> LENGTH: 40
<212> TYPE: DNA
<213> ORGANISM: Artificial Sequence
<220> FEATURE:
<223> OTHER INFORMATION: Synthetic oligonucleotide: 2610-1 I miR-s

<400> SEQUENCE: 35
gatatttccc gacccgacgg gactctctct tttgtattcc                           40

<210> SEQ ID NO 36
<211> LENGTH: 40
<212> TYPE: DNA
<213> ORGANISM: Artificial Sequence
<220> FEATURE:
<223> OTHER INFORMATION: Synthetic oligonucleotide: 2610-1 II miR-a

<400> SEQUENCE: 36
gagtcccgtc gggtcgggaa atatcaaaga gaatcaatga                           40

<210> SEQ ID NO 37
<211> LENGTH: 40
<212> TYPE: DNA
<213> ORGANISM: Artificial Sequence
<220> FEATURE:
<223> OTHER INFORMATION: Synthetic oligonucleotide: 2610-1 III miR*s

<400> SEQUENCE: 37
gagtaccgtc gggtccggaa atttcacagg tcgtgatatg                           40

<210> SEQ ID NO 38
<211> LENGTH: 40
<212> TYPE: DNA
<213> ORGANISM: Artificial Sequence
<220> FEATURE:
<223> OTHER INFORMATION: Synthetic oligonucleotide: 2610-1 IV miR*a

<400> SEQUENCE: 38
```

```
gaaatttccg gacccgacgg tactctacat atatattcct                    40

<210> SEQ ID NO 39
<211> LENGTH: 40
<212> TYPE: DNA
<213> ORGANISM: Artificial Sequence
<220> FEATURE:
<223> OTHER INFORMATION: Synthetic oligonucleotide: 2610-2 I miR-s

<400> SEQUENCE: 39
gatatccagt caccgcgacg tggtctctct tttgtattcc                    40

<210> SEQ ID NO 40
<211> LENGTH: 40
<212> TYPE: DNA
<213> ORGANISM: Artificial Sequence
<220> FEATURE:
<223> OTHER INFORMATION: Synthetic oligonucleotide: 2610-2 II miR-a

<400> SEQUENCE: 40
gaccacgtcg cggtgactgg atatcaaaga gaatcaatga                    40

<210> SEQ ID NO 41
<211> LENGTH: 40
<212> TYPE: DNA
<213> ORGANISM: Artificial Sequence
<220> FEATURE:
<223> OTHER INFORMATION: Synthetic oligonucleotide: 2610-2 III miR*s

<400> SEQUENCE: 41
gaccccgtcg cggtgtctgg atttcacagg tcgtgatatg                    40

<210> SEQ ID NO 42
<211> LENGTH: 40
<212> TYPE: DNA
<213> ORGANISM: Artificial Sequence
<220> FEATURE:
<223> OTHER INFORMATION: Synthetic oligonucleotide: 2610-2 IV miR*a

<400> SEQUENCE: 42
gaaatccaga caccgcgacg gggtctacat atatattcct                    40

<210> SEQ ID NO 43
<211> LENGTH: 23
<212> TYPE: DNA
<213> ORGANISM: Artificial Sequence
<220> FEATURE:
<223> OTHER INFORMATION: Synthetic oligonucleotide: gm18: 2570 F_qPCR

<400> SEQUENCE: 43
tgagatgggt ggagctcaag aac                                      23

<210> SEQ ID NO 44
<211> LENGTH: 24
<212> TYPE: DNA
<213> ORGANISM: Artificial Sequence
<220> FEATURE:
<223> OTHER INFORMATION: Synthetic oligonucleotide: gm18: 2570 R_qPCR

<400> SEQUENCE: 44
agcttcatct gattgtgaca gtgc                                     24

<210> SEQ ID NO 45
<211> LENGTH: 24
<212> TYPE: DNA
```

```
<213> ORGANISM: Artificial Sequence
<220> FEATURE:
<223> OTHER INFORMATION: Synthetic oligonucleotide: gm18: 2580 F_qPCR

<400> SEQUENCE: 45
cgtgtagagt ccttgaagta cagc                                          24

<210> SEQ ID NO 46
<211> LENGTH: 22
<212> TYPE: DNA
<213> ORGANISM: Artificial Sequence
<220> FEATURE:
<223> OTHER INFORMATION: Synthetic oligonucleotide: gm18: 2580 R_qPCR

<400> SEQUENCE: 46
accagagctg tgatagccaa cc                                            22

<210> SEQ ID NO 47
<211> LENGTH: 22
<212> TYPE: DNA
<213> ORGANISM: Artificial Sequence
<220> FEATURE:
<223> OTHER INFORMATION: Synthetic oligonucleotide: gm18: 2590 F_qPCR

<400> SEQUENCE: 47
tcgccaaatc atgggacaag gc                                            22

<210> SEQ ID NO 48
<211> LENGTH: 22
<212> TYPE: DNA
<213> ORGANISM: Artificial Sequence
<220> FEATURE:
<223> OTHER INFORMATION: Synthetic oligonucleotide: gm18: 2590 R_qPCR

<400> SEQUENCE: 48
caatgtgcag catcgacatg gg                                            22

<210> SEQ ID NO 49
<211> LENGTH: 24
<212> TYPE: DNA
<213> ORGANISM: Artificial Sequence
<220> FEATURE:
<223> OTHER INFORMATION: Synthetic oligonucleotide: gm18: 2600 F_qPCR

<400> SEQUENCE: 49
gcttcagtca agaaaatgtg catg                                          24

<210> SEQ ID NO 50
<211> LENGTH: 23
<212> TYPE: DNA
<213> ORGANISM: Artificial Sequence
<220> FEATURE:
<223> OTHER INFORMATION: Synthetic oligonucleotide: gm18: 2600 R_qPCR

<400> SEQUENCE: 50
cacccgaaac cgcgacacaa atg                                           23

<210> SEQ ID NO 51
<211> LENGTH: 19
<212> TYPE: DNA
<213> ORGANISM: Artificial Sequence
<220> FEATURE:
<223> OTHER INFORMATION: Synthetic oligonucleotide: gm18: 2610 F_qPCR

<400> SEQUENCE: 51
aggtcacgtg ttgccgttg                                                19
```

```
<210> SEQ ID NO 52
<211> LENGTH: 27
<212> TYPE: DNA
<213> ORGANISM: Artificial Sequence
<220> FEATURE:
<223> OTHER INFORMATION: Synthetic oligonucleotide: gm18: 2610 R_qPCR

<400> SEQUENCE: 52
aaaccacacc aataacaaca aagctct                                          27

<210> SEQ ID NO 53
<211> LENGTH: 22
<212> TYPE: DNA
<213> ORGANISM: Artificial Sequence
<220> FEATURE:
<223> OTHER INFORMATION: Synthetic oligonucleotide: gm18: 2620 F_qPCR

<400> SEQUENCE: 53
aagcccaaca ggccaaagag ag                                               22

<210> SEQ ID NO 54
<211> LENGTH: 22
<212> TYPE: DNA
<213> ORGANISM: Artificial Sequence
<220> FEATURE:
<223> OTHER INFORMATION: Synthetic oligonucleotide: gm18: 2620 R_qPCR

<400> SEQUENCE: 54
acaccaaatg ggttcgcact tc                                               22

<210> SEQ ID NO 55
<211> LENGTH: 24
<212> TYPE: DNA
<213> ORGANISM: Artificial Sequence
<220> FEATURE:
<223> OTHER INFORMATION: Synthetic oligonucleotide: gm18: 2630 F_qPCR

<400> SEQUENCE: 55
ttgtggaagt gaaagtcggt ttgc                                             24

<210> SEQ ID NO 56
<211> LENGTH: 24
<212> TYPE: DNA
<213> ORGANISM: Artificial Sequence
<220> FEATURE:
<223> OTHER INFORMATION: Synthetic oligonucleotide: gm18: 2630 R_qPCR

<400> SEQUENCE: 56
gttgtcacgt ttcccgtaac aatg                                             24

<210> SEQ ID NO 57
<211> LENGTH: 24
<212> TYPE: DNA
<213> ORGANISM: Artificial Sequence
<220> FEATURE:
<223> OTHER INFORMATION: Synthetic oligonucleotide: EF1b_For.qRT

<400> SEQUENCE: 57
ccactgctga agaagatgat gatg                                             24

<210> SEQ ID NO 58
<211> LENGTH: 22
<212> TYPE: DNA
<213> ORGANISM: Artificial Sequence
<220> FEATURE:
```

<223> OTHER INFORMATION: Synthetic oligonucleotide: EF1b_Rev.qRT

<400> SEQUENCE: 58
aaggacagaa gacttgccac tc                                              22

<210> SEQ ID NO 59
<211> LENGTH: 21
<212> TYPE: DNA
<213> ORGANISM: Artificial Sequence
<220> FEATURE:
<223> OTHER INFORMATION: Synthetic oligonucleotide: SKIP16_For.qRT

<400> SEQUENCE: 59
gagcccaaga cattgcgaga g                                               21

<210> SEQ ID NO 60
<211> LENGTH: 21
<212> TYPE: DNA
<213> ORGANISM: Artificial Sequence
<220> FEATURE:
<223> OTHER INFORMATION: Synthetic oligonucleotide: SKIP16_Rev.qRT

<400> SEQUENCE: 60
cggaagcgga agaactgaac c                                               21

<210> SEQ ID NO 61
<211> LENGTH: 21
<212> TYPE: DNA
<213> ORGANISM: Artificial Sequence
<220> FEATURE:
<223> OTHER INFORMATION: Synthetic oligonucleotide: UKN2_For.qRT

<400> SEQUENCE: 61
gcctctggat acctgctcaa g                                               21

<210> SEQ ID NO 62
<211> LENGTH: 22
<212> TYPE: DNA
<213> ORGANISM: Artificial Sequence
<220> FEATURE:
<223> OTHER INFORMATION: Synthetic oligonucleotide: UKN2_Rev.qRT

<400> SEQUENCE: 62
acctcctcct caaactcctc tg                                              22

<210> SEQ ID NO 63
<211> LENGTH: 24
<212> TYPE: DNA
<213> ORGANISM: Artificial Sequence
<220> FEATURE:
<223> OTHER INFORMATION: Synthetic oligonucleotide: ACT11_For.qPCR

<400> SEQUENCE: 63
atcttgactg agcgtggtta ttcc                                            24

<210> SEQ ID NO 64
<211> LENGTH: 19
<212> TYPE: DNA
<213> ORGANISM: Artificial Sequence
<220> FEATURE:
<223> OTHER INFORMATION: Synthetic oligonucleotide: ACT11_Rev.qPCR

<400> SEQUENCE: 64
gctggtcctg gctgtctcc                                                  19

```
<210> SEQ ID NO 65
<211> LENGTH: 21
<212> TYPE: DNA
<213> ORGANISM: Artificial Sequence
<220> FEATURE:
<223> OTHER INFORMATION: Synthetic oligonucleotide: UNK1_For.qPCR

<400> SEQUENCE: 65
tggtgctgcc gctatttact g                                              21

<210> SEQ ID NO 66
<211> LENGTH: 23
<212> TYPE: DNA
<213> ORGANISM: Artificial Sequence
<220> FEATURE:
<223> OTHER INFORMATION: Synthetic oligonucleotide: UNK1_Rev.qPCR

<400> SEQUENCE: 66
ggtggaagga actgctaaca atc                                            23

<210> SEQ ID NO 67
<211> LENGTH: 22
<212> TYPE: DNA
<213> ORGANISM: Artificial Sequence
<220> FEATURE:
<223> OTHER INFORMATION: Synthetic oligonucleotide: TIP41_For. qPCR

<400> SEQUENCE: 67
aggatgaact cgctgataat gg                                             22

<210> SEQ ID NO 68
<211> LENGTH: 22
<212> TYPE: DNA
<213> ORGANISM: Artificial Sequence
<220> FEATURE:
<223> OTHER INFORMATION: Synthetic oligonucleotide: TIP41_Rev.qPCR

<400> SEQUENCE: 68
cagaaacgca acagaagaaa cc                                             22

<210> SEQ ID NO 69
<211> LENGTH: 22
<212> TYPE: DNA
<213> ORGANISM: Artificial Sequence
<220> FEATURE:
<223> OTHER INFORMATION: Synthetic oligonucleotide: PR-1 (6790) F

<400> SEQUENCE: 69
tgcttggtca cctggaagtt gg                                             22

<210> SEQ ID NO 70
<211> LENGTH: 22
<212> TYPE: DNA
<213> ORGANISM: Artificial Sequence
<220> FEATURE:
<223> OTHER INFORMATION: Synthetic oligonucleotide: PR-1 (6790) R

<400> SEQUENCE: 70
aacttcctgc gagctgcgat ac                                             22

<210> SEQ ID NO 71
<211> LENGTH: 23
<212> TYPE: DNA
<213> ORGANISM: Artificial Sequence
<220> FEATURE:
<223> OTHER INFORMATION: Synthetic oligonucleotide: PR-1 (6800) F
```

<400> SEQUENCE: 71
agtcattgtg ggtgatcatg ctg                                    23

<210> SEQ ID NO 72
<211> LENGTH: 24
<212> TYPE: DNA
<213> ORGANISM: Artificial Sequence
<220> FEATURE:
<223> OTHER INFORMATION: Synthetic oligonucleotide: PR-1 (6800) R

<400> SEQUENCE: 72
gcagcgttgt gtgcattaac aaag                                   24

<210> SEQ ID NO 73
<211> LENGTH: 23
<212> TYPE: DNA
<213> ORGANISM: Artificial Sequence
<220> FEATURE:
<223> OTHER INFORMATION: Synthetic oligonucleotide: Ox2610-SalF2

<400> SEQUENCE: 73
gtcgacatgc gcatgctcac cgg                                    23

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide: P2610fused-R

<400> SEQUENCE: 74
tattgcgaga accaaaccgg                                        20

<210> SEQ ID NO 75
<211> LENGTH: 30
<212> TYPE: DNA
<213> ORGANISM: Artificial Sequence
<220> FEATURE:
<223> OTHER INFORMATION: Synthetic oligonucleotide: Ox2590Sal-F

<400> SEQUENCE: 75
gggtcgacat ggccgatcag ttatcgaagg                             30

<210> SEQ ID NO 76
<211> LENGTH: 26
<212> TYPE: DNA
<213> ORGANISM: Artificial Sequence
<220> FEATURE:
<223> OTHER INFORMATION: Synthetic oligonucleotide: Ox2590fused-R

<400> SEQUENCE: 76
agtaatagcc tcatgctgct caagtt                                 26

<210> SEQ ID NO 77
<211> LENGTH: 28
<212> TYPE: DNA
<213> ORGANISM: Artificial Sequence
<220> FEATURE:
<223> OTHER INFORMATION: Synthetic oligonucleotide: TerXba-R

<400> SEQUENCE: 77
actctagagc gcatgtcttg cgttgatg                               28

<210> SEQ ID NO 78
<211> LENGTH: 29

```
<212> TYPE: DNA
<213> ORGANISM: Artificial Sequence
<220> FEATURE:
<223> OTHER INFORMATION: Synthetic oligonucleotide: GmubiXba-F

<400> SEQUENCE: 78
gctctagagg gcccaatata acaacgacg                                      29

<210> SEQ ID NO 79
<211> LENGTH: 28
<212> TYPE: DNA
<213> ORGANISM: Artificial Sequence
<220> FEATURE:
<223> OTHER INFORMATION: Synthetic oligonucleotide: TerKpn-R

<400> SEQUENCE: 79
tcggtaccgc gcatgtcttg cgttgatg                                       28

<210> SEQ ID NO 80
<211> LENGTH: 48
<212> TYPE: DNA
<213> ORGANISM: Artificial Sequence
<220> FEATURE:
<223> OTHER INFORMATION: Synthetic oligonucleotide: PPA Linker_Top

<400> SEQUENCE: 80
gatgtcttaa ttaatatctg tgggcccact atggcgcgcc aatgtaaa                 48

<210> SEQ ID NO 81
<211> LENGTH: 56
<212> TYPE: DNA
<213> ORGANISM: Artificial Sequence
<220> FEATURE:
<223> OTHER INFORMATION: Synthetic oligonucleotide: PPA Linker_Bottom

<400> SEQUENCE: 81
agcttttaca ttggcgcgcc atagtgggcc cacagatatt aattaagaca tctgca        56

<210> SEQ ID NO 82
<211> LENGTH: 21
<212> TYPE: DNA
<213> ORGANISM: Artificial Sequence
<220> FEATURE:
<223> OTHER INFORMATION: Synthetic oligonucleotide: Ox2600-F

<400> SEQUENCE: 82
atggtttcgg ttgatgatgg g                                              21

<210> SEQ ID NO 83
<211> LENGTH: 24
<212> TYPE: DNA
<213> ORGANISM: Artificial Sequence
<220> FEATURE:
<223> OTHER INFORMATION: Synthetic oligonucleotide: Ox2600-R

<400> SEQUENCE: 83
tttttgtgca tataaggggt tcat                                           24

<210> SEQ ID NO 84
<211> LENGTH: 31
<212> TYPE: DNA
<213> ORGANISM: Artificial Sequence
<220> FEATURE:
<223> OTHER INFORMATION: Synthetic oligonucleotide: NosHind-F

<400> SEQUENCE: 84
```

<210> SEQ ID NO 85
<211> LENGTH: 43
<212> TYPE: DNA
<213> ORGANISM: Artificial Sequence
<220> FEATURE:
<223> OTHER INFORMATION: Synthetic oligonucleotide: Nos2600-R

<400> SEQUENCE: 85
cccatcatca accgaaacca tagatccggt gcagattatt tgg         43

<210> SEQ ID NO 86
<211> LENGTH: 43
<212> TYPE: DNA
<213> ORGANISM: Artificial Sequence
<220> FEATURE:
<223> OTHER INFORMATION: Synthetic oligonucleotide: Nos2600-F

<400> SEQUENCE: 86
ccaaataatc tgcaccggat ctatggtttc ggttgatgat ggg         43

<210> SEQ ID NO 87
<211> LENGTH: 30
<212> TYPE: DNA
<213> ORGANISM: Artificial Sequence
<220> FEATURE:
<223> OTHER INFORMATION: Synthetic oligonucleotide: NosAsc-R

<400> SEQUENCE: 87
tcggcgcgcc gcgcatgtct tgcgttgatg               30

<210> SEQ ID NO 88
<211> LENGTH: 16
<212> TYPE: DNA
<213> ORGANISM: Artificial Sequence
<220> FEATURE:
<223> OTHER INFORMATION: Synthetic oligonucleotide: Ox2580-F

<400> SEQUENCE: 88
atgtctccgg ccgccg                     16

<210> SEQ ID NO 89
<211> LENGTH: 31
<212> TYPE: DNA
<213> ORGANISM: Artificial Sequence
<220> FEATURE:
<223> OTHER INFORMATION: Synthetic oligonucleotide: Ox2580-R

<400> SEQUENCE: 89
tgacttgcta ctaaaagcat tatatatgtt g             31

<210> SEQ ID NO 90
<211> LENGTH: 33
<212> TYPE: DNA
<213> ORGANISM: Artificial Sequence
<220> FEATURE:
<223> OTHER INFORMATION: Synthetic oligonucleotide: NosAsc-F

<400> SEQUENCE: 90
caggcgcgcc gatcatgagc ggagaattaa ggg           33

<210> SEQ ID NO 91
<211> LENGTH: 38
<212> TYPE: DNA
<213> ORGANISM: Artificial Sequence

```
<220> FEATURE:
<223> OTHER INFORMATION: Synthetic oligonucleotide: Nos2580-R

<400> SEQUENCE: 91
cggcggccgg agacatagat ccggtgcaga ttatttgg                              38

<210> SEQ ID NO 92
<211> LENGTH: 38
<212> TYPE: DNA
<213> ORGANISM: Artificial Sequence
<220> FEATURE:
<223> OTHER INFORMATION: Synthetic oligonucleotide: Nos2580-F

<400> SEQUENCE: 92
ccaaataatc tgcaccggat ctatgtctcc ggccgccg                              38

<210> SEQ ID NO 93
<211> LENGTH: 30
<212> TYPE: DNA
<213> ORGANISM: Artificial Sequence
<220> FEATURE:
<223> OTHER INFORMATION: Synthetic oligonucleotide: NosSbf-R

<400> SEQUENCE: 93
tgcctgcagg gcgcatgtct tgcgttgatg                                       30

<210> SEQ ID NO 94
<211> LENGTH: 16
<212> TYPE: DNA
<213> ORGANISM: Artificial Sequence
<220> FEATURE:
<223> OTHER INFORMATION: Synthetic oligonucleotide: M13 F

<400> SEQUENCE: 94
gtaaaacgac ggccag                                                      16

<210> SEQ ID NO 95
<211> LENGTH: 17
<212> TYPE: DNA
<213> ORGANISM: Artificial Sequence
<220> FEATURE:
<223> OTHER INFORMATION: Synthetic oligonucleotide: M13 R

<400> SEQUENCE: 95
caggaaacag ctatgac                                                     17

<210> SEQ ID NO 96
<211> LENGTH: 21
<212> TYPE: DNA
<213> ORGANISM: Artificial Sequence
<220> FEATURE:
<223> OTHER INFORMATION: Synthetic oligonucleotide: pSM101 seq

<400> SEQUENCE: 96
gtcttgatga gacctgctgc g                                                21

<210> SEQ ID NO 97
<211> LENGTH: 37
<212> TYPE: DNA
<213> ORGANISM: Artificial Sequence
<220> FEATURE:
<223> OTHER INFORMATION: Synthetic oligonucleotide: g2590pHind-F

<400> SEQUENCE: 97
cttaagcttg aatggttttt gttttgttgt ctctcac                               37
```

```
<210> SEQ ID NO 98
<211> LENGTH: 23
<212> TYPE: DNA
<213> ORGANISM: Artificial Sequence
<220> FEATURE:
<223> OTHER INFORMATION: Synthetic oligonucleotide: g2590pSal-R

<400> SEQUENCE: 98
ttggtcgacc gtatcatcca atg                                          23

<210> SEQ ID NO 99
<211> LENGTH: 23
<212> TYPE: DNA
<213> ORGANISM: Artificial Sequence
<220> FEATURE:
<223> OTHER INFORMATION: Synthetic oligonucleotide: SCN_Res Bridge F

<400> SEQUENCE: 99
tttagcctgc tcctcacaaa ttc                                          23

<210> SEQ ID NO 100
<211> LENGTH: 23
<212> TYPE: DNA
<213> ORGANISM: Artificial Sequence
<220> FEATURE:
<223> OTHER INFORMATION: Synthetic oligonucleotide: SCN_Res Bridge R

<400> SEQUENCE: 100
ttggagaata tgctctcggt tgt                                          23

<210> SEQ ID NO 101
<211> LENGTH: 23
<212> TYPE: DNA
<213> ORGANISM: Artificial Sequence
<220> FEATURE:
<223> OTHER INFORMATION: Synthetic oligonucleotide: 2570F_qPCR

<400> SEQUENCE: 101
tgagatgggt ggagctcaag aac                                          23

<210> SEQ ID NO 102
<211> LENGTH: 23
<212> TYPE: DNA
<213> ORGANISM: Artificial Sequence
<220> FEATURE:
<223> OTHER INFORMATION: Synthetic oligonucleotide: 2570 UTR Rev

<400> SEQUENCE: 102
caagtactct tccccacaaa agc                                          23

<210> SEQ ID NO 103
<211> LENGTH: 21
<212> TYPE: DNA
<213> ORGANISM: Artificial Sequence
<220> FEATURE:
<223> OTHER INFORMATION: Synthetic oligonucleotide: 2570 put exon F

<400> SEQUENCE: 103
tgcagtttta gtggaaaggc c                                            21

<210> SEQ ID NO 104
<211> LENGTH: 23
<212> TYPE: DNA
<213> ORGANISM: Artificial Sequence
<220> FEATURE:
<223> OTHER INFORMATION: Synthetic oligonucleotide: 2570 exon 6 R
```

<400> SEQUENCE: 104
tcatcaagct caacttgaat ccc                                           23

<210> SEQ ID NO 105
<211> LENGTH: 28
<212> TYPE: DNA
<213> ORGANISM: Artificial Sequence
<220> FEATURE:
<223> OTHER INFORMATION: Synthetic oligonucleotide: 2590-5GSP

<400> SEQUENCE: 105
gatcggccat tttcctccga tcgaaaca                                      28

<210> SEQ ID NO 106
<211> LENGTH: 28
<212> TYPE: DNA
<213> ORGANISM: Artificial Sequence
<220> FEATURE:
<223> OTHER INFORMATION: Synthetic oligonucleotide: 2590-5NGSP

<400> SEQUENCE: 106
gacgaccaag tccaaatcca aaacccgc                                      28

<210> SEQ ID NO 107
<211> LENGTH: 28
<212> TYPE: DNA
<213> ORGANISM: Artificial Sequence
<220> FEATURE:
<223> OTHER INFORMATION: Synthetic oligonucleotide: 2590-3GSP

<400> SEQUENCE: 107
aagccaaaga acttgagcag catgaggc                                      28

<210> SEQ ID NO 108
<211> LENGTH: 28
<212> TYPE: DNA
<213> ORGANISM: Artificial Sequence
<220> FEATURE:
<223> OTHER INFORMATION: Synthetic oligonucleotide: 2590-3NGSP

<400> SEQUENCE: 108
ctgtccagtt gttcgtctta cacatcca                                      28

<210> SEQ ID NO 109
<211> LENGTH: 24
<212> TYPE: DNA
<213> ORGANISM: Artificial Sequence
<220> FEATURE:
<223> OTHER INFORMATION: Synthetic oligonucleotide: 2610-5GSP

<400> SEQUENCE: 109
ggcgacgatc ttgacgacgg cgtt                                          24

<210> SEQ ID NO 110
<211> LENGTH: 25
<212> TYPE: DNA
<213> ORGANISM: Artificial Sequence
<220> FEATURE:
<223> OTHER INFORMATION: Synthetic oligonucleotide: 2610-5NGSP

<400> SEQUENCE: 110
tcatacagtg caaccaccag ccgcg                                         25

<210> SEQ ID NO 111

```
<211> LENGTH: 26
<212> TYPE: DNA
<213> ORGANISM: Artificial Sequence
<220> FEATURE:
<223> OTHER INFORMATION: Synthetic oligonucleotide: 2610-3GSP

<400> SEQUENCE: 111
ggacgaggtc acgtgttgcc gttgct                                          26

<210> SEQ ID NO 112
<211> LENGTH: 28
<212> TYPE: DNA
<213> ORGANISM: Artificial Sequence
<220> FEATURE:
<223> OTHER INFORMATION: Synthetic oligonucleotide: 2610-3NGSP

<400> SEQUENCE: 112
ttcaccacta tgggcgtatt caggtggt                                        28

<210> SEQ ID NO 113
<211> LENGTH: 23
<212> TYPE: DNA
<213> ORGANISM: Artificial Sequence
<220> FEATURE:
<223> OTHER INFORMATION: Synthetic oligonucleotide: 2580-3GSP

<400> SEQUENCE: 113
cctgggggat tccaaaggaa cgc                                             23
```

RHG1 MEDIATED RESISTANCE TO SOYBEAN CYST NEMATODE

CROSS-REFERENCE TO RELATED APPLICATIONS

This patent application claims the benefit of priority of U.S. Provisional Patent Application No. 61/646,017, filed May 11, 2012 and U.S. Provisional Patent Application No. 61/676,854, filed Jul. 27, 2012, which are both incorporated herein by reference in their entirety.

REFERENCE TO SEQUENCE LISTING

This application includes an electronically submitted Sequence Listing in .txt format. The .txt file contains a sequence listing entitled "2020.11.09 15-674-US_Sequence_ Listing_ST25.txt" created on Nov. 9, 2020, and is 44.6 kilobytes in size. The Sequence Listing contained in this .txt file is part of the specification and is hereby incorporated by reference herein in its entirety.

STATEMENT REGARDING FEDERALLY SPONSORED RESEARCH

This invention was made with government support under grant numbers 06-CRHF-0-6055 and 10-CRHF-0-6055 awarded by USDA/NIFA. The government has certain rights in the invention.

BACKGROUND

Soybean cyst nematode (SCN) is currently the most economically damaging disease for United States soybean production in most years. Estimates suggest that SCN accounts for over $700 million in reduced soybean production in the United States annually. SCN also seriously impacts soybean production in other countries such as Brazil, Argentina and China. Soybean varieties with increased resistance to SCN have been identified, but resistance is quantitative and efficacy varies depending on nematode genotypes, hence use of the more resistant varieties still can result in soybean yield loss due to SCN.

The genetic basis for resistance to SCN has been partially defined, to the level of genetic loci, and appropriate sources of the soybean locus Rhg1 make substantial contributions to SCN resistance. Prior to the present work, the specific genes and gene products controlling Rhg1-mediated SCN resistance have not been successfully documented.

SUMMARY

Methods of increasing resistance of a plant to nematodes, in particular increasing resistance of soybeans to SCN are provided herein. Several gene products from the rhg1-b locus are identified and the relationship of the gene products to resistance to SCN in soybeans is demonstrated.

In one aspect, methods of increasing resistance of a plant to nematodes, suitably cyst-forming nematodes, suitably SCN by increasing the expression of or altering the expression pattern or gene copy number of a polynucleotide encoding a Glyma18g02580 polypeptide, a Glyma18g02590 polypeptide, a Glyma18g02610 polypeptide, a polypeptide having 90% or more identity to SEQ ID NO: 1, SEQ ID NO: 2, SEQ ID NO: 5, SEQ ID NO: 6, or SEQ ID NO: 3, or a homolog or functional variant of any of the aforementioned polypeptides in cells of the plant are provided. Use of combinations of the polypeptides is envisioned. The polynucleotides encoding these polypeptide sequences may be derived from the Williams 82, PI88788 or Peking (PI 548402) soybean varieties or other sources of the polynucleotides. The poly peptide sequences are provided and the polymorphisms between the sequences in different varieties are noted. Increased expression of the polynucleotides in cells of the plant increases the resistance of the plant to nematodes. Suitably expression is increased in cells of the root of the plant. Suitably expression of at least two of the polynucleotides is increased. Suitably, expression of all three of the polynucleotides is increased.

In another aspect, methods of increasing resistance of a plant to nematodes, suitably cyst-forming nematodes, suitably SCN by altering (increasing or decreasing) the expression in cells in the root of the plant of a polypeptide identical or similar to at least a portion of SEQ ID NO: 1 of Glyma18g02580, SEQ ID NO: 2, 5 or 6 of Glyma18g02590 or SEQ ID NO: 3 of Glyma18g02610 relative to the expression in cells in the root of the plant of a polypeptide whose expression can be used as a control, such as Glyma11g35820, are provided. Suitably expression of at least two of the polypeptides is increased. Suitably, expression of all three of the polypeptides is increased. Alternatively or in addition, expression of the polynucleotides encoding the polypeptides of Glyma18g02610, Glyma18g02590, and/or Glyma18g2580 may be increased as well.

In another aspect, methods of identifying plants that exhibit useful levels of resistance of a plant to nematodes suitably cyst-forming nematodes, suitably SCN by identifying plants that exhibit altered (increased or decreased) expression in cells in the root of the plant of a polypeptide identical or similar to at least a portion of SEQ ID NO: 1 of Glyma18g02580, SEQ ID NO: 2, 5 or 6 of Glyma18g02590 or SEQ ID NO: 3 of Glyma18g02610 relative to the expression in cells in the root of the plant of a polypeptide whose expression can be used as a control, such as Glyma11g35820, are provided. Suitably expression of at least two of the polypeptides is at a higher level than in plants that are more susceptible to SCN. Suitably, expression of all three of the polypeptides is at a higher level. Alternatively or in addition, expression of the polynucleotides encoding the polypeptides Glyma18g02610, Glyma18g02590, and/or Glyma18g2580 may be at a higher level as well.

In yet another aspect, a construct comprising a promoter operably linked to a polynucleotide encoding at least a portion of Glyma18g02580 polypeptide comprising SEQ ID NO: 1, a Glyma18g02590 polypeptide comprising SEQ ID NO: 2, 5 or 6, a Glyma18g02610 polypeptide comprising SEQ ID NO: 3 or a polypeptide having at least 90% identity to SEQ ID NO: 1, SEQ ID NO: 2, SEQ ID NO: 3, SEQ ID NO: 5, SEQ ID NO: 6 or a homolog or functional portion of any of the aforementioned polypeptides or combinations thereof is provided. The construct may be used to generate transgenic plants or seeds.

In still another aspect, a transgenic plant comprising an exogenous or non-native polynucleotide encoding at least a portion of Glyma18g02580 polypeptide comprising SEQ ID NO: 1, Glyma18g02590 polypeptide comprising SEQ ID NO: 2, 5 or 6, Glyma18g02600 polypeptide comprising SEQ ID NO: 4, Glyma18g02610 polypeptide comprising SEQ ID NO: 3 or a polypeptide having at least 90% identity to SEQ ID NO: 1, SEQ ID NO: 2, SEQ ID NO: 3, SEQ ID NO: 4, SEQ ID NO: 5, SEQ ID NO: 6, a homolog or a functional portion of any of the aforementioned polypeptides or combinations thereof or the polypeptides described herein from either the PI88788 or Peking-source is provided. The transgenic plant has increased resistance to nematodes, suitably cyst-forming nematodes, suitably SCN. Suitably, the transgenic plant comprises at least one polynucleotide encoding at least two or at least three of the polynucleotides encoding the Glyma18g02580, Glyma18g02590, and Glyma18g02610 polypeptides.

In a further aspect, a transgenic cell comprising a polynucleotide encoding a polypeptide capable of increasing resistance to nematodes, suitably cyst-forming nematodes, suitably SCN is provided. The polypeptide includes at least a portion of a polypeptide having at least 90% identity to SEQ ID NO: 1, SEQ ID NO: 2, SEQ ID NO: 3 or similar sequences derived from PI88788 (such as SEQ ID NO: 5) or Peking-source (such as SEQ ID NO: 6) or combinations thereof. Suitably, the polynucleotide includes at least two or three of the polypeptides having at least 90% identity to SEQ ID NO: 1, SEQ ID NO: 2, SEQ ID NO: 3.

In another aspect, methods of generating a transgenic plant by introducing an exogenous polynucleotide encoding at least a portion of a Glyma18g02580 polypeptide having at least 90% identity to SEQ ID NO: 1, Glyma18g02590 polypeptide having at least 90% identity to SEQ ID NO: 2, 5 or 6, or Glyma18g02610 polypeptide having at least 90% identity to SEQ ID NO: 3, or homologs or combinations thereof are provided. The transgenic plant has increased expression of Glyma18g02610, Glyma18g02590, and/or Glyma18g02580 in a cell in a root of the plant. The transgenic plant has increased resistance to nematodes, suitably cyst-forming nematodes, suitably SCN, as compared to a control plant. Suitably, the transgenic plant has increased expression of at least two of the polynucleotides or all three of the polynucleotides encoding the Glyma18g02610, Glyma18g02590, and/or Glyma18g02580 polypeptides.

In yet a further aspect, methods of identifying molecules that interact with the Rhg1 locus, Glyma18g02610, Glyma18g02590 and/or Glyma18g02580 RNA transcripts, or the Glyma18g02610, Glyma18g02590 and/or Glyma18g02580 polypeptide are provided. The methods include detecting molecules capable of binding the Rhg1 locus, Glyma18g02610, Glyma18g02590 or Glyma18g02580 RNA transcripts, or Glyma18g02610, Glyma18g02590 or Glyma18g02580 polypeptides.

In a still further aspect, methods of identifying the resistance or susceptibility phenotype of a plant to cyst nematodes are provided. The method includes detecting a genetic marker associated with cyst nematode resistance or susceptibility in a first plant cell and comparing the genetic marker in the first plant cell to the genetic marker in a second plant cell with a known resistance or susceptibility phenotype or a control plant cell. The genetic marker may be sequence variations, methylation differences, mRNA expression differences or other differences identified herein. Suitably, the genetic marker is associated with characteristics of the Rhg-1 locus, such as those reported herein. Suitably, the genetic marker is the genomic copy number of at least one of Glyma18g02600, Glyma18g02610, Glyma18g02590 or Glyma18g02580. Suitably the plant is a soybean and the nematodes are SCN.

In still a further aspect, methods of increasing resistance of a plant to nematodes comprising expressing a polynucleotide encoding a Glyma18g02610 polypeptide, a Glyma18g02590 polypeptide, or a Glyma18g02580 polypeptide, a polypeptide having 90% or more identity to SEQ ID NO: 1, SEQ ID NO: 2, SEQ ID NO: 5, SEQ ID NO: 6 or SEQ ID NO: 3, or a homolog or functional variant or combinations of any of the aforementioned polypeptides in a cell. Suitably, the polynucleotide encodes at least two or all three of the Glyma18g02610, Glyma18g02590 or Glyma18g02580 polypeptides. The polypeptides or a cell encoding the polypeptide may then be applied to the plant, seeds of the plant or to soil in which the seeds may be planted. The application increases the resistance of the plant to nematodes.

BRIEF DESCRIPTION OF THE DRAWINGS

FIG. 2 is a pictorial depiction of one gene silencing strategy that uses artificial microRNA sequences to target a gene of interest.

FIG. 3A is a photograph showing representative SCN-infested roots; root vascular cylinder and nematodes stained with acid fuchsin. Fewer nematodes progress from J2 to J3, J4, adult male or egg-filled adult female (cyst) stages in SCN-resistant roots. FIG. 3B is a graph showing that SCN development beyond J2 stage in transgenic roots of soybean variety Fayette with the designated gene silenced, relative to Williams 82 (SCN-susceptible) and non-silenced Fayette (SCN-resistant) controls. Mean±std. error of mean. *: Fayette (silenced) significantly different from Fayette (not silenced) based on ANOVA $p<0.05$. EV: transformed with empty vector.

FIGS. 4A and 4C show that nematode development on Williams 82 and Fayette roots transformed with empty vector (EV), or Fayette transformed with silencing constructs (2580RNAi or ami2590) was dependent on level of silencing. Transgenic roots with reduced target transcript abundance (+) displayed nematode development similar to Williams 82 (SCN-susceptible), while transgenic roots with non-silenced transcript level (−) had nematode development similar to Fayette (SCN-resistant). FIGS. 4B and 4D show the transcript abundance of target genes in roots from (A) or (C) respectively, measured by qPCR. SKP16 transcript used as reference and normalized to Fayette-EV. The results of FIGS. 4B and 4D were used to place roots in the 'well-silenced' (+) or 'not well-silenced' (−) categories shown in FIGS. 4A and 4C. FIGS. 4A and 4B are Glyma18g02580, FIGS. 4C and 4D are Glyma18g02610. Bars represent mean±std. error of mean.

FIG. 5A-5D show a 31.2 kb repeat that elevates expression of the encoded genes is present in SCN-resistant haplotypes of the Rhg1 locus. FIG. 5A is a schematic of Rhg1 locus of Williams 82 (top), and five fosmid inserts from rhg1-b haplotype. DNA sequences of soybean reference genome shown for the two designated locations. Numbers and block icons refer to soybean genes (e.g., Glyma18g02540). Fosmids #3, 4 and 5 carry rhg1-b genome segments that span repeat junctions. FIG. 5B shows the Rhg1 repeat junction sequence from four different sources of SCN resistance (compare to reference genome sequences in (FIG. 5A)). FIG. 5C is a graph showing the number of whole-genome shotgun sequencing reads corresponding to reference genome region shown in green in FIG. 5A was ten-fold greater than for genome regions adjacent to rhg1-b on chromosome 18 or for Rhg1-homeologous loci on chromosomes 11 and 2. FIG. 5D is a graph showing transcript abundance of genes encoded in the 31 kb repeat region is much greater in roots from SCN-resistant soybean varieties relative to SCN-susceptible varieties. Mean±std. error of mean shown for qPCR; results for Glyma18g02600 were at limit of detection.

FIG. 6A is a schematic showing the two adjacent probes isolated from a single PI88788 (rhg1-b) genomic DNA fosmid clone whose insert spans a repeat junction, generating a 25.2 kb probe (green label) and an adjacent 9.7 kb probe (red label). DNA for green-labeled and red-labeled fiber-FISH probes are shown under the corresponding sequence regions of Williams 82. The 25.2 kb fragment from rhg1-b haplotype used for green probe was a single continuous DNA fragment that spans a repeat junction. FIG. 6B shows a composite of four Fiber-FISH images (four DNA fibers) per genotype, and probe diagram. Alternating pattern of red and green hybridization on single genomic DNA fibers indicates ten and three direct repeat copies of the 31 kb block at Rhg1 locus of SCN-resistant Fayette (rhg1-b derived from PI 88788) and Peking (PI 548402) respectively, and one copy per Rhg1 haplotype SCN-susceptible Williams 82. White bars=10 µm, which correspond to approximately 32 kb using a 3.21 kb/µm conversion rate.

FIG. 7A-7E show that multiple SCN-resistant varieties contain the DNA junction indicative of a repeat within the Rhg1 locus, and exhibit elevated expression of genes fully encoded within the repeat. FIG. 7A is a schematic of PCR primers used in FIG. 7B (see also FIG. 5). FIG. 7B is a photograph of a gel showing the results of PCR using outward-directed oligonucleotide primers shown in FIG. 7A that match sequences at the outer edges of the 31 kb segment of Rhg1 locus that is repeated in some soybean varieties. R indicates SCN-resistant and S indicates SCN-susceptible soybean variety. For primers 81 and 82 see Table 4. FIG. 7C shows the DNA Sequence from 11 SCN-resistant varieties and reveals identical sequence (SEQ ID NO: 15) for the repeat junction indicating a shared origin. Red bar indicates repeat junction (see also FIG. 5). FIG. 7D is a graph showing the transcript abundance for genes encoded at Rhg1 (normalized to SKP16), revealing elevated expression of genes fully encoded within the repeats of Rhg1 from PI 88788 or Peking sources, relative to expression of the same genes in SCN-susceptible varieties. Bars represent mean±std. error of mean. Glyma18g02600 is expressed below 0.01% of SKP16 (CT>35 cycles). FIG. 7E is an RNA blot analysis for Glyma18g02570 using RNA collected from roots of whole plants of Fayette and Forrest (SCN resistant) and Williams 82 (SCN susceptible). * denotes the band corresponding to the expected transcript size of Glyma18g02570 (1.2 kb). The band at 1.8 kb corresponds to non-specific ribosomal binding. Cultivars Fayette and Forrest (that contain repeats of the 31 kb DNA segment) display the same banding pattern as Williams 82 (that contains a single copy of the 31 kb DNA segment); no alternative transcripts for Glyma18g02570 were detected as a result of the repeated DNA in Fayette and Forrest. RACE PCR from plants carrying rhg1-b confirmed full-length transcripts (with transcript ends as annotated in the reference genome) for Glyma18g02580, -2590 and -2610.

FIG. 12A-12H is a set of photographs showing the histochemical staining of promoter-GUS expression in Fayette hairy root with (FIGS. 12B, 12D, 12F and 12H) or without (FIGS. 12A, 12C, 12E, and 12G) nematode inoculation. FIGS. 12A and 12B show Glyma18g02580. FIGS. 12C and 12D show Glyma18g02590. FIGS. 12E and 12F show Glyma18g02610. FIGS. 12G and 12H show Glyma14g06080.

FIG. 13 provides the nucleotide and amino acid sequences for Glyma18g2590 from the indicated varieties.

FIG. 14 is a computer generated schematic of the three-dimensional structure of Glyma18g2590 showing the polymorphisms among the varieties in the structure.

FIG. 16A is a graph showing similar nematode development on transgenic roots of Williams 82 expressing empty vector (EV) or Williams 82 expressing the Fayette (rhg1-b-type) allele of Glyma18g02590 under control of Fayette Glyma18g02590 promoter sequences ($2590_{FayP}$::$2590_{Fay}$). Williams 82 transformed with either construct allowed a greater proportion of nematodes to advance beyond the J2 stage compared to Fayette-EV. FIG. 16B is a graph showing transcript abundance for Glyma18g02590 in roots from FIG. 16A, measured by qPCR. SKR16 transcript used as reference; data normalized to Williams 82-EV. Bars in FIG. 16A and FIG. 16B represent mean±std. error of mean.

Table 1 provides the length estimates for the Fiber-FISH hybridization signals.

Table 2 provides the gene copy number of the Phg1 locus in various soybean varieties.

Table 3 provides the amino acid polymorphisms within the 31 sib repeat at rhg1-b.

Table 4 provides the DNA sequences of the oligonucleotide primers used for PCR.

Table 5 provides the amino acid sequences for Glyma18g2580, Glyma18g2590, Glyma18g2600, and Glyma18g2610.

DETAILED DESCRIPTION

Methods of identifying plants resistant or susceptible to cyst nematodes, such as the soybean cyst nematode (SCN), methods of assessing a plant's level of resistance or susceptibility to SCN, methods of increasing resistance of a plant or plant cells to cyst nematodes and methods of generating transgenic plant materials, including transgenic cells and plants, are provided herein. In addition, constructs including polynucleotides encoding the Rhg1 polypeptides described herein or homologs or variants thereof are provided herein as SEQ ID NO: 1-6. Transgenic plants or transgenic plant cells with increased resistance to cyst nematodes, particularly SCN, carrying a transgene encoding a non-native or exogenous Rhg1 derived polynucleotide encoding the polypeptides of SEQ ID NOs: 1-6 are provided herein. Non-transgenic plants carrying the polypeptides or bred or otherwise engineered to express increased levels of the polypeptides or the polynucleotides encoding the polypeptides are also disclosed.

Figure 1:
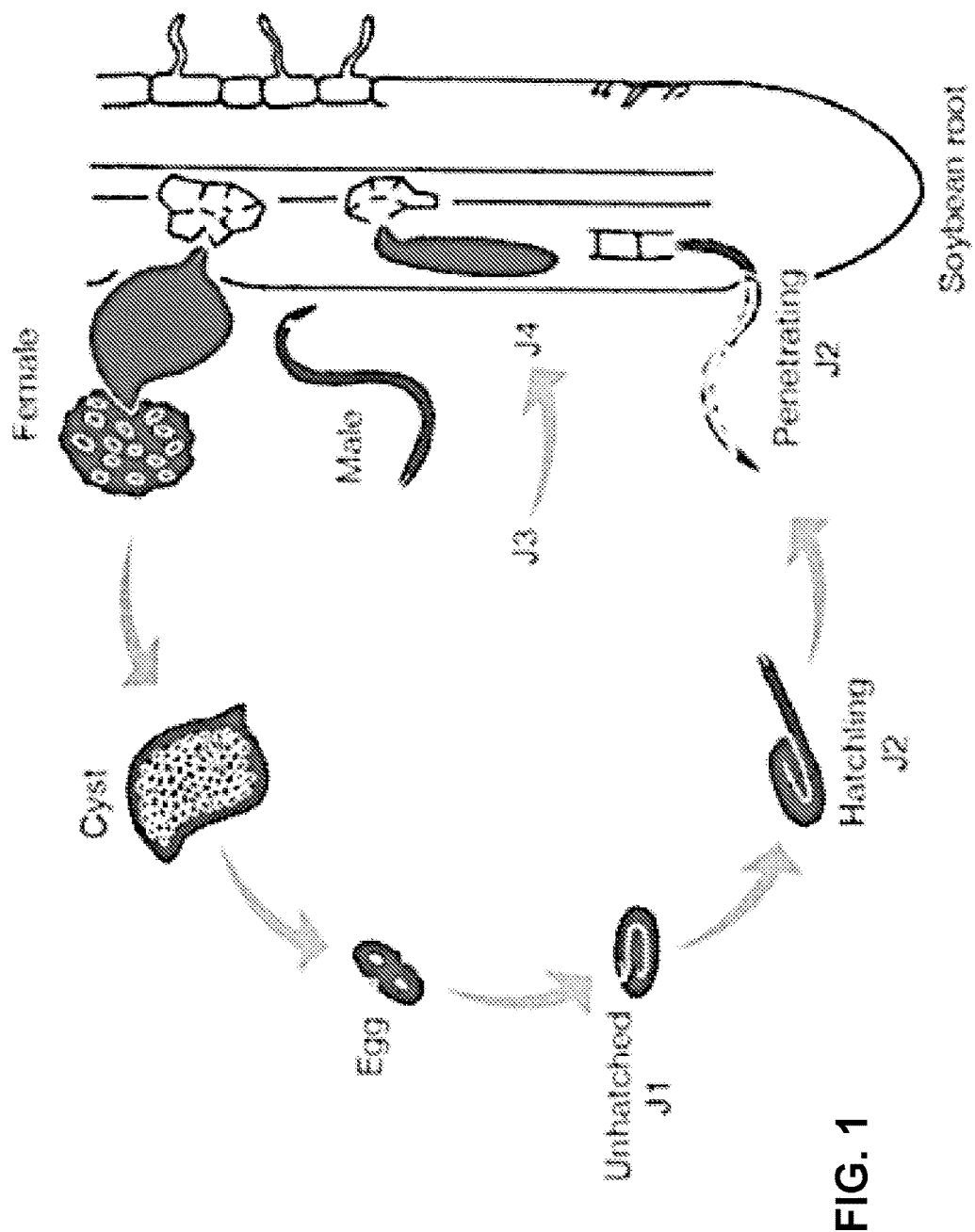
FIG. 1 is a pictorial depiction of the lifecycle of SCN.

SCN is caused by the nematode *Heterodera glycines*. The life cycle of the nematode is shown in FIG. 1. Once afield is infested with this nematode, no economically feasible means of eliminating SCN from that field presently exists. Current management of SCN often focuses on crop rotation and planting SCN-resistant varieties of soybeans to control *H. glycines* populations across multiple years, as well as use of SCN-resistant and/or SCN-tolerant soybeans to facilitate acceptable yield of the present year's crop. Practitioners have adopted "Race" and "Hg Type" terminologies to describe *H. glycines* populations according to their ability to overcome known sources of plant SCN-resistance. Several races and Hg Types exist and soybean resistance to one type may offer little to no protection against another type of the nematode. In addition, *H. glycines* are outcrossing organisms for which local populations are genetically heterogeneous (and new nematode genotypes can be introduced), hence local populations can undergo shifts in race or Hg Type such that previously effective plant SCN resistance can lose efficacy. Thus, the ability to identify which soybeans are resistant to which *H. glycines* nematode populations and the further ability to genetically engineer soybean plants with increased resistance to more than one type of nematode population is needed.

Soybeans with increased resistance to SCN are available and have been used in cross-breeding experiments to generate soybeans that are more resistant to SCN. The soybean rhg1 locus of Peking was previously identified, mapped to a region of chromosome 18 (formerly known as linkage group G), and a gene at that locus encoding a product carrying leucine-rich repeats and a protein kinase domain (LRR-kinase) was hypothesized to account for the increased resistant to SCN. In plants carrying the rhg1-b locus derived from soybean PI88788, SCN still penetrate and initiate feeding, but a high percentage of the syncitia do not persist and undergo the full sequence of nematode development (molting through the J3 and I4 stages to adulthood, sexual fertilization, and female transition to an embryo-filled and environmentally persistent cyst) (Li, Chen et al. 2004), (Colgrove and Niblack 2008). The molecular basis of this partial SCN-resistance is not understood. Despite 50 years of research on SCN, a pathogen causing hundreds of millions of dollars of economic losses in the U.S. annually, there were no confirmed public reports of a cloned soybean SCN resistance gene prior to the priority application.

Further fine genetic mapping of the rhg1 locus, which is also known as the Rhg1 locus, or by other more restricted designations such as rhg1-b, was completed in plants carrying the PI88788 source of Rhg1, and new markers associated with the resistance genotype were identified. See Kim, M., D. L. Hyten, A. F. Bent and B. W. Diers, 2010. Fine mapping of the SCN resistance locus rhg1-b from PI 88788. Plant Genome 3:81-89, which is incorporated herein by reference in its entirety. PI88788 was chosen because it is the source of resistance in many cross-bred lines currently marketed as resistant to SCN. These markers are tightly linked with resistance or susceptibility to SCN and may be useful to identify or predict whether soybean breeding lines are likely to display a SCN-resistant or SCN-sensitive phenotype. The refined map of the rhg1-b locus from PI88788 suggested that the LRR-kinase gene that is very close to the rhg1-b locus does not make significant contributions to the SCN resistance phenotype. The study of Melito et al. 2010, which used transgenic roots expressing full-length transcripts or constructs that partially silence the expression of transcripts, also found no evidence to support a role for the rhg1-b-proximal Glyma18g02680 LRR-kinase SCN resistance. Kim et al. demonstrated that the rhg1-b genetic components associated with the SCN resistance/susceptibility phenotype of PI88788 and its derivatives are located within the chromosomal interval defined by the termini BARCSOYSSR_18_0090 and BARCSOYSSR_18_0094. The most recent fine-structure genetic mapping defined an interval for rhg1-b that corresponds to a 67 kb interval carrying 11 predicted genes in the sequenced genome of SCN-susceptible Williams 82 soybean (Kim, Hyten et al. 2010). See FIG. 5.

Here we report the identification and functional testing of multiple genes in the rhg1-b genetic interval. Within the Rhg1 locus, multiple copies (ten, seven or three copies in the varieties investigated to date) of a chromosome segment encoding four identified genes within the Rhg1 locus are present in SCN-resistant soybean varieties, while only one copy of this segment is present in the tested SCN-susceptible varieties that lack Rhg1 alleles derived from the resistant varieties such as PI88788, PI437654 or Peking. See FIGS. 5 and 6. Silencing of any one of three genes within the multi-copy gene block using miRNA leads to increased susceptibility to SCN in transgenic soybean roots. In transgenic roots from a previously SCN-susceptible soybean variety, simultaneous overexpression of three or four of the rhg1-b genes from the multi-copy gene block leads to increased SCN resistance. The genes within this block are expressed at significantly higher levels in the tested SCN-resistant soybean varieties. Trans-acting factors in Fayette also are not sufficient to drive the elevated expression of transgenic DNAs sequences carrying these ~2 kb of Glyma18g02590 or Glyma18g02610 promoter DNA sequence, when those sequences are integrated at loci other than rhg1-b in Fayette. DNA methylation at multiple sites within the Rhg1 locus is polymorphic between SCN-resistant and SCN-susceptible lines, and this may contribute to the gene expression differences that correlate with SCN resistance. The number of copies of this locus also correlates to the levels of expression of the Glyma18g2580, Glyma18g2590 and Glyma18g2610 polypeptides and mRNAs and to the level of resistance to SCN. Thus gene dosing based on increasing the number of copies of the repeated region of the DNA may be a key factor mediating increased expression of the polypeptides and increased resistance to SCN. Many portions of these findings were reported in Cook, D. E., Lee, T. G., Guo, X., Melito, S., Wang, K., Bayless, A., Wang, J., Hughes, T. J., Willis, D. K., Clemente, T., Diers, B. W., Hudson, M. E. and Bent, A. F. 2012. Copy Number Variation of Multiple Genes at Rhg1 Mediates Nematode Resistance in Soybean. Science 338: 1206-1209 and the associated Supporting Online Material (Supplementary materials), which are incorporated herein by reference in their entirety.

The resistance or susceptibility phenotype of a plant can be predicted with valuable accuracy by comparing a genetic marker in the plant to the same genetic marker or selectable marker in a second plant with known resistance or susceptibility phenotype. Thus methods of screening a first plant or plant cell for resistance or susceptibility to cyst nematodes is provided herein. The methods include detecting a genetic or selectable marker associated with cyst nematode resistance or susceptibility to cyst nematodes in the first plant cell and using that marker to predict the resistance or susceptibility of the first plant or plant cell to nematodes. Prediction does not mean a 100% guarantee of the phenotype regarding resistance or susceptibility of the plant to cyst nematodes. The predicting step may include comparing the marker in the first plant or plant cell to the marker in a second plant or plant cell with a known resistance or susceptibility phenotype. The marker phenotype or genotype of the second cell is predictive of the cyst nematode resistance phenotype in the first cell. The prediction may be used to select resistant soybeans or resistant plant cells for use in generating resistant soybean lines.

A plant includes any portion of the plant including but not limited to a whole, plant, a portion of a plant such as a part of a root, leaf, stem, seed, pod, flower, cell, tissue or plant germplasm or any progeny thereof. Germplasm refers to genetic material from an individual or group of individuals or a clone derived from a line, cultivar, variety or culture. Soybean plant refers to whole soybean plant or portions thereof including, but not limited to, soybean plant cells, soybean plant protoplasts, soybean plant tissue culture cells or calli. A plant cell refers to cells harvested or derived from any portion of the plant or plant tissue culture cells or calli.

The rhg1 locus is a chromosomal region identified as a region important for resistance to SCN. A locus is a chromosomal region where one or more trait determinants, genes, polymorphic nucleic acids, or markers are located. A quantitative trait locus (QTL) refers to a polymorphic genetic locus where the underlying gene controls a trait that is quantitatively measured and contains at least two alleles that differentially affect expression of a phenotype or genotype in at least one genetic background, with said locus accounting for part but not all of the observed variation in the overall phenotypic trait that is being assessed. A genetic marker is a nucleotide sequence or amino acid sequence that may be used to identify a genetically linked locus, such as a QTL. Examples of genetic markers include, but are not limited to, single nucleotide polymorphisms (SNP), simple sequence repeats (SSR; or microsatellite), a restriction enzyme recognition site change, genomic copy number of specific genes or target sequences or other sequence based differences between a susceptible and resistant plant.

Figure 6A:
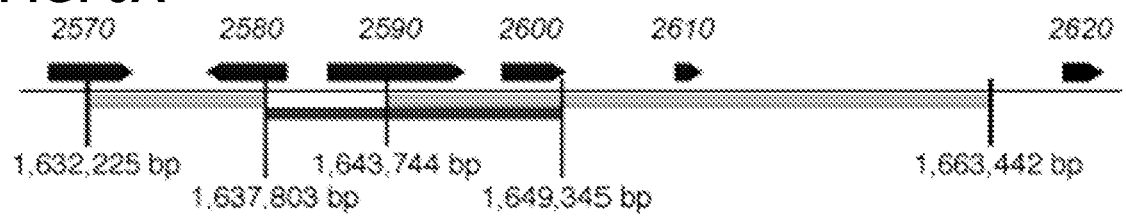
FIG. 6A-6B show Fiber-FISH detection of Rhg1 copy number variation in widely used soybean lines.
Figure 6B:
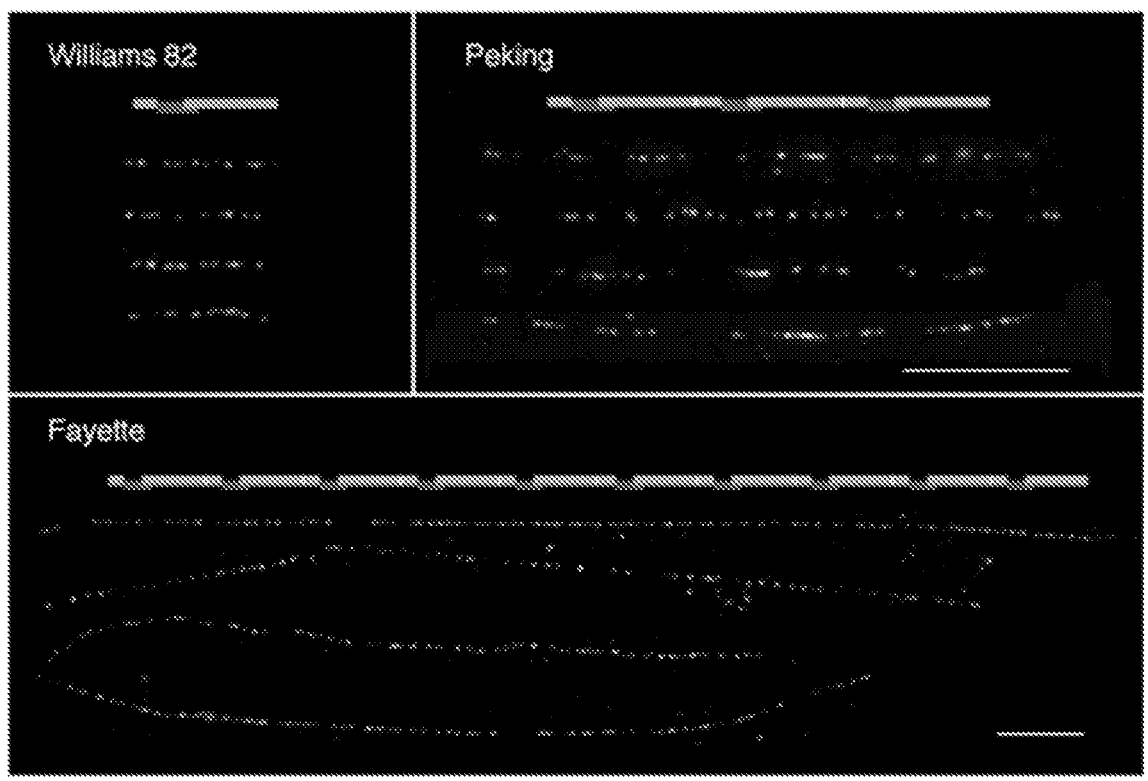

Genetic or selectable markers can be detected using a variety of analytic methods, including RFLP, AFLP, sequence analysis, hybridization such as allele specific hybridization analysis, differential PCR or other methods such as those known to those of skill in the art. A list of single nucleotide polymorphisms between resistant and susceptible soybeans in the Rhg1 multi-gene copy region is provided in Table 1. In another embodiment, the marker is the genomic copy number, or an estimate of the genomic copy number, of at least one of the genes or DNA sequences found in the replicated region of the resistant lines. In yet another embodiment the marker is the genomic DNA segment carrying the border between the replicated region at Glyma18g02610 and Glyma18g02570 as shown in FIGS. 5 and 6. Selection methods may also include analysis of traits, phenotype polymorphisms or selectable markers not defined by DNA or RNA sequence differences, such as differences in methylation of a DNA sequence, or polypeptide expression levels or in gene expression levels. As shown in the Examples the soybean SCN resistance Rhg1 locus, in particular the promoter regions of Glyma18g02610, Glyma18g02590 and Glyma18g02580, was highly methylated in the resistant plants as compared to susceptible plants. Methylation distinctions in and adjacent to these genes, for example in the promoter and upstream regions of the genes, may be used to distinguish between resistant and susceptible lines. In addition, resistant plants had higher mRNA levels for Glyma18g02610, Glyma18g02590 and Glyma18g02580 than susceptible plants. See FIG. 5. Thus methods of detecting the gene expression levels of any of these genes, for example by monitoring mRNA abundance, may be used in the methods described herein. In another embodiment, the marker may be the protein expression level of at least one of Glyma18g02610, Glyma18g02590 and Glyma18g02580. Any of these differences may be used as a screen to test whether a plant or plant cell is likely to be resistant or susceptible to nematodes.

TABLE 1

Amino acid polymorphisms within the 31 kb repeat at rhg1-b. The position of the protein-coding genes was predicted by comparing the fosmid clone sequences to the Glyma1 version of the soybean genome assembly. (L) or (R) indicate either the left or right side of the junction. * indicates an insertion of 1 aa (3 bp of DNA sequence) between amino acid position 287 and 288 based on the Williams 82 genome assembly (Glyma1).

| Gene ID | Amino Acid Position | W82 | #1 | #3 | #4(L) | #5(L) | #5(R) |
|---------|---------------------|-----|----|----|-------|-------|-------|
| 2590 | 203 | Q | K | Q | K | — | K |
| 2590 | 285 | E | Q | E | Q | Q | Q |
| 2590 | 286 | D | H | D | H | H | H |
| 2590 | 287 | D | E | D | E | E | E |
| 2590 | 287-288* | — | A | — | A | A | A |
| 2590 | 288 | L | I | L | I | I | I |

The markers described above are linked to the phenotype of increased resistance to cyst nematodes or alternatively to susceptibility to cyst nematodes. The methods of detecting may comprise amplifying the marker or a portion thereof to produce an amplified product. The presence of the product may be indicative of the marker or the amplified product may be sequenced. The amplified product may also be assessed via differential sensitivity to a restriction endonuclease. The marker may be detected using allele specific hybridization analysis, quantitative PCR, Northern blot analysis, Western blot analysis or another methodology. Methods of detecting or evaluating genetic or phenotypic markers of traits such as those descried herein are available to those of skill in the art, many such methods are provided in the Examples, and it is anticipated that new methods may be developed in the future to detect the Rhg1 polymorphisms described herein. For example, the markers can be used to detect the presence or absence of the multi-copy Rhg1 region during breeding selection processes.

A linked locus describes a situation in which a genetic marker and a trait are closely linked chromosomally such that the genetic marker and the trait do not independently segregate and recombination between the genetic marker and the trait does not occur during meiosis with a high frequency. The genetic marker and the trait may segregate independently, but generally do not. For example, a genetic marker for a trait may only segregate independently from the trait 5% of the time; suitably only 5%, 4%, 3%, 2%, 1%, 0.75%, 0.5%, 0.25%, or less of the time. Genetic markers with closer linkage to the trait-producing locus will serve as better markers because they segregate independently from the trait less often because the genetic marker is more closely linked to the trait. Genetic markers that directly detect polymorphic nucleotide sites that cause variation in the trait of interest are particularly useful for their accuracy in marker-assisted plant breeding. Thus, the methods of screening provided herein may be used in traditional breeding, recombinant biology or transgenic breeding programs or any hybrid thereof to select or screen for resistant varieties.

In the methods described herein the SCN resistance or susceptibility phenotype of a first soybean is identified by comparing the genetic marker in the first soybean to that in a second soybean with a known resistance phenotype. The second soybean may be known to be resistant to SCN. Thus a first soybean having the same genetic marker as the second soybean is likely to also be resistant to SCN. Resistant soybeans are known in the art and include but are not limited to PI88788, Peking, Hartwig, Fayette, Forrest, LD02-5320, LD02-5025, and LD01-7323 or lines carrying loci that contributed to or were derived from these cultivars such as those provided in Table 2. In particular, the methods allow identification of soybean plants having increased resistance to Race 3 SCN and other nematode populations, similar to PI88788. Alternatively, the second soybean may be known to be susceptible to SCN. Thus a first soybean having the same genetic marker as the second soybean is likely to be susceptible to SCN. Susceptible soybeans are known in the art and include, but are not limited to, 'Williams 82', Essex, Thorne, Sturdy, LG03-1672, and LG00-3372 or lines carrying loci that contributed to or were derived from one of these cultivars such as those provided in Table 2. In particular, the methods allow identification of soybean plants having susceptibility to SCN similar to that of 'Williams 82.' Although resistance to SCN is widely observed to be a quantitative trait, the terms susceptibility and resistance as used in the preceding paragraphs refer to qualitative trans, such that identification as a resistant soybean indicates that the soybean is more resistant than the susceptible soybean line to which it is being compared. Likewise, identification of a soybean as a susceptible soybean indicates that the soybean is more sensitive than the resistant soybean line to which it is being compared.

TABLE 2

Analysis of copy number of the Rhg1 locus in various soybean varieties

| | Copy Number Estimate | |
|---|---|---|
| Genotype | Chromosome 18 Rhg1) | Chromosome 11 (homolog) |
| LD00-3309 | 9.9 ± 1.8 | 0.9 ± 0.2 |
| 4J105-3-4 | 9.9 ± 1.9 | 1.0 ± 0.2 |
| LD02-4485 | 9.8 ± 2.2 | 1.0 ± 0.3 |
| CL0J095-4-6 | 9.6 ± 1.5 | 0.9 ± 0.2 |
| LD02-9050 | 9.4 ± 3.4 | 1.0 ± 0.4 |
| LG05-4292 | 9.4 ± 1.7 | 1.0 ± 0.2 |
| Maverick | 9.2 ± 3.3 | 0.9 ± 0.3 |
| LD01-5907 | 2.9 ± 0.9 | 1.1 ± 0.3 |
| PI427_136 | 1.1 ± 0.3 | |
| PI404_188A | 1.1 ± 0.3 | |
| LG98-1605 | 1.1 ± 0.4 | |
| U03-100612 | 1.1 ± 0.2 | |
| LG90-2550 | 1.1 ± 0.3 | |
| PI398_881 | 1.1 ± 0.2 | |
| PI518_751 | 1.0 ± 0.3 | |
| IA3023 | 1.0 ± 0.2 | |
| PI561_370 | 1.0 ± 0.2 | |
| HS6-3976 | 1.0 ± 0.3 | |
| LG03-2979 | 1.0 ± 0.2 | |
| LG92-1255 | 1.0 ± 0.3 | |
| Prohio | 1.0 ± 0.2 | |
| LG03-3191 | 1.0 ± 0.2 | |
| PI507_681B | 1.0 ± 0.2 | |
| LG05-4464 | 0.9 ± 0.2 | |
| NE3001 | 0.9 ± 0.3 | |

Resistance (or susceptibility) to SCN can be measured in a variety of ways, several of which are known to those of skill in the art. In the examples, soybean roots were experimentally inoculated with SCN and the ability of the nematodes to mature (molt and proceed to developmental stages beyond the J2) on the roots was evaluated as compared to a susceptible and/or resistant control plant. A SCN greenhouse test is also described in the Examples and provides an indication of the number of cysts on a plant and is reported as the female index. Increased resistance to nematodes can also be manifested as a shift in the efficacy of resistance with respect to particular nematode populations or genotypes. Additionally but not exclusively, SCN-susceptible soybeans grown on SCN-infested fields will have significantly decreased crop yield as compared to a comparable SCN-resistant soybean. Improvement of any of these metrics has utility even if all of the above metrics are not altered.

As demonstrated in the Examples a set of three genes found on a tandemly repeated segment of chromosome 18 were identified whose silencing led to increased susceptibility to SCN in a resistant variety. The three genes are found along with a fourth gene, part of a fifth gene, and other DNA sequences in a chromosome segment approximately 31 kb in length that is present in 10 copies in the soybean varieties that carry the rhg1-b allele or haplotype of Rhg1 that is in widespread commercial use for control of SCN disease of soybean. This Rhg1 chromosome segment is found in at least three copies in all SCN resistant varieties tested to date. Various resistant varieties early three, seven or ten copies and the higher copy number versions of Rhg1 express higher levels of transcripts for the three genes. Higher copy number versions of Rhg1 also confer more resistance to SCN on their own (exhibit less reliance on the simultaneous presence of desirable alleles of other SCN resistance QTL such as Rhg4 in order to effective confer SCN resistance, relative to Rhg1 haplotypes with lower Rhg1 repeat copy numbers). In the Examples, over-expression of the three genes in a susceptible variety made roots more resistant to SCN. Methods of increasing resistance of a plant to cyst nematodes by selecting plants carrying genetic markers associated with Glyma18g02610, Glyma18g02590, and/or Glyma18g02580 alleles that are present within the Rhg1 locus are described. As shown in the Examples, genetic polymorphisms ranging from single nucleotide polymorphisms to gene rearrangements (i.e. gene duplications) and differences in methylation may occur in other *Glycine max* plant lines and other *Glycine* species, which may alter the expression or biological impact of one or more genes linked to the Rhg1 locus, and careful selection of desirable alleles of particular genes at the Rhg1 locus may be desirable to allow selection of plants with increased resistance to SCN.

Methods of increasing resistance of a plant to cyst nematodes, including but not limited to SCN, by increasing the expression of or altering the expression pattern of or increasing the copy number of a polynucleotide encoding the Glyma18g02610 (SEQ ID NO: 3), Glyma18g02590 (SEQ ID NOs: 2, 5 and 6), and/or Glyma18g02580 (SEQ ID NO: 1) polypeptides or functional fragments or variants thereof in cells of the plant are also provided. The polypeptide may be 80%, 85%, 90%, 95%, 97%, 98%, 99% or 100% identical to the sequences provided. We have sequenced these genes from both resistant and susceptible varieties and found few polymorphisms within the coding regions and few changes that result in an amino acid change. The Glyma18g2590 polypeptide does have some significant polymorphisms between the resistant and susceptible varieties that appear to be functionally related to SCN resistance as shown in the Examples.

Suitably the expression of the polypeptides encoded by Glyma18g02610, Glyma18g02590, and/or Glyma18g02580 is increased in a root of the plant. Suitably, the expression of the polypeptides encoded by Glyma18g02610, Glyma18g02590, and/or Glyma18g02580 is increased in root cells of the plant. The plant is suitably a soybean plant or portions thereof. The polynucleotides may also be transferred into other non-soybean plants, or homologs of these polypeptides or polynucleotides encoding the polypeptides from other plants, or synthetic genes encoding products similar to the polypeptides encoded by Glyma18g02610, Glyma18g02590, and/or Glyma18g02580 may be overexpressed in those plants. Other plants include but are not limited to sugar beets, potatoes, corn, peas, and beans. The overexpression of the genes may increase the resistance of plants from these other species to nematodes and in particular cyst nematodes, such as the soybean cyst nematode *Heterodera glycines*, the sugar beet cyst nematode *Heterodera schacthii*, the potato cyst nematodes *Globodera pallida* and related nematodes that cause similar disease on potato such as *Globodera rostochiensis*, the corn cyst nematode *Heterodera zeae*, and the pea cyst nematode *Heterodera goettingiana*.

The expression of the polynucleotides may be increased by increasing the copy number of the polynucleotide in the plant, in cells of the plant, suitably root cells, or by identifying plants in which this has already occurred. Suitably, the polynucleotide is present in three, seven or even ten copies. Suitably at least two or all three of the polynucleotides encoding the polypeptides or the polypeptides of Glyma18g02610, Glyma18g02590, and Glyma18g02580 are expressed. Alternatively the expression may be increased using recombinant DNA technology, e.g., by using a strong promoters to drive increased expression of one or more polynucleotides.

In addition, methods of increasing resistance of a plant to cyst nematodes may be achieved by cloning sequences upstream from Glyma18g02610, Glyma18g02590, and/or Glyma18g02580 from resistant lines into susceptible lines. For these methods, nucleotide sequences having at least 60%, 70% or 80% identity to nucleotide sequences that flank the protein-coding regions of Glyma18g02610, Glyma18g02590 or Glyma18g02580 (or sequences having at least 80%, 85%, or 90% identity to those protein-coding regions), said flanking regions including 5' and 3' untranslated regions of the mRNA for these genes, and also including any other genomic DNA sequences that extend from the protein coding region of these genes to the protein coding regions of immediately adjacent genes may be used.

The increase in expression of Glyma18g02610, Glyma18g02590, and/or Glyma18g02580 in the plant may be measured at the level of expression of the mRNA or at the level of expression of the polypeptide encoded by Glyma18g02610, Glyma18g02590, and/or Glyma18g02580. The level of expression may be measured relative to the level of expression in a control plant as shown in the Examples. The control plant may be an SCN-susceptible plant or an SCN-resistant plant. For example, a susceptible plant such as 'Williams 82' may be transformed with an expression vector such that the roots of the transformed plants express increased levels of Glyma18g02610, Glyma18g02590, and/or Glyma18g02580 as compared to an untransformed plant or a plant transformed with a construct that does not change expression of Glyma18g02610, Glyma18g02590, and/or Glyma18g02580, resulting in increased resistance to nematodes. Alternatively, the control may be a plant partially resistant to nematodes and increased expression of Glyma18g02610, Glyma18g02590, and/or Glyma18g02580 may result in increased resistance to nematodes. Alternatively, the plant may be resistant to nematodes and increasing expression of Glyma18g02610, Glyma18g02590, and/or Glyma18g02580 may result in further increased resistance to nematodes. Alternatively, the plant may be more resistant to certain nematode populations, races, Hg types or strains and less resistant to other nematode populations, races, Hg types or strains, and increasing expression of Glyma18g02610, Glyma18g02590, and/or Glyma18g02580 may result in increased resistance to certain of these nematode populations, races, Hg types or strains.

Figure 15:
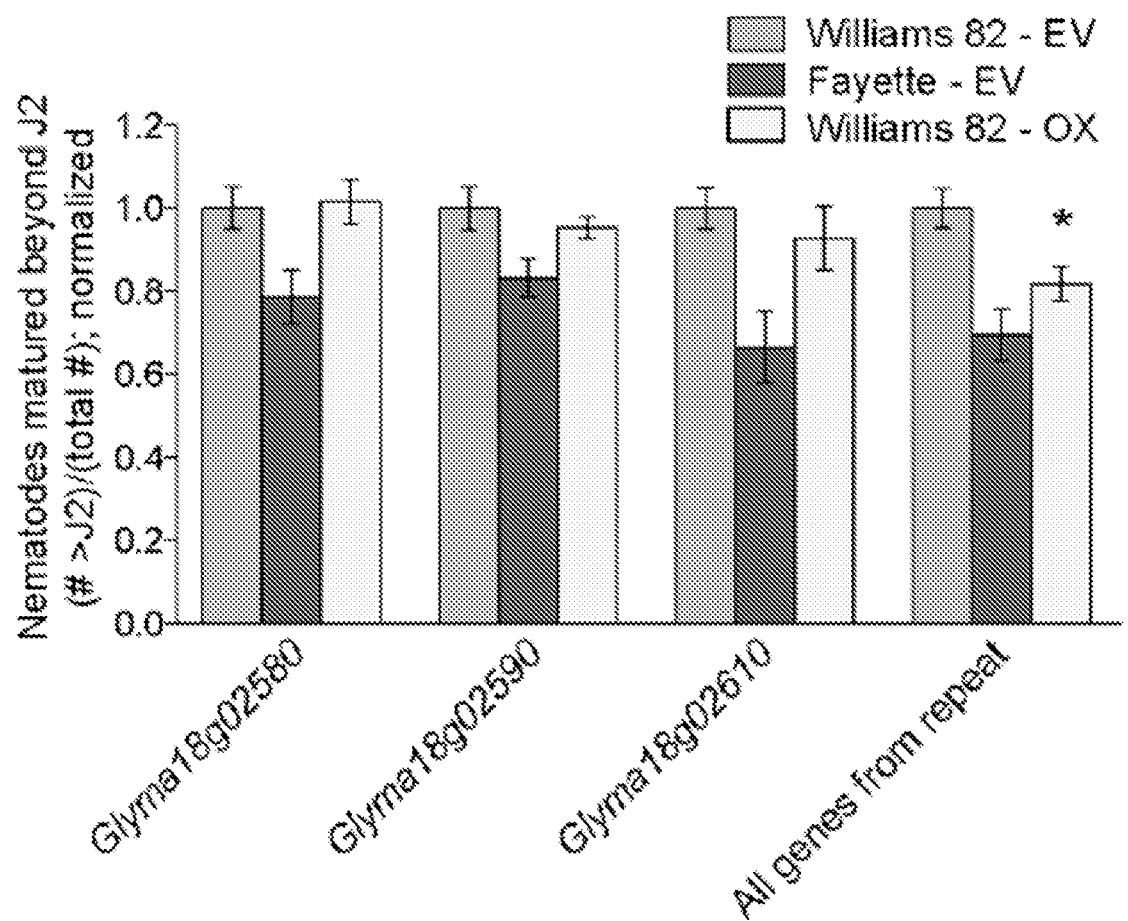
FIG. 15 is a graph showing elevated SCN resistance conferred by simultaneous overexpression of multiple genes rather than overexpression of individual genes from the 31 kb rhg1-b repeat. SCN development beyond J2 stage is reported for transgenic soybean roots (variety Williams 82) overexpressing the designated single genes, or overexpressing all genes encoded within the 31 kb repeat (Glyma18g02580, -2590, -2600 and -2610), relative to Williams 82 (SCN-susceptible) and Fayette (SCN-resistant) controls. Mean±std, error of mean for roots transformed with empty vector (EV) or gene overexpression constructs (OX). *: Williams 82-OX significantly different from Williams 82-EV based on ANOVA p<0.05.
Figure 18A:
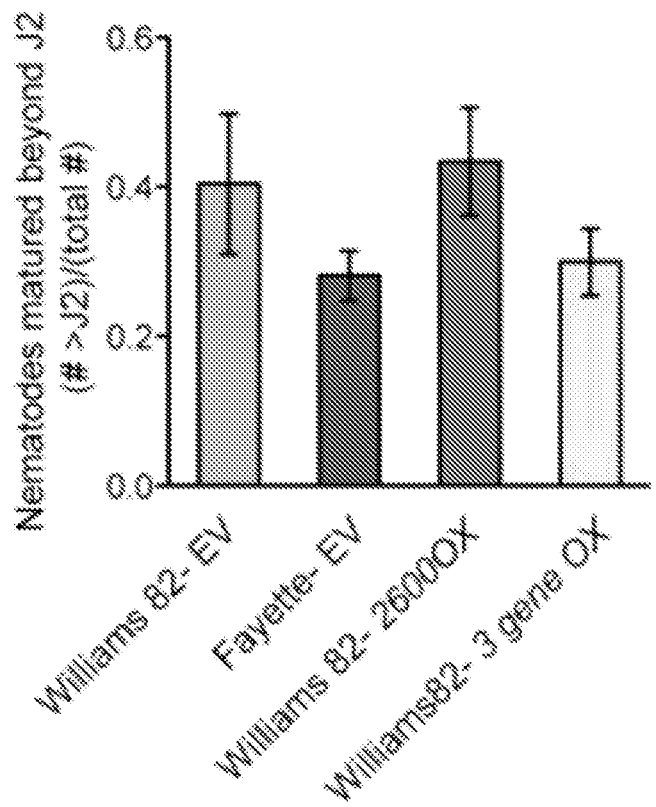
FIG. 18 is a set of graphs showing that overexpression of Glyma18g2580, Glyma18g2590 and Glyma18g2610 in combination can confer resistance on a susceptible Williams 82 variety.
Figure 18B:
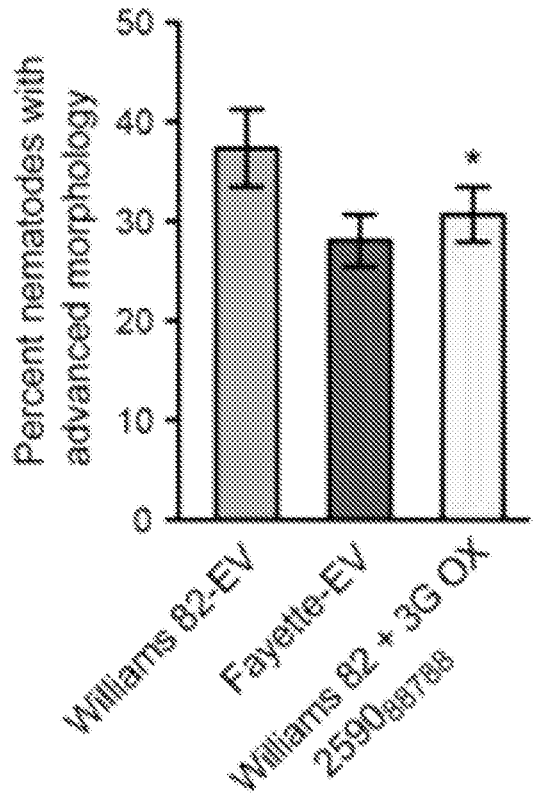

In the Examples, a decrease in expression of Glyma18g023610, Glyma18g02590, and/or Glyma18g02580 is shown to increase the susceptibility of a SCN-resistant soybean to SCN maturation. In addition, roots of the susceptible 'Williams 82' soybean are shown to have lower levels of Glyma18g02610, Glyma18g02590, and/or Glyma18g02580 mRNA as compared to the resistant Fayette line. Because low levels of Glyma18g02610, Glyma18g02590, and/or Glyma18g02580 mRNA correlate with nematode susceptibility, and increased levels correlate with resistance, and direct towering of Glyma18g02610, Glyma18g02590, and/or Glyma18g02580 mRNA is causally associated with greater nematode susceptibility of previously resistant tissues, increasing the levels of Glyma18g02610, Glyma18g02590, and/or Glyma18g02580 in a soybean should in many instances increase the resistance of the soybean to nematodes, in particular SCN. In FIG. 15, increased expression of a combination of Glyma18g02600, Glyma18g02610, Glyma18g02590, and Glyma18g02580 was shown to increase resistance to SCN of a susceptible line. Increased expression of three genes, Glyma18g02610. Glyma18g02590, and Glyma18g02580 was also shown to increase resistance of an SCN susceptible variety in FIG. 18. Increased expression of fewer than these three polynucleotides or of the polypeptides encoded by the polynucleotides may be similarly effective to increase resistance.

Expression of Glyma18g02610, Glyma18g02590, and/or Glyma18g02580 may be increased in a variety of ways including several apparent to those of skill in the art and may include transgenic, non-transgenic and traditional breeding methodologies. For example, the expression of the polypeptide encoded by Glyma18g02610, Glyma18g02590, and/or Glyma18g02580 may be increased by introducing a construct including a promoter operational in the plant operably linked to a polynucleotide encoding the polypeptide into cells of the plant. Suitably, the cells are root cells. Alternatively, the expression of the polypeptide encoded by Glyma18g02610, Glyma18g02590, and/or Glyma18g02580 may be increased by introducing a transgene including a promoter operational in the plant operably linked to a polynucleotide encoding the polypeptide into cells of the plant. The promoter may be a constitutive or inducible promoter capable of inducing expression of a polynucleotide in all or part of the plant, plant roots or plant root cells. In another embodiment, the expression of Glyma18g0208 Glyma18g02590, and/or Glyma18g02580 may be increased by increasing expression of the native polypeptide in a plant or in cells of the plant, such as the plant root cells. In another embodiment, the expression of Glyma18g02610, Glyma18g02590, and/or Glyma18g02580 may be increased by increasing expression of the native polypeptide in a plant or in cells of the plant such as the nematode feeding site, the syncitium, or cells adjacent to the syncitium. In another embodiment, the expression of Glyma18g02610, Glyma18g02590, and/or Glyma18g02580 may be increased by increasing expression of the native polypeptide in a plant or in cells of the plant such as sites of nematode contact with plant cells. In another embodiment, expression may be increased by increasing the copy number of Glyma18g02610, Glyma18g02590, and/or Glyma18g02580. Other mechanisms for increasing the expression of Glyma18g02610, Glyma18g02590, and/or Glyma18g02580 include, but are not limited to, increasing expression of a transcriptional activator, reducing expression of a transcriptional repressor, addition of an enhancer region capable of increasing expression of Glyma18g02610, Glyma18g02590, and/or Glyma18g02580, increasing mRNA stability, altering DNA methylation, histone acetylation or other epigenetic or chromatin modifications in the vicinity of the relevant genes, or increasing protein or polypeptide stability.

In addition to the traditional use of transgenic technology to introduce additional copies or increase expression of the genes and mediate the increased expression of the polypeptides of Glyma18g02610, Glyma18g02590, and/or Glyma18g02580 in plants, transgenic or non-transgenic technology may be used in other ways to increase expression of the polypeptides. For example, plant tissue culture and regeneration, mutations or altered expression of plant genes other than Glyma18g02610, Glyma18g02590, and/or Glyma18g02580, or transgenic technologies, can be used to create instability in the Rhg1 locus or the plant genome more generally that create changes in Rhg1 locus copy number or gene expression behavior. The new copy number or gene expression behavior can then be stabilized by removal of the variation-inducing mutations or treatments, for example by further plant propagation or a conventional cross. In one of the examples, although a transgenic plant was used to create the change in copy number, the result would be anontransgenic line (and conceivably regulated as such with enhanced resistance due to increased copy number of the locus. Examples of transgenic technologies that might be used in this way include targeted zinc fingers, ribozymes or other sequence-targeted enzymes that create double stranded DNA breaks at or close to the Rhg1 locus, the cre/loxP system from bacteriophage lambda, Transcription Activator-Like Effector Nucleases (TALENs), artificial DNA or RNA sequences designed to recombine with Rhg1 that can be introduced transiently, or enzymes that "shuffle" DNA such as the mammalian Rag1 enzyme or DNA transposases. Mutations or altered expression of endogenous plant genes involved in DNA recombination, DNA rearrangement and/or DNA repair pathways are additional examples.

The screening methods described above could also be used to screen soybean isolates (*Glycine max*) and closely related species (*Glycine soja, Glycine tomentella* or other *Glycine* species) for resistance markers and then resistant lines can be crossed naturally or artificially with soybean to develop a soybean with a variant copy number or sequence at the Rhg1 site. Any useful alleles identified in such screens could then be introduced using traditional breeding or transgenic technology into soybeans.

Non-transgenic means of generating soybean varieties carrying traits of interest such as increased resistance to SCN are available to those of skill in the art and include traditional breeding, chemical or other means of generating chromosome abnormalities, such as chemically induced chromosome doubling and artificial rescue of polyploids followed by chromosome loss, knocking-out DNA repair mechanisms or increasing the likelihood of recombination or gene duplication by generation of chromosomal breaks. Other means of non-transgenetically increasing the expression or copy number of Glyma18g02610, Glyma18g02590, and/or Glyma18g02580 include the following: screening for mutations in plant DNA encoding miRNAs or other small RNAs, plant transcription factors, or other genetic elements that impact Glyma18g02610, Glyma18g02590, and/or Glyma18g02580 expression; screening large field or breeding populations for spontaneous variation in copy number or sequence at Rhg1 by screening of plants for nematode resistance, Rhg1 copy number or other Rhg1 gene or protein expression traits as described in preceding paragraphs; crossing of lines that contain different or the same copy number at Rhg1 but have distinct polymorphisms on either side, followed by selection of recombinants at Rhg1 using molecular markers from two distinct genotypes flanking the Rhg1 locus; chemical or radiation mutagenesis or plant tissue culture/regeneration that creates chromosome instability or gene expression changes, followed by screening of plants for nematode resistance, Rhg1 copy number or other Rhg1 gene or protein expression traits as described in preceding paragraphs; or introduction by conventional genetic crossing of non-transgenic loci that create or increase genome instability into Rhg1-containing lines, followed by screening of plants for either nematode resistance or Rhg1 copy number. Examples of loci that could be used to create genomic instability include active transposons (natural or artificially introduced from other species), loci that activate endogenous transposons (for example mutations affecting DNA methylation or small RNA processing such as equivalent mutations to met1 in *Arabidopsis* or mop1 in maize), mutation of plant genes that impact DNA repair or suppress illegitimate recombination such as those orthologous or similar in function to the Sgs1 helicase of yeast or RecQ of *E. coli*, or overexpression of genes such as RAD50 or RAD52 of yeast that mediate illegitimate recombination. Those of skill in the art may find other transgenic and non-transgenic methods of increasing expression of Glyma18g02610, Glyma18g02590, and/or Glyma18g02580.

The polynucleotides and/or polypeptides described and used herein may encode the full-length or a functional fragment of Glyma18g02610, Glyma18g02590, and/or Glyma18g02580 from the rhg1-b locus, or a naturally occurring or engineered variant of Glyma18g02610, Glyma18g02590, and/or Glyma18g02580, or a derived polynucleotide or polypeptide all or part of which is based upon nucleotide or amino acid combinations similar to all or portions of Glyma18g02610, Glyma18g02590, and/or Glyma18g02580 or their encoded products. Additional polynucleotides encoding polypeptides may also be included in the construct such as Glyma18g02600 (which encodes the polypeptide of SEQ ID NO: 4). The polypeptide may be at least 80%, 85%, 90%, 95%, 97%, 98%, 99% or 100% identical to the sequences provided herein. The polynucleotides encoding the polypeptides may be at least 50%, 60%, 65%, 70%, 75%, 80%, 85%, 90%, 95% or 100% identical to the sequences available in the public soybean genetic sequence database.

The expression of the polypeptide encoded by Glyma18g02610, Glyma18g02590, and/or Glyma18g02580 may be increased, suitably the level of polypeptide is increased at least 1.2, 1.5, 1.7, 2, 3, 4, 5, 7, 10, 15, 20 or 25 fold in comparison to the untreated, susceptible or other control plants or plant cells. Control cells or control plants are comparable plants or cells in which Glyma18g02610, Glyma18g02590, and/or Glyma18g02580 expression has not been increased, such as a plant of the same genotype transfected with empty vector or transgenic for a distinct polynucleotide.

Increased resistance to nematodes may be measured as described above. The increased resistance may be measured by the plant having a lower percentage of invading nematodes that develop past the J2 stage, a lower rate of cyst formation on the roots, reduced SCN egg production within cysts, reduced overall SCN egg production per plant, and/or greater yield of soybeans on a per-plant basis or a per-growing-area basis as compared to a control plant grown in a similar growth environment. Other methods of measuring SCN resistance also will be known to those with skill in the art. In the methods of increasing resistance to nematodes described herein, the resulting plant may have at least 10% increased resistance as compared to the untreated or control plant or plant cells. Suitably the increase in resistance is at least 15%, 20%, 30%, 50%, 100%, 200%, 500% as compared to a control. Suitably, the female index of the plant with increased resistance to nematodes is about 80% or less of the female index of an untreated or control plantplant derived from the same or a similar plant genotype, infested with a similar nematode population within the same experiment. More suitably, the female index after experimental infection is no more than 60%, 40%, or 20% of that of the control plant derived from the same or a similar plant genotype, infested with a similar nematode population within the same experiment. Suitably, when grown in fields heavily infested with SCN (for example, more than 2500 SCN eggs per 100 cubic centimeters of soil), soybean grain yields of field-grown plants are 2% greater than isogenic control plants. More suitably, the grain yield increase is at least 3%, 4%, or 5% over that of isogenic control plants grown in similar environments.

Also provided herein are constructs including a promoter operably linked to a Glyma18g02610, Glyma18g02590, and/or Glyma18g02580 polynucleotide encoding a polypeptide comprising SEQ ID NO: 1-3 or 5-6 or a fragment or functional variant thereof. Also included are homologs or variants of these sequences from other soybean varieties. The constructs may further include Glyma18g02600 or other genes. The constructs may be introduced into plants to make transgenic plants or may be introduced into plants, or portions of plants, such as plant tissue, plant calli, plant roots or plant cells. Suitably the promoter is a plant promoter, suitably the promoter is operational in root cells of the plant. The promoter may be tissue specific, inducible, constitutive, or developmentally regulated. The constructs may be an expression vector. Constructs may be used to generate transgenic plants or transgenic cells. The polypeptide may be at least 80%, 85%, 90%, 95%, 97%, 98%, 99% or 100% identical to the sequences of SEQ ID NO: 1-3 or 5-6. The constructs may comprise all three polynucleotides and may mediate expression of all three polypeptides.

Transgenic plants including a non-native or exogenous polynucleotide encoding the rhg1-b polypeptides identified and described herein are also provided. Suitably the transgenic plants are soybeans. The transgenic plants express increased levels of Glyma18g02610, Glyma18g02590, and/or Glyma18g02580 polypeptide as compared to a control non-transgenic plant from the same line, variety or cultivar or a transgenic control expressing a polypeptide other than Glyma18g02610, Glyma18g02590, and/or Glyma18g02580. The transgenic plants also have increased resistance to nematodes, in particular SCN, as compared to a control plant. Portions or parts of these transgenic plants are also useful. Portions and parts of plants includes, but is not limited to, plant cells, plant tissue, plant progeny, plant asexual propagates, plant seeds.

Transgenic plant cells comprising a polynucleotide encoding a polypeptide capable of increasing resistance to nematodes such as SCN are also provided. Suitably the plant cells are soybean plant cells. Suitably the cells are capable of regenerating a plant. The polypeptide comprises the sequences of SEQ ID NOs: 1-3 or 5-6 or fragments, variants or combinations thereof. The polypeptide may be 85%, 90%, 95%, 97%, 98%, 99% or 100% identical to the sequences provided. The transgenic cells may be found in a seed. A plant, such as a soybean plant, may include the transgenic cells. The plant may be grown from a seed comprising transgenic cells or may be grown by any other means available to those of skill in the art. Chimeric plants comprising transgenic cells are also provided.

The expression of the polypeptide and the polynucleotides encoding the polypeptides in the transgenic plant is altered relative to the level of expression of the native polypeptides in a control soybean plant. In particular the expression of the polypeptides in the root of the plant is increased. The transgenic plant has increased resistance to nematodes as compared to the control plant. The transgenic plant may be generated from a transgenic cell or callus using methods available to those skilled in the art.

The Examples provided below are meant to be illustrative and not to limit the scope of the invention or the claims. All references and appendices cited herein are hereby incorporated by reference in their entireties.

EXAMPLES

To identify the gene conferring resistance to SCN in the PI88788 soybean within the locus identified by Kim et al., 2010 (within the chromosomal interval defined by the termini BARCSOYSSR_18_0090 and BARCSOYSSR_18_0094), a candidate gene testing approach was used. This approach is described in Melito et al. (BMC Plant Biology 2010, 10:104), which is incorporated herein by reference in its entirety. Briefly, this candidate gene approach was completed with various genes at the Rhg1 locus defined above using a resistant soybean variety Fayette, which carries the PI88788-derived rhg1-b allele of the Rhg1 locus, to make transgenic soybean roots that early gene-silencing constructs and then testing these transgenic roots for loss of SCN resistance. The silencing strategy used is depicted in FIG. 2. The artificial microRNA used in the Melito et al. reference was replaced with artificial microRNA sequences directed against various candidate or putative genes within the Rhg1 locus. The expression of the artificial microRNAs was driven by the soybean Ubi3 promoter. The construct also contained a GFP reporter such that transformed roots could readily be identified by GFP expression. Transgenic soybean roots expressing artificial micro-RNA (amiRNA) or hairpin (RNAi) constructs were produced using *Agrobacterium rhizogenes*. Roots expressing GFP were selected for further analysis. Transgenic roots were inoculated with SCN to test for decreased or increased resistance to SCN caused by candidate gene silencing conditioned by artificial microRNA expression.

Figure 3A:
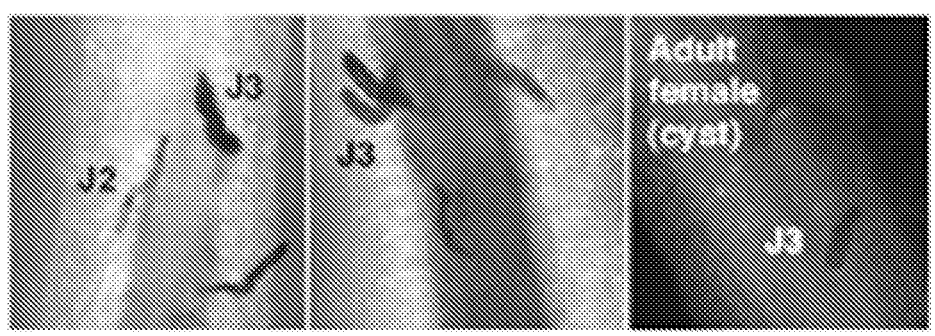
FIG. 3A-3B show that there are three genes at rhg1-b that contribute to SCN resistance.
Figure 3B:
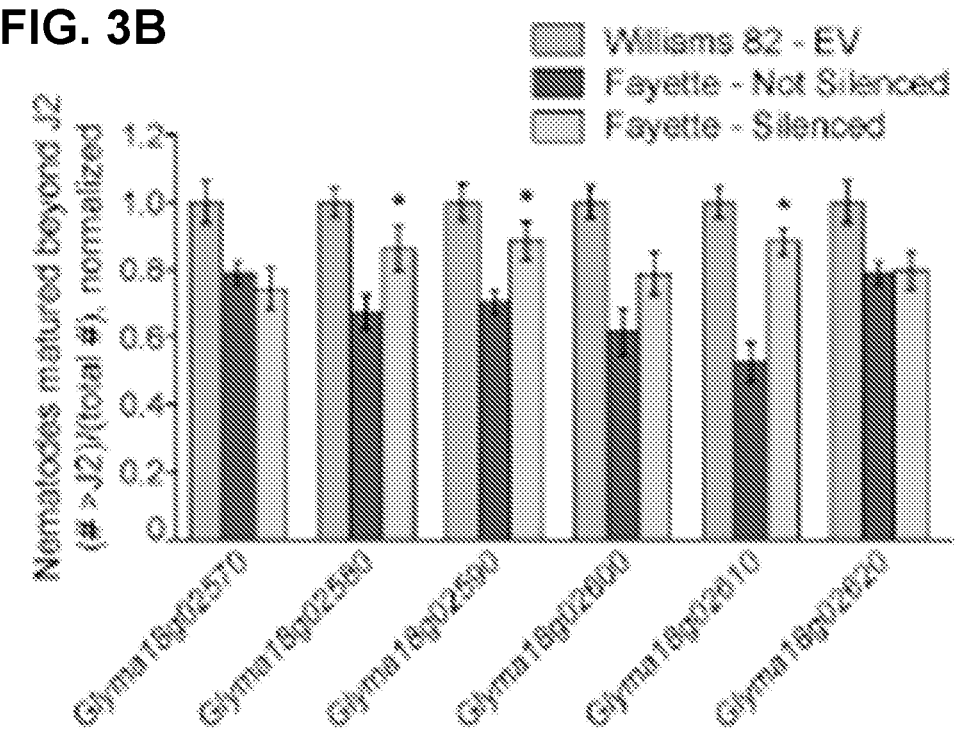
Figure 4A:
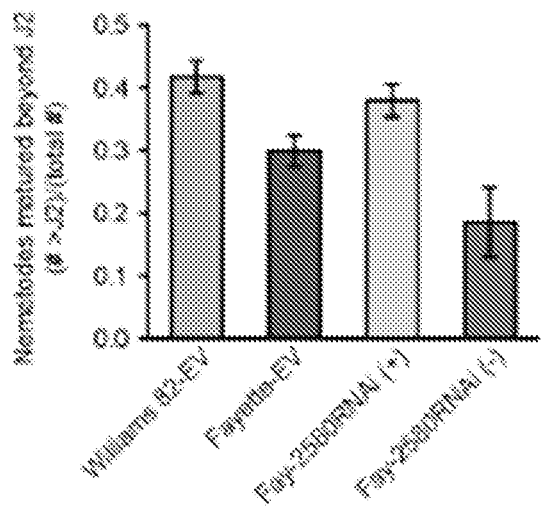
FIGS. 4A-4D show a set of graphs showing that nematode development is impacted by level of silencing.
Figure 4B:
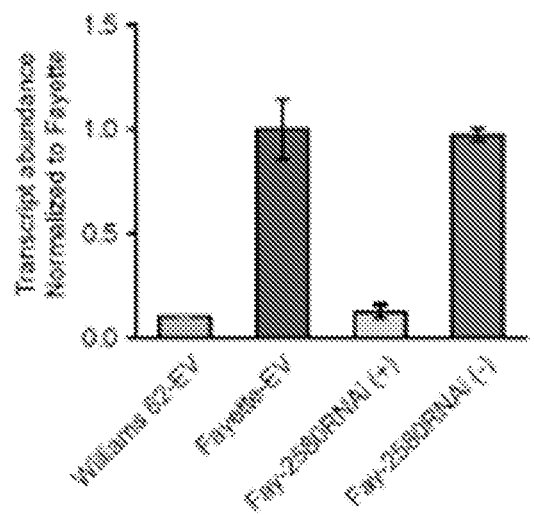
Figure 4C:
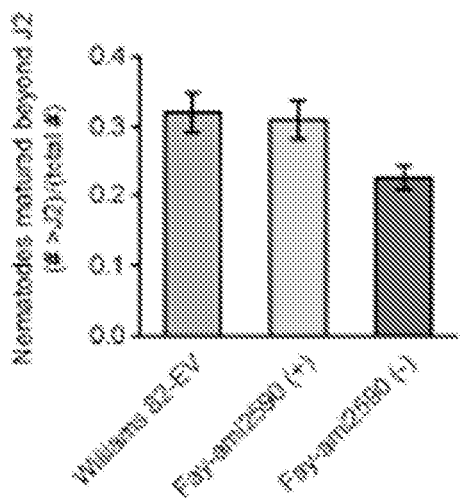
Figure 4D:
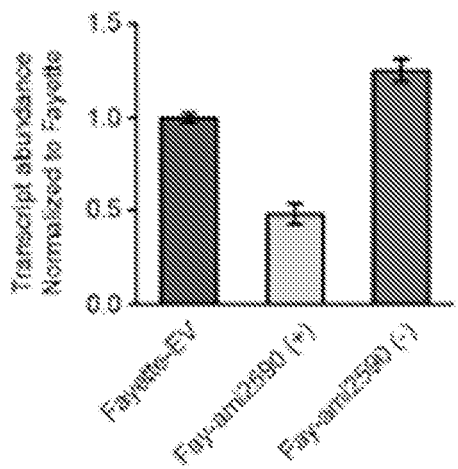

Soybean resistance to SCN was measured two weeks after root inoculation by determining the proportion of the total nematode population that had advanced past the J2 stage in each root (FIG. 3A), relative to known resistant and susceptible controls. Silencing any of three closely linked genes, namely Glyma18g2580, Glyma18g2590, and Glyma18g2610, at the rhg1-b locus of the SCN-resistant soybean variety Fayette significantly reduced SCN resistance (FIG. 3B). Depletion of resistance was dependent on target transcript reduction (FIG. 4). Silencing of other genes in and around the locus did not impact SCN resistance (e.g., FIG. 3B, genes Glyma18g02570 and 2620).

The predicted Glyma18g02610 protein product contains a Wound-induced protein domain (Pfam domain PF07107; M Punta, et al., (2012) *The Pfam protein families database. Nucleic Acids Research Database Issue* 40:D290-D301 and Logemann et al., (1988) *Differential expression of genes in potato tubers after wounding. Proc Natl Acad Sci USA* 85: 1136-1140) and a homologous (55% identical) protein in ice plant (*Mesembryanthemum crystallinum*) was previously shown to be responsive to both biotic and abiotic stimuli (Yen et al., *Environmental and developmental regulation of the wound-induced cell wall protein WI12 in the halophyte ice plant. Plant Physiol.* 127:517-528). The annotated protein product of Glyma18g02610 does not have other widely known protein domains or inferred biochemical functions that, at the present time, are obvious to those with normal skill in the art. However, the above results indicate that Glyma18g02610 is necessary for full Rhg1-mediated SCN resistance.

A Genomic Duplication of Four Genes at Rhg1 in *Glycine max* is Present in the Tested SCN-Resistant Lines Concurrent study of the physical structure of the rhg1-b locus revealed an unusual genomic configuration. A 31.2 kb genome segment, encoding the above three genes that contribute to SCN resistance, is present in multiple copies in SCN resistant lines (FIGS. 5, 6). The DNA sequence of fosmid clone inserts carrying genomic DNA from the rhg1-b genetic interval identified a unique DNA junction, not present in the published Williams 82 soybean genome, in which a 3' fragment of Glyma18g02570 is immediately adjacent to the intergenic sequence downstream of (centromeric to) Glyma18g02610 (FIG. 5A). The genomic repeat contains full copies of Glyma18g02580, -2590, -2600 and -2610 as well as the final two exons of Glyma18g02570. Whole-genome shotgun sequencing of a line containing rhg1-b revealed ten-fold greater depth of coverage of this interval relative to surrounding or homologous regions (FIG. 5B), suggesting the presence of multiple repeats.

Figure 7C:
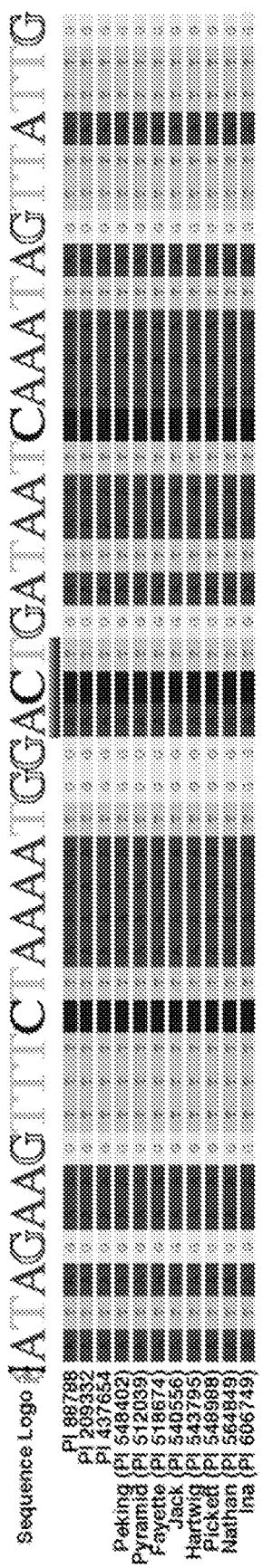

Sequencing and PCR amplification confirmed the presence of the Glyma18g02610-2570 junction in DNA from multiple SCN-resistant soybean accessions, including accessions that carry the commercially important PI 88788, Peking and PI 437654 haplotypes of the Rhg1 locus (FIG. 5C and FIG. 7). The junction was not detected in four tested SCN-susceptible varieties including Williams 82 (FIG. 7B). This constitutes a direct test for economically desirable alleles of the Rhg1 locus. The shared identity of the junction sites from disparate sources of SCN resistance suggests a shared origin of the initial resistance-conferring event at Rhg1.

Fiber-FISH (fluorescence in situ hybridization) was utilized to directly determine the number of copies and arrangement of the 31 kb repeat segment in different haplotypes of the Rhg1 locus. The hybridization pattern and DNA fiber length estimates generated using these probes (FIG. 6 and Table 3) are consistent with the presence of a single copy of the repeat in Williams 82, as in the reference soybean genome. In Fayette, fiber-FISH revealed ten copies per DNA fiber of the predicted 31 kb repeat segment, in the same configuration throughout the multiple nuclei sampled, in a pattern indicating ten direct repeats abutting in a head-to-tail arrangement (FIG. 6 and Table 3). No additional copies (e.g., at other loci) were evident. In samples from soybean line Peking, three copies per DNA fiber were present in apparent direct repeat orientation (FIG. 6). Although fiber-FISH cannot resolve small sequence differences, the single size of all junction-amplification PCR products and the consistency of all junction sequences assembled from fosmid or genomic DNA sequencing (FIG. 7) further suggest the presence of adjacent direct repeat copies.

TABLE 3

Length estimates for Fiber-FISH hybridization signals.
N: number of DNA fibers analyzed.

|  | Length of Fiber-FISH signals (μm) | Estimated Length of Fiber-FISH signals (kb) | N |
| --- | --- | --- | --- |
| Williams 82 | 8.60 ± 0.49 | 27.60 ± 1.58 | 20 |
| Fayette | 96.56 ± 7.54 | 309.94 ± 24.2 | 20 |
| Peking | 34.42 ± 2.91 | 110.48 ± 9.34 | 20 |

To discover additional copy number and DNA polymorphisms we analyzed whole genome re-sequencing (WGS) data for 41 soybean lines, the "NAM parents" from a current nested association mapping study, using sequence data provided by Dr. Perry Cregan. The data set consists of whole genome shotgun sequencing reads produced using Illumina Hiseq equipment and protocols, with average depth of sequencing coverage ranging from 5 to 60 fold. Reads were mapped to the Williams 82 reference genome (Phytozome, assembly 189) and analyzed for read depth (RD), INDELs and SNPs relative to the SCN susceptible line Williams 82. When this Illumina read depth was used to estimate copy number at the Rhg1 locus, using methods analogous to those used to generate FIG. 5B, 8 of the 41 soybean lines analyzed had a normalized read depth for the approximately 31 kb Rhg1 region (corresponding to the rhg1-b repeat segment described above) that differed by greater than 5 standard deviations of the mean from the read depth of the two 30 kb regions immediately flanking the region corresponding to the rhg1-b repeat segment. See Table 2. Seven of those lines had an estimated copy number ranging from 9.2 to 9.9 copies. These lines have PI 88788 in their pedigree, where pedigree are available, and have been classified as SCN-resistant in laboratory and/or field tests. The other genotype predicted to carry Rhg1 repeats had an estimated copy number of 2.9. Its pedigree contains both Peking and PI 437654. The Rhg1 loci derived from Peking and PI 437654 are widely recognized to be much less effective at conferring SCN resistance if they are not coupled with preferred alleles of an unlinked locus, Rhg4. All other genotypes (33) were estimated to contain one copy of the approximately 31 kb of Rhg1 DNA described in this document. All twelve of the 33 lines that had an available, previously determined SCN resistance phenotype were listed as SCN susceptible, while information on the SCN resistance phenotype was not readily available for the other 21 lines. As a control, read depth was used to estimate copy number at the homologous region on Chromosome 11. The estimated copy number was approximately 1 in all tested genotypes. In addition to those lines shown in Table 2, we recently determined that a variety known as Cloud (PI 548316), that displays intermediate levels of SCN resistance, carries seven copies of the Rhg1 locus repeat segment.

The source of the first duplication event to arise at Rhg1 is not known, but was possibly the result of nearby Ty1/copia-like retrotransposon RTvr1 or RTvr2 activity. Later copy number expansion may have occurred by rare unequal exchange events between homologous repeats during meiotic recombination.

Figure 7E:
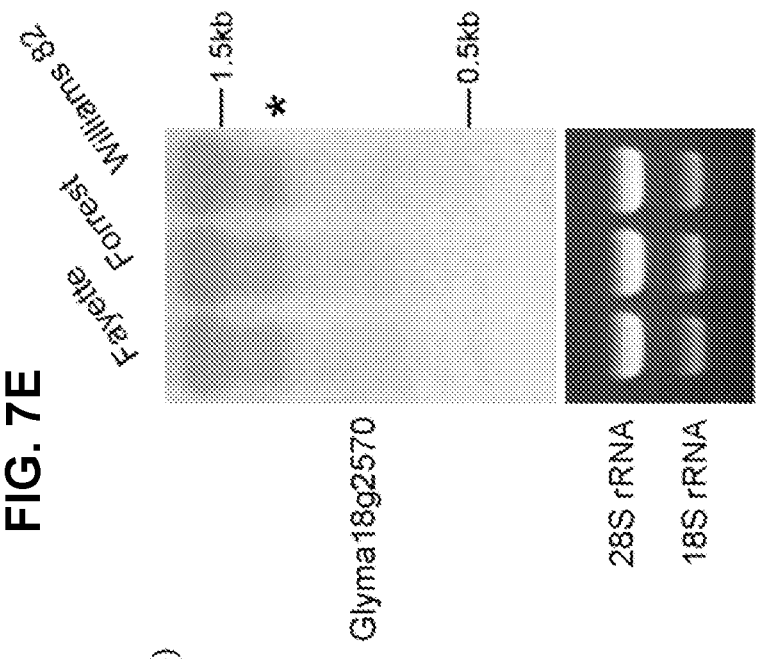
Figure 7D:
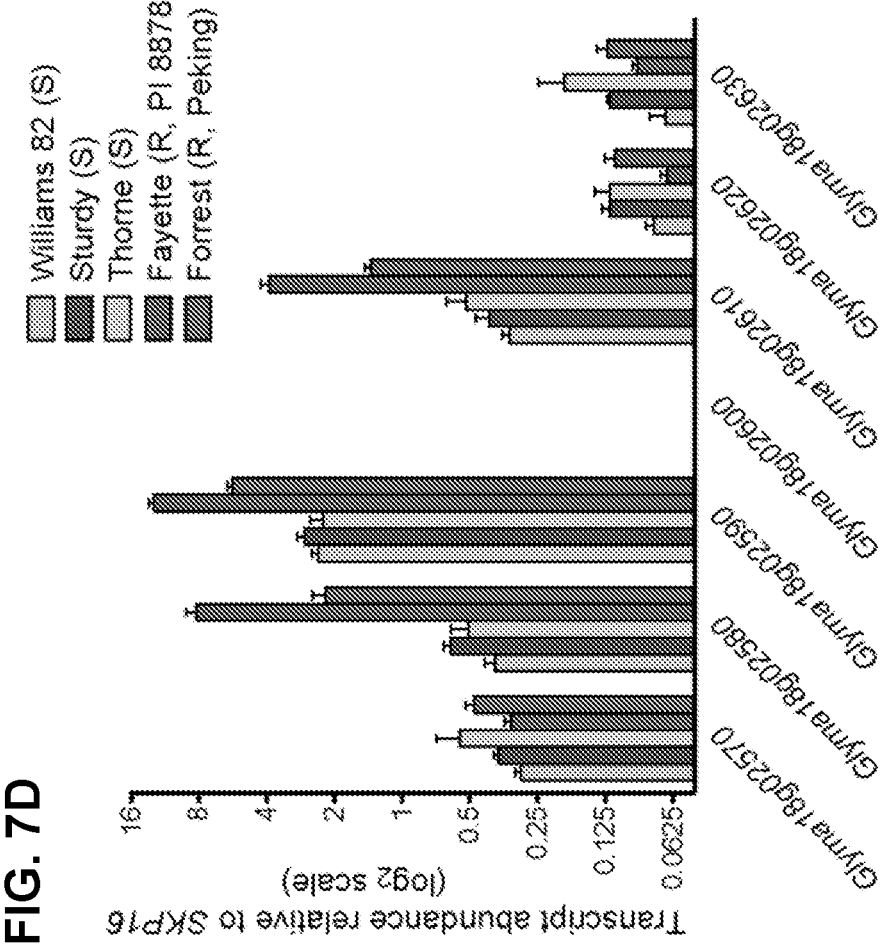

Genes within the Duplicated Gene Block at rhg1-b are Expressed at Higher Levels than their Homologs from SCN-Susceptible Rhg1 Haplotypes Gene expression analysis using quantitative PCR (qPCR) determined that the three genes found to impact SCN resistance exhibit significantly more transcript abundance in roots of SCN-resistant varieties relative to susceptible lines (FIG. 5D and FIG. 7D). In contrast, the transcript abundance for genes immediately flanking the SCN-impacting genes did not differ significantly between SCN-resistant and susceptible varieties (FIG. 5; Glyma18g02600 expression in roots is at or below the limits of detection of qPCR, cDNA cloning and RNAseq methods; See Cook et al. 2012 methods and Severin et al. RNA-Sect Atlas of *Glycine max*: A guide to the soybean transcriptome. Bmc Plant Biology, 2010). Full-length transcripts were confirmed for Glyma18g02580, -2590 and -2610, and no hybrid repeat-junction transcripts were detected for Glyma18g02570 (FIG. 7E). The above suggested that elevated expression of one or more of the SCN-impacting genes could be a primary cause of elevated SCN resistance.

Figure 8:
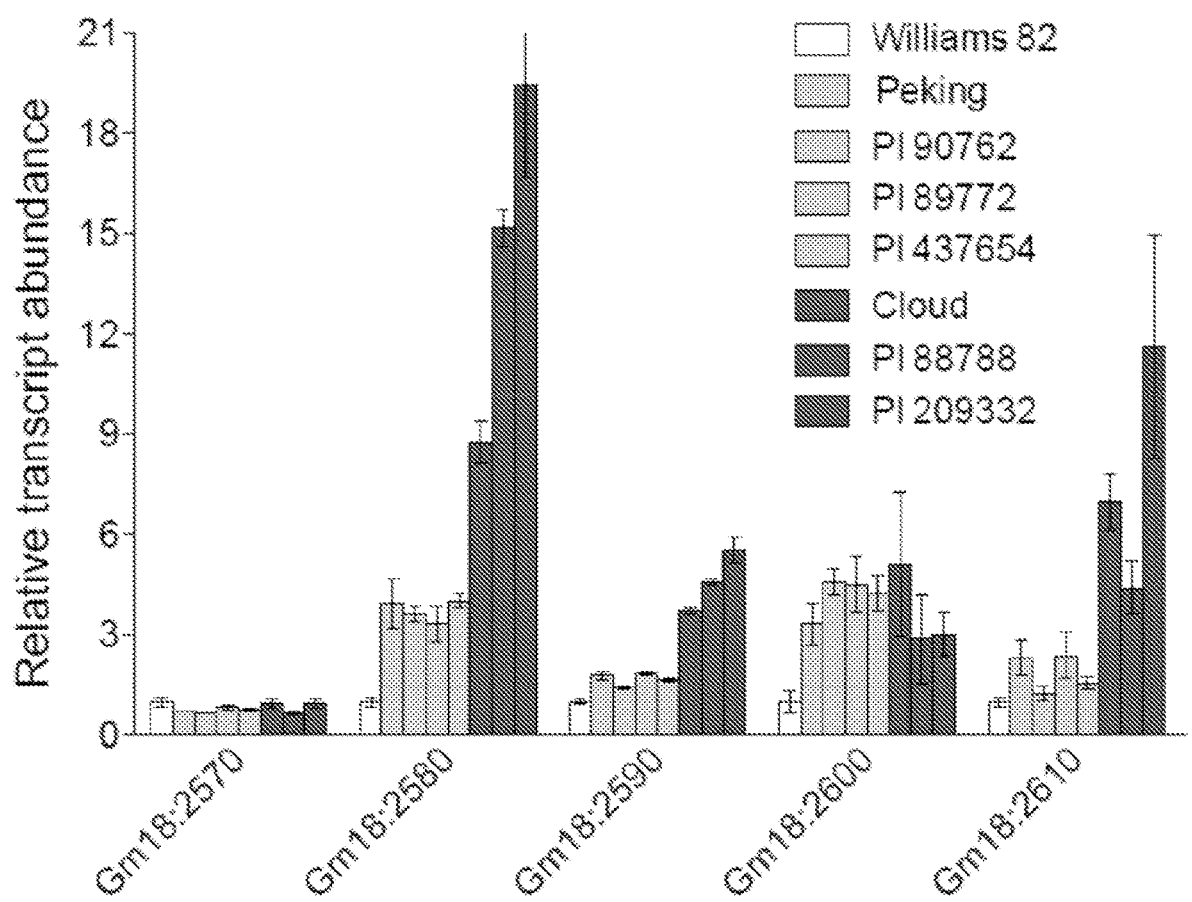
FIG. 8 is a graph showing qPCR for genes in and outside of Rhg1 repeat. RNA collected from roots of 3 individual plants grown in pots, 5 days post emergence. Dark gray bars are estimated to be high copy number lines based on gDNA qPCR and cDNA sequencing. Light grey bars are low copy number containing lines that also require Rhg4 for full resistance.

Quantitative real-time PCR (qPCR) was also used to examine and compare the mRNA transcript abundance of five genes at the Rhg1 locus in non-inoculated roots of the Mg-typing soybean lines. These lines have been established ad accepted by researchers as representing a useful and diverse set of SCN resistant soybean lines (Niblack et al., 2002, J. of Nemat. 34(4): 279-288; T. L. Niblack, K. N. Lambert, G. L. Tylka, 2002, Annu. Rev, Phytopathol. 44:283-303). Transcript abundance for three of the genes, Glyma18g02580, Glyma18g02590, and Glyma18g02610 are all expressed more highly in each of the 7 tested SCN differentials relative to the SCN susceptible line Williams 82 as shown in FIG. 8. Another gene at the locus, Glyma18g02600, was also more highly expressed in the SCN resistant lines, but the data for Glyma18g02600 may be less accurate and the absolute measured transcript level of Glyma18g02600 was near the limit of detection (consistent with published RNA-seq data from soybean roots). As a control, a neighboring, but not duplicated gene, Glyma18g02570 shows similar expression pattern for all tested genotypes. In a separate experiment, two additional genes, (Glyma18g02620 and Glyma18g02630, flanking the repeat to the centromeric side, also show similar transcript abundance across SCN resistant and susceptible tines.

Four of the SCN resistant genotypes (Peking, PI 90763, PI 89772, and PI 437654) are similar to each other in their level of mRNA abundance for the four genes Glyma18g02580, Glyma18g02590, Glyma18g02610, and Glyma18g02600. In these genotypes, transcript abundance is 1.5 to 5 fold higher for the four repeated genes relative to Williams 82. Separately, the SCN-resistant genotypes Cloud, PI 88788, and 209332 are similar to each other in their levels of elevated mRNA abundance for Rhg1 genes compared to Williams 82 and the previous four genotypes. Transcript abundance ranged from 4 to 20 fold higher for the repeated genes in the Cloud, PI 88788, and PI 209332 genotypes. These data show that the increased DNA copy number encoding these four genes increases the transcript abundance. There is also a strong grouping for DNA copy number and transcript abundance, making at least two classes with genotypes Peking, 90763, 89772, and 437654 together, and genotypes Cloud, PI 88788, and 209332 together. We note the correlation of these Rhg1 genotype (copy number) and Glyma18g02580/Glyma18g02590/Glyma18g02610 expression level groupings with the SCN resistance phenotype groupings reported by Colgrove et al. 2008 (Colgrove, A. L., and T. L. Niblack. 2008. Correlation of female indices from virulence assays on inbred lines and field populations of *Heterodera glycines*. Journal of Nematology 40:39-45). While Glyma18g02600 is more highly expressed in SCN resistant lines, there is not a clear relationship between copy number and transcript abundance as found for the other three genes in the repeat. This suggests that increased DNA content does increase transcript abundance, but not in a dosage dependent fashion for Glyma18g02600.

Rhg1 DNA Methylation State is Cultivar-Dependent for Genes within the Duplicated Gene Block.

Figure 9A:
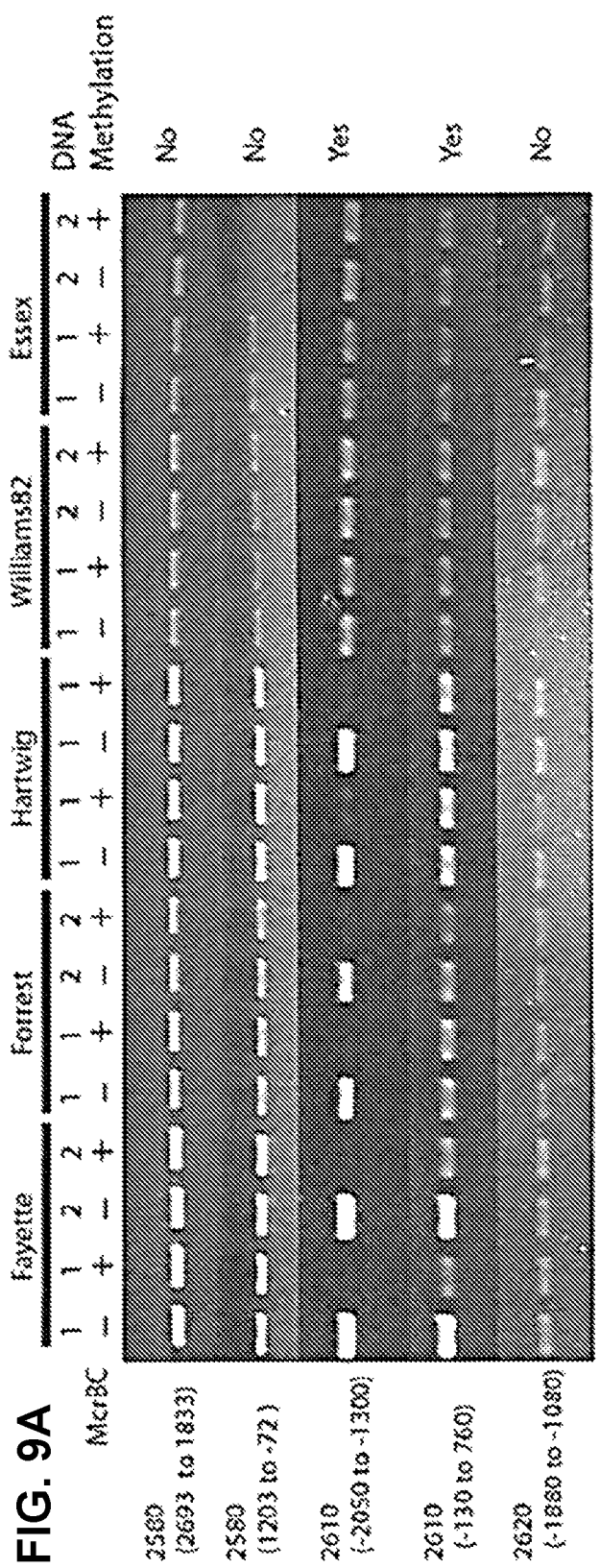
FIG. 9 contains example gel photographs and a table summarizing many experiments showing that resistant and susceptible cultivars have differential DNA methylation at or adjacent to the genes in the duplicated region, especially in the promoter regions. In McrBC experiments, methylated genomic DNA is cleaved by McrBC, which reduces the abundance of the PCR product, while in HpaII experiments, methylated genomic DNA is not cleaved by HpaII and it is the non-methylated DNA that is cleaved, leading to reduced abundance of the PCR product.
Figure 9B:
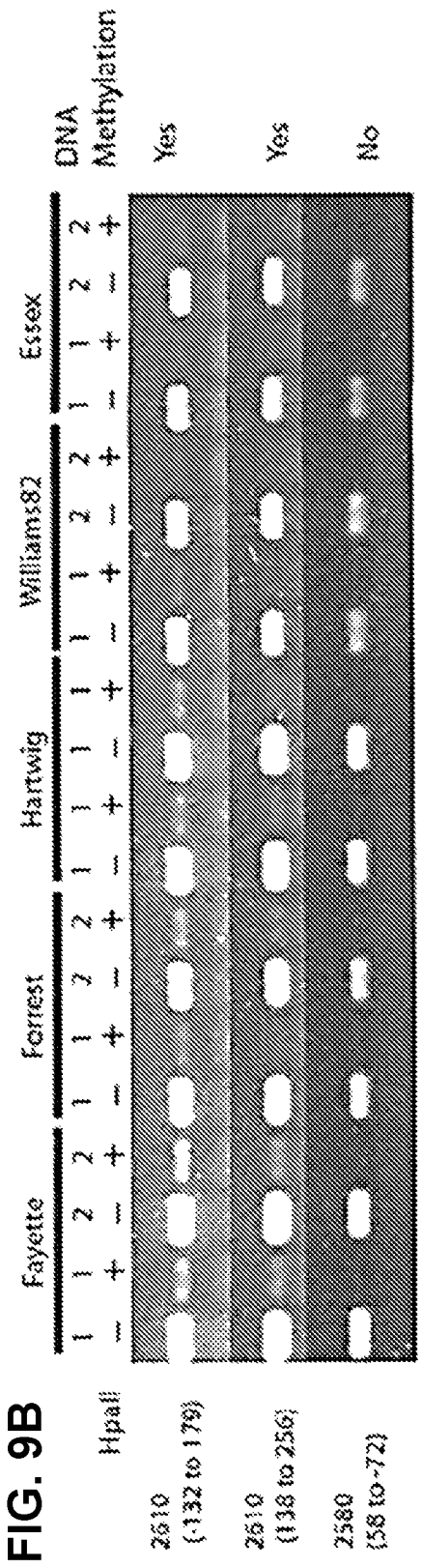

To address the mechanism leading to the observed higher gene expression in SCN-resistant cultivars, we assessed DNA methylation of the Rhg1 locus using methylation sensitive restriction enzyme digestion and PCR. McrBC is an endonuclease that specifically cleaves DNA containing 5-methylcytosine (5-mC) while leaving unmethylated DNA intact. DNA incubated with McrBC and then subjected to PCR fails to produce a product if the product spans methylated cytosines. We identified significant and reproducible differences between SCN-resistant and SCN-susceptible cultivars when soybean genomic DNA was tested for methylation at the Rhg1 locus. For example, three different primer pairs for the Glyma18g02610 promoter or coding regions either failed to amplify a product, or the product was greatly reduced, between McrBC-digested and undigested genomic DNA from resistant cultivars (FIG. 9). The same primer pairs used for PCR with DNA collected from susceptible cultivars produced similar products whether the genomic DNA template had been digested or not, indicating little or no DNA methylation.

Interestingly, a consistent correlation between hypermethylated DNA and elevated gene expression was discovered in the SCN-resistant cultivars tested. The promoter region for Glyma18g02580, Glyma18g02590 and Glyma18g02610 were all methylated and showed higher transcription. A neighboring gene, Glyma18g02620, did not display polymorphic methylation or altered gene expression between resistant and susceptible cultivars (FIG. 9).

Further Characterization of 2580, 2590 and 2610 Genes

Figure 10:
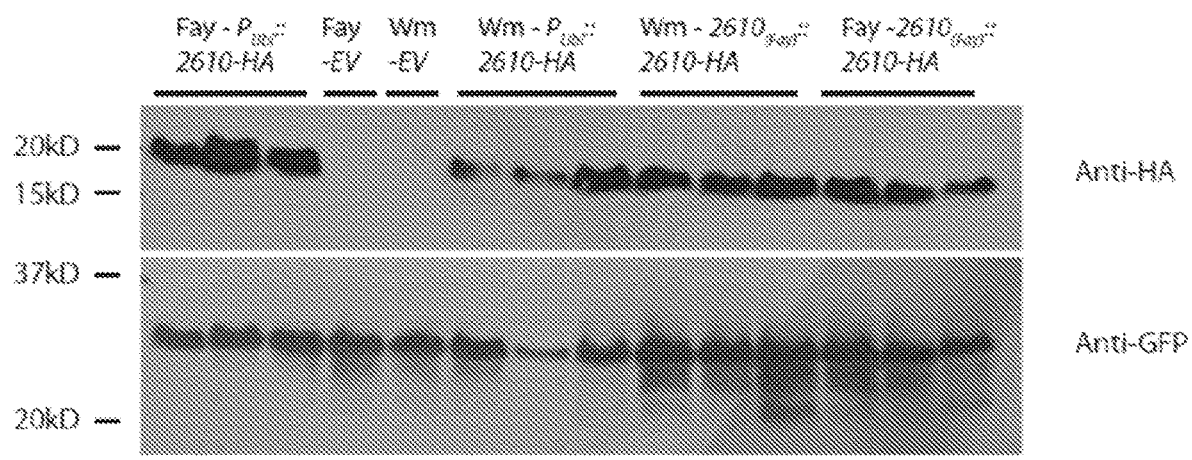
FIG. 10 is a photograph of a Western blot showing that an epitope-tagged version of the Glyma18g02610 protein, produced from an introduced polynucleotide in transgenic roots, is expressed in both Williams 82 and Fayette transgenic roots and the products are similar in size.

RACE PCR for Glyma18g02590 and C/lyrna18g02610 from Fayette (not inoculated with SCN) revealed that the transcripts derived from the SCN-resistant PI88788 haplotype have identical start and stop sites to the annotated transcripts associated with the williams 82 (SCN-susceptible) genome sequence that is available at Phytozome (accessible a www.phytozome.net/). As an initial test for readily detectable protein degradation or post-translational modification differences between SCN-resistant as opposed to SCN-susceptible soybean lines (not inoculated with SCN), protein immunodetection experiments by western blot using 1.5 kb of Fayette native promoter driving Glyma18g02590-HA ($2590_{Fayette}$::2590-HA) or using 3.2 kb of Fayette native promoter driving Glyma18g02610-HA ($2610_{Fayette}$::2610-HA) revealed a detectable protein product that migrated at approximately the predicted size for the respective proteins, and did not reveal protein size differences in Williams 82 as opposed to Fayette (FIG. 10).

To explore the possibility that impacts of Glyma18g02580, Glyma18g02590 and Glyma18g02610 on SCN development in soybean correlate with SCN-inducible gene expression, we analyzed gene expression in excised root tissue from heavily SCN-infested root segments of resistant and susceptible lines. Modest increases in the expression of Glyma18g02580 and Glyma18g02610 were observed in SCN-resistant Fayette, above the high levels of expression already present in non-inoculated Fayette compared to SCN-susceptible Williams 82 (FIG. 11).

To further explore the possibility that impacts of Glyma18g02580, Glyma18g02590 and Glyma18g02610 on SCN development in soybean roots correlate with SCN-inducible expression, promoter-GUS fusion constructs (Prom$_{2580}$::GUS, Prom$_{2590}$::GUS, Prom$_{2610}$::GUS) were made and expressed in transgenic roots. Transgenic roots were stained for GUS activity 5 days after inoculation with SCN (FIG. 12). Prom$_{2580}$::GUS roots had a moderate level of background staining and appeared to have brighter staining of swollen plant vascular tissue at the head of infecting J2 SCN (apparent developing syncytia). Prom$_{2590}$::GUS roots showed very low levels of background staining and consistently greater GUS staining at apparent syncitia, along with strong staining of the tips of emerging lateral roots. Prom$_{2610}$::GUS roots had very high levels of background staining but also appeared to be more highly stained at areas likely to form syncytia. The levels of elevated GUS staining in apparent syncitia were similar to those we observed in positive control promoter-GUS experiments using the previously characterized syncytium-inducible promoter for Glyma14g06080. As noted above, the predicted Glyma18g02610 encoded protein contains a Wound-Induced protein domain (Pfam07107) and a homologous (55% identical) protein in ice plant (*Mesembryanthemum crystallinum*) was shown to be responsive to both biotic and abiotic stimuli. Non-transgenic Fayette soybean plants exposed to MeJA had significantly elevated Glyma18g02610 transcript abundance compared to neighboring genes, further documenting stress-associated expression of this gene (FIG. 11).

Amino acid polymorphism or overexpression of any one of the three identified rhg1-b genes did not account for SCN resistance on its own. From all available rhg1-b sequence reads (across multiple repeat copies), no predicted amino acid polymorphisms relative to Williams 82 were identified for Glyma18g02580, Glyma18g02600 or Glyma18g02610. Some copies of Glyma18g02590 from rhg1-b resemble the Williams 82 sequence, while others contain a set of polymorphisms, notably at the predicted C-terminal six amino acids of the predicted α-SNAP protein (Table 1, confirmed by cDNA sequencing).

The whole-genome sequencing (WGS) data were also analyzed for DNA polymorphisms such as insertions or deletions (INDELs) and single nucleotide polymorphisms (SNPs). In the seven genotypes with an estimated copy number ranging from 9 to 10, a number of SNPs were identified relative to the reference Williams 82 sequence. One gene contained in the repeated rhg1-b segment of DNA, Glyma18g02590, contains DNA polymorphisms relative to Williams 82 as defined above. There is a single SNP, C to A (Williams 82 to PI 88788 derived), at position 1,643,192 that results in a Q to K amino acid substitution. There are 3 SNPs present at the C-terminus, occurring at positions 1,644,965 (G to C), 1,644,968 (G to C), and 1,644,974 (C to A), and a 3 bp insertion after base 1,644,972 (GGC) that collectively change the final 5 amino acids of the Williams 82 protein from EEDLT to QHEAIT. The nucleotide and amino acid sequences are shown in FIG. 13. The 3 bp insertion causes an extra amino acid in the PI 88788 derived lines. All base pair positions correspond to the Williams 82 genome version 1.1, assembly 189. Numerous SNP and INDEL, polymorphisms were observed within the approximate 31 kb Rhg1 repeat DNA region, between Williams 82 and PI 88788-source Rhg1, in the nucleotide regions outside of those that directly comprise the final open reading frame of Glyma18g02580, Glyma18g02590, Glyma18g2600, and Glyma18g02610. Analyses of Illumina sequencing read depth, in the seven soybean lines from the NAM sequencing project with an estimated copy number ranging from 9 to 10, indicated that there were 9 very similar copies of the PI 88788-type repeat at rhg1-b, and one partial copy of a Williams 82-like repeat at rhg1-b.

The soybean line LD01-5907 from the soybean NAM parent sequencing project, which carries an estimated copy number of 3, also contains DNA polymorphisms affecting the amino acid sequence for Glyma18g02590. The DNA polymorphisms are different than those found in PI 88788 derived lines, but occur at similar positions. There is a SNP at position 1,643,225 that results in a D to E amino acid substitution. There are 2 SNPs present at the C-terminus, occurring at positions 1,644,968, (G to T) and 1,644,974 (C to A) and a 3 bp insertion after base 1,644,972 (GGT) that collectively change the final 5 amino acids of the Williams 82 protein from EEDLT to YEVIT. The 3 bp insertion causes an extra amino acid in the Glyma18g02590 protein product in lines with an Rhg1 locus derived from Peking or PI 437654 sources.

The DNA polymorphisms for Glyma18g02590 identified through WGS analysis were confirmed to be expressed using 3' RACE and (DNA sequencing. In SCN resistant genotypes Cloud, PI 88788, and PI 209332, two different Glyma18g02590 transcripts were identified. One of the sequences corresponded to the Williams 82 reference type sequence, and the other corresponded to the sequence from PI 88788-derived resistant sources (from NAM parents). The proportion of PI 88788-derived versus Williams 82-type cDNA sequence follows that observed for DNA sequence. That is, the cDNA of PI 88788 derived Glyma18g02590 is roughly 90% of the total transcripts sequenced. This is consistent with the data that these genotypes contain 8 or 9 copies of the 31 kb DNA segment derived from PI 88788. A SNP present in the 5' UTR of Glyma18g02610 was also analyzed in PI 88788. The proportion of the sequence types fits the other Observations.

In SCN-resistant genotypes Peking, PI 90763, PI 89772, and PI 437654 two different transcripts were identified for Glyma18g02590. One of the sequences corresponds to the sequence from the Peking/PI 437654-derived resistant source LD01-5907 from the NAM sequencing project. See FIG. 13. An alternative form of cDNA was also detected from each of the four SCN-resistant genotypes Peking, PI 90763, PI 89772, and PI 437654, with the same type of polymorphism across all four sources. This apparent mRNA splicing isoform had 36 nucleotides deleted resulting in a Glyma18g02590 isoform with 12 fewer amino acids as shown in FIG. 13. The deletion occurs at the end of exon 6 and splices back into frame in exon 7. None of the sequenced products from Peking, PI 90763, PI 89772, and PI 437654 contained the Williams 82-type Glyma18g02590 sequence, consistent with the WGS analysis. Based on the proportion of cDNAs sequenced, very approximately 70% to 90% of the Glyma18g02590 transcript is the full-length version in these lines.

Figure 14:
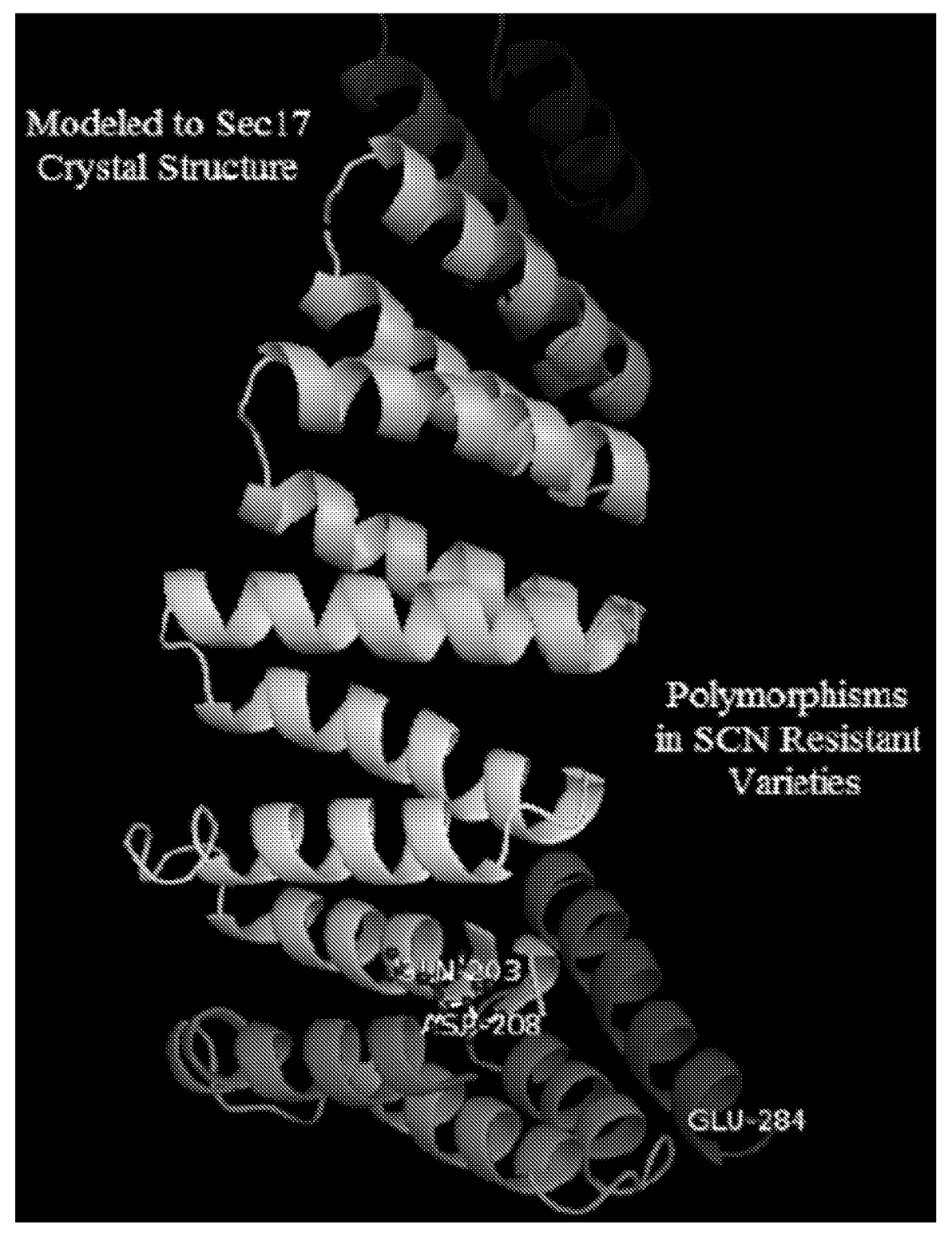

The various polymorphisms may result in functional differences in the Glyma18g2590 polypeptide and are modeled three-dimensionally in FIG. 14 which relies on the solved crystal structure of the yeast Sec17 protein. The deleted alpha-helix is shown in tight gray. It is noted that these polymorphisms are clustered in one general area near the C-terminus of the predicted folded Glyma18g02590, which is an alpha-SNAP protein homolog, and that substantial functional data are available for eukaryote alpha-SNAP proteins that suggest particular functions for this region of the protein (e.g., Barnard R J, Morgan A, & Burgoyne R D (1996) Domains of alpha-SNAP required for the stimulation of exocytosis and for N-ethylmalemide-sensitive fusion protein (NSF) binding and activation. *Molecular biology of the cell* 7(5):693-701; Barnard R J, Morgan A, & Burgoyne R D (1997) Stimulation of NSF ATPase activity by alpha-SNAP is required for SNARE complex disassembly and exocytosis. *J Cell Biol* 39(4):875-883; Jahn R & Scheller R H (2006) SNAREs—engines for membrane fusion. *Nat. Rev. Mol. Cell Biol.* 7(9):631-643.)

However, expressing only the Fayette polymorphic rhg1-b-type Glyma18g02590 downstream of a strong constitutive promoter or native promoter sequence did not increase the SCN resistance reaction of Williams 82 transgenic roots (FIG. 15 and FIG. 16), suggesting that rhg1-b SCN resistance requires more than this 2590 amino acid polymorphism. But such polymorphisms may play a contributing rote SCN resistance that was not detected in these experiments. Overexpression of Glyma18g02580 or Glyma18g02610 also failed to increase SCN resistance (FIG. 13) when expressed alone using a strong constitutive promoter. These data are preliminary and may indicate that the resistance phenotype requires more than a single gene or that some other factor is necessary to mediate resistance.

Figure 16A:
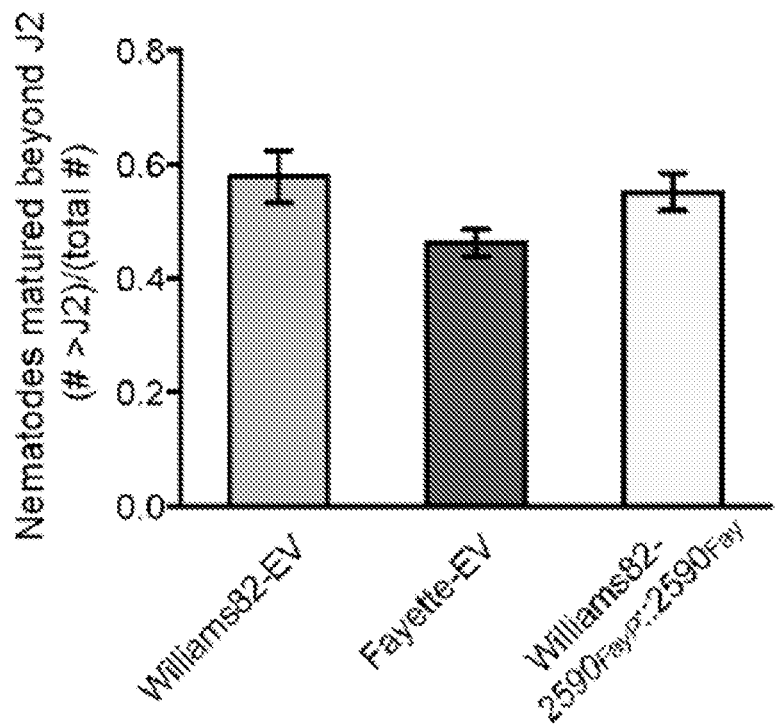
FIG. 16A-16B is a set of graphs showing that expressing the native Fayette Glyma18g02590 allele in Williams 82 does not alter SCN development.
Figure 16B:
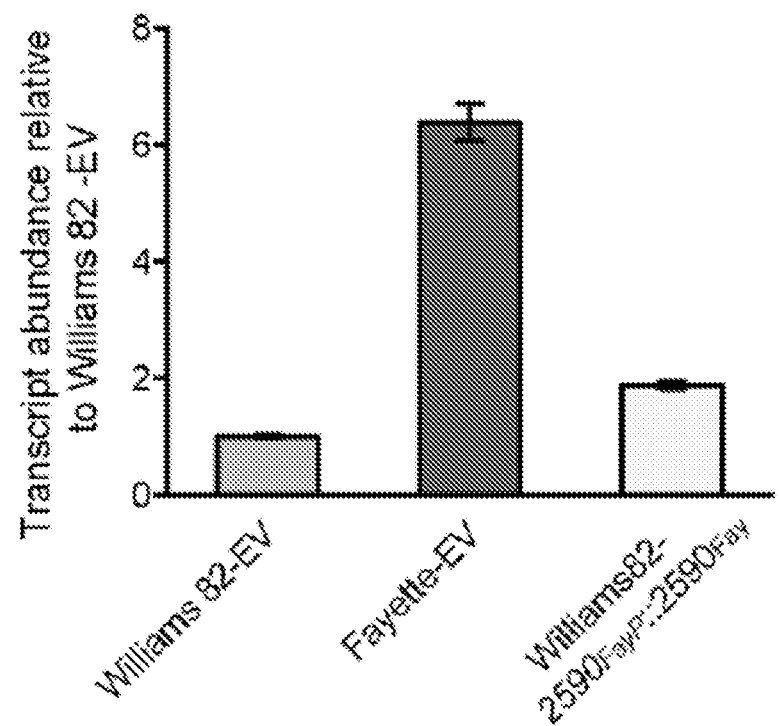
Figure 17:
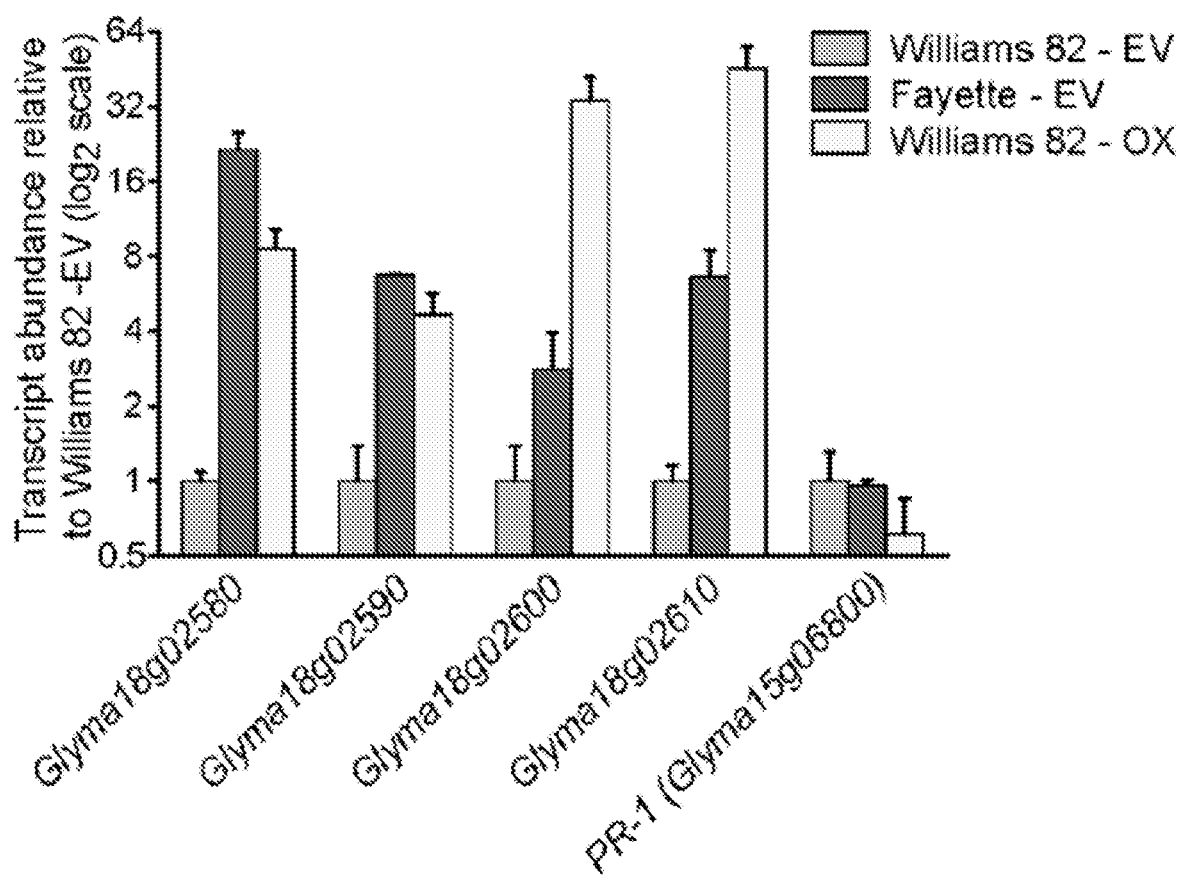
FIG. 17 is a graph showing that qPCR reveals elevated transcript abundance of the intended genes in roots transformed with the multiple gene simultaneous overexpression construct of FIG. 15, and no significant elevation of PR-1 expression. Transgenic roots carried either the multiple-gene construct (OX) or empty vector (EV). Similar results obtained in second independent experiment with different transgenic events, except PR-1 abundance was more similar (closer to 1.0) between Williams 82-EV, Fayette-EV and Williams-OX roots in second experiment. Bars represent mean±std. error of mean. Data for Glyma18g02600 are less dependable for Williams-EV and Fayette-EV because their qPCR signal was at the limit of accurate qPCR detection (CT>33).

Given the above, simultaneous overexpression of the set of genes within the 31 kb repeat segment was tested as a possible source of SCN resistance. A single recombinant DNA construct was made in which each of the genes Glyma18g02580, Glyma18g2590, Glyma18g2600 and Glyma18g2610 was fused to a strong promoter. In two separate experiments that together tested >25 independent transgenic events for each DNA construct, resistance to SCN was significantly increased in SCN-susceptible Williams 82 by simultaneous overexpression of this set of genes (FIG. 15). Increased SCN resistance was conferred despite the fact that three of the genes being overexpressed encode predicted amino acid products identical to those of SCN-susceptible Williams 82, and the polymorphic Fayette rhg1-b Glyma18g02590 gene that was used was not sufficient to cause a detectable change in SCN resistance when overexpressed on its own (FIG. 15). Of note, there was no significant elevation of PR-1 in these transgenic roots, which could have indicated non-specific elevation of defenses (FIG. 16). We also tested the impact of simultaneously over-expressing Glyma18g02580, Glyma18g02590$_{Fayette}$, and Glyma18g02610 on SCN resistance in Williams 82. We observed increased resistance to SCN transgenic roots of Williams 82 over-expressing Glyma18g02580, Glyma18g-02590$_{Fayette}$, and Glyma18g02610 relative to Williams 82 empty vector roots as shown in FIG. 17. These data indicate that over-expressing this combination of genes results in enhanced SCN resistance.

These results reveal a novel mechanism for disease resistance: an expression polymorphism for multiple disparate but tightly linked genes, derived through copy number variation at the Rhg1 locus. This knowledge suggests future approaches to enhance the efficacy of Rhg1-mediated quantitative resistance to the highly important SCN disease of soybean, for example through isolation of soybean lines that carry more copies of the 31 kb Rhg1 repeat, or through transgenic overexpression of the relevant genes. These approaches may be applicable in other species as well, for resistance to other endoparasitic nematodes.

The biochemical mechanisms of Rhg1-mediated resistance remain unknown. Other sequenced plant genomes do not carry close homologs of the predicted Glyma18g02610 protein, although a wound-inducible protein in ice plant with 55% identity has been studied. Modeling of the Glyma18g02610 predicted tertiary structure using Phyre2 indicated, with 98% confidence, similarity of 48% of Glyma18g02610 to the PhzA/B subfamily of Delta(5)-3-ketosteroid isomerase/nuclear transport factor 2 family proteins. Hence Glyma18g02610 may participate in the production of phenazine-like compounds that are toxic to nematodes. Thus application of Glyma18g2610 to plants, soil or seeds may inhibit nematodes in susceptible plants. Secretion of the Glyma18g02610 protein or other plant products that contribute to disease resistance may be impacted by the Glyma18g02590 α-SNAP protein. Because it is one of at least five α-SNAP homologs encoded in the soybean reference genome, Glyma18g02590 may have undergone subfunctionalization or neofunctionalization. Fully sequenced plant genomes carry from two dozen to over five dozen annotated amino acid transporters of many subtypes which can be involved in amino acid import and/or export between cells or between subcellular organelles. The Glyma18g02580 protein and its most closely related transporters of soybean and other species are not functionally well-characterized, so the concept that Glyma18g02580 alters nematode success by altering the levels of specific amino acids or amino acid derivatives at the feeding site is only one of many viable hypotheses for future study regarding the SCN-deterring function of Glyma18g02580.

Copy number variation (CNV) of a block of dissimilar genes, rather than CNV for a single gene family, confers Rhg1-mediated SCN resistance. Recent analyses of genome-architecture in sorghum, rice, and soybean have reported high levels of CNV, and a tendency for overlap of regions of CNV with postulated biotic and abiotic stress-related genes. The present work provides a concrete example of CNV conferring a valuable disease resistance trait. In humans and insects, adaptive traits have been associated with CNV for specific single genes. Single-copy clusters of functionally related but non-homologous genes are highly unusual in multicellular eukaryotes, but these have been reported in association with plant secondary metabolism. We provide a unique example of CNV involving more than two repeats, with the repeat encoding multiple gene products that are necessary for adaptation to the same important environmental constraint. Given the highly repetitive nature and plasticity of plant genomes and the relatively underexplored association between CNV and phenotypes, it seems likely that a number of other complex traits are controlled by the general type of CNV we report for soybean Rhg1.

Materials and Methods:

*Agrobacterium rhizogenes* Soybean Root Transformation

*A. rhizogenes* strain Arqua1 was transformed by freeze-thaw as previously reported by Wise, A. A., Z. Liu, and A. N. Binns, Three methods for the introduction of foreign DNA into *Agrobacterium*. Methods Mol Biol, 2006, 343: p, 43-53 and Hofgen, R. and L. Willmitzer, Storage of competent cells for *Agrobacterium* transformation. Nucleic Acids Research, 1988. 16(20): p. 9877-9877. The cells were plated on selective media with the appropriate antibiotic and incubated at 28° C. for two days. *A. rhizogenes* strain Arqua1 was received from Dr. Jean-Michel Ane, University of Wisconsin Madison. Soybean seeds lacking macroscopic signs of fungal or viral contamination were surface-sterilized for 16-20 h in a desiccator jar with chlorine gas generated by adding 3.5 ml 12N HCl into 100 ml household bleach (6% sodium hypochlorite). At least 20 seeds per experiment were plated onto germination media (Gamborg's B5 salts (3.1 g/L), 2% sucrose, 1× Gamborg's B5 vitamins, 7% Noble agar, pH 5.8) in 100×25 mm Petri plates. Plates were wrapped with Micropore tape (3M, St. Paul, Minn.) and incubated at 26° C. in a growth chamber (18/6 light/dark hours) for approximately one week. Soybean cotyledons were harvested 5-7 days after germination by gently removing them from the hypocotyls with sterile forceps. With a sterile forceps and Falcon #15 scalpel, several shallow slices were made across the abaxial surface of the cotyledons after dipping the scalpel in *A. rhizogenes* suspension ($OD_{600}$ 0.6-0.7 in sterile $ddH_2O$). The cotyledons were then placed abaxial-side down on a co-culture medium (CCM) (0.31 g/L Gamborg's B5 salts, 3% sucrose, 1× Gamborg's B5 vitamins (BioWorld, Dublin Ohio), 0.4 g/L L-cysteine, 0.154 g/L dithiothreitol, 0.245 g/L sodium thiosulfate, 40 mg/L acetosyringone, 5% Noble agar, pH 5.4) in 100×15 mm Petri plates with a piece of 70 min filter paper (Whatman, Piscataway, N.J.) on the surface of the agar to prevent *A. rhizogenes* from overgrowing. Plates were wrapped with parafilm and incubated in the dark at room temperature for three days. The explants were then transferred to a hairy root medium (HRM) of 4.3 g/L MS salts (Sigma Co., St. Louis, Mo.), 2% sucrose, 1× Gamborg's 85 vitamins (BioWorld, Dublin, Ohio), 7% Noble agar, 0.15 g/L cefotaxime, 0.15 g/L carbenicillin, pH 5.6 in 100×15 min Petri plates, wounded side up. Plates were wrapped with Micropore tape and incubated in the dark at room temperature until roots emerged, usually in around 2 weeks. Transgenic soybean roots were detected based on plasmid vector-encoded GFP expression, using a fluorescence stereomicroscope (LEICA MZ FL III with GFP2 filter). Transgenic soybean root tip segments (2-3 cm were transferred to HRM. Roots that were expressing incomplete strips of fluorescence (chimeras) or exhibiting overall low levels of GFP fluorescence were avoided. Independent transgenic events, generated from different inoculation sites or different cotyledons, were maintained separately for RNA extraction and nematode demographic assays.

Nematode Maintenance

An SCN population from Racine, Wis. (Hg type 7), collected by Ann MacGuidwin (University of Wisconsin-Madison), was maintained on the susceptible soybean cultivar Williams 82. Seeds were germinated between two damp pieces of paper towel that were rolled-up and placed vertically in a glass beaker with a small amount of water at the bottom for 2-4 days. Germinated seeds were then planted in autoclaved 4:1 sand:soil mixture and inoculated with 2000 eggs of a *H. glycines* per plant, and grown in a 28° C. growth chamber. Cysts were collected ~50 days after infection when soybeans were at R2 (full (lowering) and extracted from soil and roots using sieves and centrifugation. Briefly, soil and roots from infected pots was placed in a pitcher of water and agitated. The soil-cyst-water slurry was passed over a 710 μm-250 μm sieve tower, and the mixture from the 250 μm sieve was backwashed into a 50 mL plastic conical tube. The tubes were centrifuged at 2000 rpm for 4 minutes then the supernatant was poured off. A 60% sucrose solution was added to the tubes, stirred, and centrifuged at 2000 rpm for 2 min. Cysts in the supernatant were then collected over a 250 μm sieve. Collected cysts were stored at 4° C. sealable plastic bags containing twice-sterilized flint sand.

Nematode Demographics Assay

Nematode demographics assays were performed as in Melito et al, infra. Vigorous new root segments (2-3 cm including root tip) were utilized. All roots (all genotypes within an experiment) were coded with a random number prior to inoculation, to mask root genotype information from the investigators who stained roots two weeks later and determined the number of nematodes in each nematode development category. For inoculum, *H. glycines* eggs were collected by breaking open cysts with a large rubber stopper and collecting the eggs on a sieve stack consisting of 250 μm-75 μm-25 μm sieves (USA Standard Testing Sieve). Eggs were collected from the 25 μm sieve and rinsed. Eggs were placed in a hatch chamber with 3 mM ZnCl₂ for hatching at room temperature in the dark for 5-6 days. See Wong, A. T. S., G. L. Tylka, and R. G. Hartzler, Effects of 8 herbicides on in-vitro hatching of Heterodera-glycines. Journal of Nematology, 1993. 25(4): p. 578-584. Hatched nematodes were surface-sterilized for 3 min in 0.001% mercuric chloride and washed three times with sterile distilled water, then suspended in room temperature 0.05% low-melting point agarose to facilitate even distribution. Baum, T. J., M. J. E. Wubben, K. A. Hardy, H. Su, and S. R. Rodermel, A screen for *Arabidopsis thaliana* mutants with altered susceptibility to *Heterodera schachtii*. Journal of Nematology, 2000. 32(2): p. 166-173. The number of active nematodes was determined by viewing an aliquot under a stereomicroscope at least one-half hour after surface-sterilization and washing, and 200-250 active J2s were inoculated onto each fresh root segment. Inoculated roots with nematodes were maintained on HRM media, at 28° C.; substantial root growth typically occurred during the subsequent two weeks. Nematode infection and development within these root systems was monitored by clearing and staining with acid fuchsin, typically 15 days post inoculation (dpi), Bybd, D. W., T. Kirkpatrick, and K. R. Barker, An improved technique for clearing and staining plant-tissue for detection of nematodes. Journal of Nematology, 1983. 15(1): p. 142-143. The nematode demographic assay was then completed by recording the number of nematodes in each root system that exhibited a morphology resembling either J2 (thin), J3 (sausage-shaped), elongated male, or J4/adult female nematodes, as noted in text and figures. Typically, 20-80 nematodes were present in each root; roots containing fewer than ten nematodes were excluded from further analysis. Results were expressed as % of nematodes that had developed beyond J2 stage ([J3+adult males+adult females]/[J2+J3+adult males+adult females]). Each data point was normalized to the mean for Williams 82 roots transformed with empty vector, from the same experiment. All reported data are based on at least two independent biological replicate experiments 12 independently transformed roots for each bar on a bar graph).

Primer Table

Primer sequences used to perform this research are listed in Table 4 and referred to by number in this document.

TABLE 4

DNA sequences of oligonucleotide primers used for PCR (3 pages).

| Primer | Sequence | SEQ ID NO: |
|---|---|---|
| Silencing constructs | | |
| 2570 hpRNAi _F | AGGATCCATTTAAATCAAGTACTCTTCCC CACAAAAGCT | 19 |
| 2570 hpRNAi _R | ACCTAGGAGGCGCGCCTGGGGCCATTTCA GTAATTAGGTC | 20 |
| 2580 hpRNAi _F | acctaggaggcgcgccTCATGAAGGTTCT CGGCGTAG | 21 |
| 2580 hpRNAi _R | aggatccatttaaatCCACCAGTGAATTC CAAACCA | 22 |
| 2590 hpRNAi _F | GAcctaggcgcgccGGACTTGGTCGTCAA CACAGTC | 23 |
| 2590 hpRNAi _R | GCggatccatttaaatGAGCAGCAAACTG GGCAACT | 24 |
| 2600 hpRNAi _F | acctaggaggcgcgccGCCAAATTCAAAA GGCTTGCT | 25 |
| 2600 hpRNAi _R | aggatccatttaaatCACCATTCAACATG CCTGTCA | 26 |
| 2610 hpRNAi _F | taacctaggaggcgcgccACAACTCCTTC CGATTCGTTCCG | 27 |
| 2610 hpRNAi _R | caggatccatttaaatAGATACAACCACC TGAATACGCCC | 28 |
| 2620 hpRNAi _F | AGGATCCATTTAAATCTCGCAACACCATA TCCAGAGTA | 29 |
| 2620 hpRNAi _R | ACCTAGGAGGCGCGCCGGTGTTAAGGTCG AACCTGCGAA | 30 |
| 2590-1 I miR-s | gaTATTGGTTATAGCAACACCGTtctctc ttttgtattcc | 31 |
| 2590-1 II miR-a | gaACTTTGCTATAACCAATAtcaaagaga atcaatga | 32 |
| 2590-1 III miR*s | gaACAGTGTTGCTATTACCAATTtcacag gtcgtgatatg | 33 |
| 2590-1 IV miR*a | gaAATTGGTAATAGCAACACTGTtctaca tatatattcct | 34 |
| 2610-1 I miR-s | gaTATTTCCCGACCCGACGGGACtctctc ttttgtattcc | 35 |
| 2610-1 II miR-a | gaGTCCCGTCGGGTCGGGAAATAtcaaag agaatcaatga | 36 |
| 2610-1 III miR*s | gaGTACCGTCGGGTCCGGAAATTtcacag gtcgtgatatg | 37 |
| 2610-1 IV miR*a | gaAATTTCCGGACCCGACGGTACtctaca tatatattcct | 38 |
| 2610-2 I miR-s | gaTATCCAGTCACCGCGACGTGGtctctc ttttgtattcc | 39 |
| 2610-2 II miR-a | gaCCACGTCGCGGTGACTGGATAtcaaag agaatcaatga | 40 |
| 2610-2 III miR*s | gaCCCCGTCGCGGTGTCTGGATTtcacag gtcgtgatatg | 41 |
| 2610-2 IV miR*a | gaAATCCAGACACCGCGACGGGGtctaca tatatattcct | 42 |
| Transcript Abundance using qPCR | | |
| gm18: 2570 F_qPCR | TGAGATGGGTGGAGCTCAAGAAC | 43 |
| gm18: 2570 R_qPCR | AGCTTCATCTGATTGTGACAGTGC | 44 |
| gm18: 2580 F_qPCR | CGTGTAGAGTCCTTGAAGTACAGC | 45 |
| gm18: 2580 R_qPCR | ACCAGAGCTGTGATAGCCAACC | 46 |
| gm18: 2590 F_qPCR | TCGCCAAATCATGGGACAAGGC | 47 |

TABLE 4-continued

DNA sequences of oligonucleotide primers used for PCR (3 pages).

| Primer | Sequence | SEQ ID NO: |
|---|---|---|
| gm18: 2590 R_qPCR | CAATGTGCAGCATCGACATGGG | 48 |
| gm18: 2600 F_qPCR | GCTTCAGTCAAGAAAATGTGCATG | 49 |
| gm18: 2600 R_qPCR | CACCCGAAACCGCGACACAAATG | 50 |
| gm18: 2610 F_qPCR | AGGTCACGTGTTGCCGTTG | 51 |
| gm18: 2610 R_qPCR | AAACCACACCAATAACAACAAAGCTCT | 52 |
| gm18: 2620 F_qPCR | AAGCCCAACAGGCCAAAGAGAG | 53 |
| gm18: 2620 R_qPCR | ACACCAAATGGGTTCGCACTTC | 54 |
| gm18: 2630 F_qPCR | TTGTGGAAGTGAAAGTCGGTTTGC | 55 |
| gm18: 2630 R_qPCR | GTTGTCACGTTTCCCGTAACAATG | 56 |
| EF1b_For.qRT | CCACTGCTGAAGAAGATGATGATG | 57 |
| EF1b_Rev.qRT | AAGGACAGAAGACTTGCCACTC | 58 |
| SKIP16_For.qRT | GAGCCAAGACATTGCGAGAG | 59 |
| SKIP16_Rev.qRT | CGGAAGCGGAAGAACTGAACC | 60 |
| UKN2_For.qRT | GCCTCTGGATACCTGCTCAAG | 61 |
| UKN2_Rev.qRT | ACCTCCTCCTCAAACTCCTCTG | 62 |
| ACT11_For.qPCR | ATCTTGACTGAGCGTGGTTATTCC | 63 |
| ACT11_Rev.qPCR | GCTGGTCCTGGCTGTCTCC | 64 |
| UNK1_For.qPCR | TGGTGCTGCCGCTATTTACTG | 65 |
| UNK1_Rev.qPCR | GGTGGAAGGAACTGCTAACAATC | 66 |
| TIP41_For.qPCR | AGGATGAACTCGCTGATAATGG | 67 |
| TIP41_Rev.qPCR | CAGAAACGCAACAGAAGAAACC | 68 |
| PR-1 (6790) F | TGCTTGGTCACCTGGAAGTTGG | 69 |
| PR-1 (6790) R | AACTTCCTGCGAGCTGCGATAC | 70 |
| PR-1 (6800) F | AGTCATTGTGGGTGATCATGCTG | 71 |
| PR-1 (6800) R | GCAGCGTTGTGTGCATTAACAAG | 72 |
| Expression Vectors | | |
| Ox2610-SalF2 | gtcgacATGCGCATGCTCACCGG | 73 |
| P2610fused-R | TATTGCGAGAACCAAACCGG | 74 |
| Ox2590Sal-F | GGgtcgacATGGCCGATCAGTTATCGAAGG | 75 |
| Ox2590fused-R | AGTAATAGCCTCATGCTGCTCAAGTT | 76 |
| TerXba-R | ACtctagaGCGCATGTCTTGCGTTGATG | 77 |
| GmubiXba-F | GCtctagaGGGCCCAATATAACAACGACG | 78 |
| TerKpn-R | TCggtaccGCGCATGTCTTGCGTTGATG | 79 |
| PPA Linker_Top | GatgtcTTAATTAAatatctgtGGGCCCactatGGCGCGCCaatgtaaA | 80 |
| PPA Linker_Bottom | AGCTTttacattGGCGCGCCatagtGGGCCCacagataTTAATTAAgacatCTGCA | 81 |
| Ox2600-F | ATGGTTTCGGTTGATGATGGG | 82 |
| Ox2600-R | TTTTTGTGCATATAAGGGGTTCAT | 83 |
| NosHind-F | GCaagcttGATCATGAGCGGAGAATTAAGGG | 84 |
| Nos2600-R | CCCATCATCAACCGAAACCATAGATCCGGTGCAGATTATTTGG | 85 |
| Nos2600-F | CCAAATAATCTGCACCGGATCTATGGTTTCGGTTGATGATGGG | 86 |
| NosAsc-R | TCggcgcgccGCGCATGTCTTGCGTTGATG | 87 |
| Ox2580-F | ATGTCTCCGGCCGCCG | 88 |
| Ox2580-R | TGACTTGCTACTAAAAGCATTATATATGTTG | 89 |
| NosAsc-F | CAggcgcgccGATCATGAGCGGAGAATTAAGGG | 90 |
| Nos2580-R | CGGCGGCCGGAGACATAGATCCGGTGCAGATTATTTGG | 91 |
| Nos2580-F | CCAAATAATCTGCACCGGATCTATGTCTCCGGCCGCCG | 92 |
| NosSbf-R | TGcctgcaggGCGCATGTCTTGCGTTGATG | 93 |
| M13 F | GTAAAACGACGGCCAG | 94 |
| M13 R | CAGGAAACAGCTATGAC | 95 |
| pSM101 seq | GTCTTGATGAGACCTGCTGCG | 96 |
| g2590pHind-F | CTTaagcttGAATGGTTTTTGTTTTGTTGTCTCTCAC | 97 |
| g2590pSal-R | TTGGTCGACCGTATCATCCAATG | 98 |
| Bridge PCR | | |
| SCN_Res Bridge F | TTTAGCCTGCTCCTCACAAATTC | 99 |
| SCN_Res Bridge R | TTGGAGAATATGCTCTCGGTTGT | 100 |
| Probes for Northern Analysis and Alt Transcript | | |
| 2570F_qPCR | TGAGATGGGTGGAGCTCAAGAAC | 101 |
| 2570 UTR Rev | CAAGTACTCTTCCCCACAAAAGC | 102 |
| 2570 put exon F | TGCAGTTTTAGTGGAAAGGCC | 103 |
| 2570 exon 6 R | TCATCAAGCTCAACTTGAATCCC | 104 |

TABLE 4-continued

DNA sequences of oligonucleotide primers used for PCR (3 pages).

| Primer | Sequence | SEQ ID NO: |
|---|---|---|
| RACE PCR | | |
| 2590-5GSP | GATCGGCCATTTTCCTCCGATCGAAACA | 105 |
| 2590-5NGSP | GACGACCAAGTCCAAATCCAAAACCCGC | 106 |
| 2590-3GSP | AAGCCAAAGAACTTGAGCAGCATGAGGC | 107 |
| 2590-3NGSP | CTGTCCAGTTGTTCGTCTTACACATCCA | 108 |
| 2610-5GSP | GGCGACGATCTTGACGACGGCGTT | 109 |
| 2610-5NGSP | TCATACAGTGCAACCACCAGCCGCG | 110 |
| 2610-3GSP | GGACGAGGTCACGTGTTGCCGTTGCT | 111 |
| 2610-3NGSP | TTCACCACTATGGGCGTATTCAGGTGGT | 112 |
| 2580-3GSP | CCTGGGGGATTCCAAAGGAACGC | 113 |

Vector Construction for Soybean Transformation

Binary vectors pSM101 and pSM103 for soybean transformation were constructed as previously described in Melito et al. To generate and clone soybean amiRNAs, the Web microRNA Designer (wmd3.weigelworld.org) and protocols were used. The concept is more thoroughly documented in other references. See Schwab, R., S. Ossowski, M. Riester, N. Warthmann, and D. Weigel, Highly specific gene silencing by artificial microRNAs in *Arabidopsis*. Plant Cell, 2006. 18(5): p. 1121-1133. Soybean DNA was extracted from either expanding soybean trifoliates or soybean roots using a previously reported CTAB method. Doyle, J. J. and E. E. Dickson, Preservation of plant-samples for DNA restriction endonuclease analysis. Taxon, 1987. 36(4): p. 715-722. PCR fragments for amiRNA construction were TA cloned using pCR8/GW/TOPO TA cloning kit (Life Technologies Corp., Carlsbad Calif.) (Table 4 13-24). Binary vectors pGRNAi1 and pGRNAi2 for soybean transformation were a gift from Wayne Parrot, University of Georgia (unpublished). For each hairpin, a 300-600 bp DNA fragment was PCR amplified (Table 4 1-12) using Phusion HF polymerase (New England Biolabs, Ipswich, Mass.) and iScript cDNA synthesis kit (Biorad, Hercules, Calif.) as a template, as per manufacturer's instructions. PCR products were TA cloned as previously described. Primers used to generate the DNA fragments were designed to contain restriction sites AvrII/AscI (forward primer) and BamHI/SwaI (reverse primer) to allow cloning into pGRNAi1 and pGRNAi2. To generate the first arm of the hairpin, the insert and vector were sequentially digested with restriction endonucleases SwaI and AscI using manufacturer's recommended protocol (New England Biolabs, Ipswich, Mass.). DNA was separated on a 1.0% agarose gel stained with ethidium bromide, and respective DNA fragments were gel purified using Qiaquick gel extraction kit (Qiagen, Valencia, Calif.) and ligated together overnight at 4° C. using T4 DNA ligase (Promega, Madison, Wis.). The same procedure was used to insert the second arm of the hairpin construct using the restriction endonucleases BamHI and AvrII. To construct single gene overexpression vectors for Glyma18g02580 (Table 4 70, 71), Glyma18g02590 (Table 4 57, 58) and Glyma18g02610 (Table 4 55, 56), full-length ORFs were PCR amplified from cDNA of Fayette using Phusion HF polymerase and TA cloned in pCR8/GW/TOPO as previously described. Glyma18g02600 (Table 4 67, 68) was cloned from genomic DNA by similar methods, as no Glyma18g02600 cDNA could be detected in root cDNA libraries. The Glyma18g02610 and Glyma18g02590 ORFs were recombined with pGWB14 (CaMV 35S promoter, 6×HA-NOS terminator) using LR clonase reaction (Life Technologies Corp., Carlsbad, Calif.) per manufactures instructions. See Nakagawa, T., T. Kurose, T. Hino, K. Tanaka, M. Kawamukai, Y. Niwa, K. Toyooka, K. Matsuoka, T. Jinbo, and T. Kimura, Development of series of gateway binary vectors, pGWBs, for realizing efficient construction of fusion genes for plant transformation. J Biosci Bioeng, 2007. 104(1): p. 34-41. Glyma18g02610 (Table 4 55, 59) was PCR amplified from pGWB14 and TA cloned into pCR8. This vector and pSM103 were digested with XbaI/KpnI and ligated to yield GmUbi$_{prom}$:2610-HA:NOS-$_{term}$ (OE:2610-HA). The same procedure was used for Glyma18g02590 (Table 4 57, 59), except the amplicon contained XbaI/SalI sites and was TA cloned into pCR8. 2590-HA:NOS$_{term}$ and pSM103 were digested with XbaI/SalI and ligated to yield GmUbi$_{prom}$:2590-HA:NOS$_{term}$ (OE:2590-HA). The full OE:2590-HA was also digested (XbaI/SalI) and ligated into pSM103 containing OE:2610-HA to yield OE:2610-OE:2590. To generate the four gene overexpression construct, the restriction sites PacI, PspOMI, and AscI were added to pSM101 between sites PstI/HindII by annealing oligos (Table 4 62, 63) to generate pSM101+. The two gene overexpression cassette (OE:2610-OE:2590) was moved to the new pSM101+ using the restriction enzymes PstI/KpnI and ligation. A Nos promoter was added to Glyma18g02600 in pCR8 using overlap PCR (Table 4 65-68) and TA cloned into pCR8. This vector was recombined with pGWB16 (no promoter, 4xMyc-NOS terminator) in an LR clonase reaction to yield Nos$_{prom}$:2600-myc:Nos$_{term}$ (OE:2600-myc). OE:2600-myc was PCR amplified (Table 4 66, 72) and TA cloned into pCR8, and subcloned into pSM101+(OE:2610-OE:2590) using restriction enzymes HinIII/AscI to yield the three gene overexpression vector (OE:2610-OE:2590-OE:2600). A Nos promoter was added to Glyma18g02580 in pCR8 using overlap PCR with primers 71-74 and TA cloned into pCR8. This vector was used with pGWB16 in an LR clonase reaction to yield Nos$_{prom}$:2580-myc:Nos$_{term}$ (OE:2580-myc). OE:2580-myc was amplified (Table 4 72, 75) and TA cloned, then subcloned into the three gene overexpression vector resulting in the four gene overexpression vector pSM101+0E:2610-OE:2590-OE:2600-OE:2580. The native Fayette Glyma18g02590 (2590$_{FayP}$:2590$_{Fay}$) construct for Williams 82 complementation was subcloned from a fosmid containing the desired allele. A 6.5 kb DNA fragment containing the PI 88788 Glyma18g02590 was isolated from a fosmid following SalI digestion and cloned into pSM101 using the SalI restriction site. This sequence contained approximately 1 kb of 5' regulatory DNA sequence. An additional 600 bp of 5' regulatory sequence directly upstream of the subcloned region was added to the construct by amplifying a PCR product (Table 4 79, 80) from the fosmid and inserted using the restriction enzymes HindIII/SalI. The resulting construct contained approximately 1.6 kb of naturally occurring 5' regulatory sequence of the Fayette Glyma18g02590 allele. Vector sequences were confirmed at various steps using Sanger sequencing with ABI Big Dye cycle sequencing kit (dideoxy chain-termination) and ABI 3730×1 DNA Analyzers (Life Technologies Corp., Carlsbad, Calif.), using the DNA sequencing service at the University of Wisconsin-Madison Biotechnology Center.

TABLE 5

Amino acid sequences for Glyma18g2580, Glyma18g2590, Glyma18g2600 and Glyma18g2610

>Glyma18g02580.1|PACid: 16307711

(SEQ ID NO: 1)
MSPAAGVSVPLLGDSKGTPPPASVPGAVFNVATSIVGAGIMSIPAIMKVL
GVVPAFAMILVVAVLAELSVDFLMRFTHSGETTTYAGVMREAFGSGGALA
AQVCVIITNVGGLILYLIIIGDVLSGKQNGGEVHLGILQQWFGIHWWNSR
EFALLFTLVFVMLPLVLYKRVESLKYSSAVSTLLAVAFVGICCGLAITAL
VQGKTQTPRLFPRLDYQTSFFDLFTAVPVVVTAFTFHFNVHPIGFELAKA
SQMTTAVRLALLLCAVIYLAIGLFGYMLFGDSTQSDILINFDQNAGSAVG
SLLNSLVRVSYALHIMLVFPLLNFSLRTNIDEVLFPKKPMLATDNKRFMI
LTLVLLVFSYLAAIAIPDIWYFFQFLGSSSAVCLAFIFPGSIVLRDVKGI
STRRDKIIALIMIILAVVTSVLAISTNIYNAFSSKS*

>Glyma18g02590.1|PACid: 16307712

(SEQ ID NO: 2)
MADQLSKGEEFEKKAEKKLSGWGLFGSKYEDAADLFDKAANCFKLAKSWD
KAGATYLKLASCHLKLESKHEAAQAHVDAAHCYKKTNINESVSCLDRAVN
LFCDIGRLSMAARYLKEIAELYEGEQNIEQALVYYEKSADFFQNEEVTTS
ANQCKQKVAQFAAQLEQYQKSIDIYEEIARQSLNNNLLKYGVKGHLLNAG
ICQLCKEDVVAITNALERYQELDPTFSGTREYRLLADIAAAIDEEDVAKF
TDVVKEFDSMTPLDSWKTTLLLRVKEKLKAKELEEDDLT*

>Glyma18g02610.1|PACid: 16307714

(SEQ ID NO: 3)
MRMLTGDSAADNSFRFVPQSIAAFGSTVIVEGCDSARNIAWVHAWTVTDG
MITQIREYFNTALTVTRIHDSGEIVPARSG

>Glyma18g02600.1|PACid: 16307713

(SEQ ID NO: 4)
MVSVDDGIVNPNDEIEKSNGSKVNEFASMDISATQKSYLNSEDPQRRLQG
TLISSSVTNRINFLKFGSASAKFKRLATERDQVSISVPSPRSKSLRSRFS
GMFAQKLDWASVKKMCMEWIRNPVNMALFVWIICVAVSGAILFLVMTGML
NGVLPRKSKRNAWFEVNNQILNAVFTLIPNDISSLRKVYCKNVTYKPHEW
THMMVVVILLHVNCFAQYALCGLNLGYKRSERPAIGVGICISFAIAGLYT
ILSPLGKDYDCEMDEEAQVQITASQGKEQLREKPTEKKYSFASKDQQRVV
ENRPKWSGGILDIWNDISLAYLSLFCTFCVLGWNMKRLGFGNMYVHIAIF
MLFCMAPFWIFLLASVNIDDDNVRQALAAVGIILCFLGLLYGGFWRIQMR
KRFNLPAYDFCFGKPSASDCTLWLPCCWCSLAQEARTRNNYDLVEDKFSR
KETDTSDQPSISPLAREDVVSTRSGTSSPMGSTSNSSPYMMKTSSSPNSS
NVLKGYYSPDKMLSTLNEDNCERGQDGTMNPLYAQK*

Quantitative Real Time PCR

Quantitative PCR (qPCR) was performed using either the MyIQ or CFX96 real-time PCR detection system (BioRad, Hercules, Calif.). cDNA was synthesized from RNA using iScript cDNA synthesis kit (Biorad, Hercules, Calif.) per manufactures protocol by adding 0.825 ug to 1.0 ug of RNA depending on the experiment. Total RNA was extracted from root tissue of conventional and transgenic soybeans. RNA was extracted from conventional soybean plants grown in Metro mix for two weeks at 26° C. and 16 hours light prior to tissue collection. Roughly 200 mg of tissue was collected from each plant, immediately flash-frozen in liquid nitrogen and stored at −80 C. Transgenic root material was collected from roots actively growing on HRM as previously described. Roughly 50-100 mg of tissue was collected from each root, flash frozen in liquid nitrogen and stored at −80 C. RNA was extracted using either the RNeasy Mini Kit (Qiagen, Valencia, Calif.) or TRIzol reagent (Life Technologies Corp., Carlsbad, Calif.) following manufactures protocols. RNA concentrations were determined using the Nano-Drop-1000 spectophotomoter (Thermo Scientific, Waltham, Mass.). DNA was removed from RNA samples using either RNase-free DNase I (Qiagen, Valencia, Calif.) or DNA-free (Life Technologies Corp., Carlsbad, Calif.) following manufacture protocols. RNA integrity was determined using the 2100 BioAnlyzer (Agilent Technologies, Santa Clara, Calif.) or 500 ng of total RNA was run on a 1.2% agarose gel stained with ethidium bromide and visualized under UV-light to ensure RNA quality following extraction. qPCR reactions were carried out using either IQ SYBR Green Supermix or SsoFast EvaGreen Supermix (Biorad, Hercules, Calif.). Primer concentrations for all reactions were between 0.2 μM and 0.3 μM. Two technical replicates were run per RNA. Efficiency curves were generated for qPCR primer pairs using cDNA from the cultivar Fayette or Williams 82 following a 3-4 step, 3-5 fold dilution. Following amplification, a melt curve program was performed. To ensure qPCR fluorescent signal was not the results of DNA, 100 ng of RNA extraction was added directly to IQ SYBR Green Supermix or SsoFast EvaGreen Supermix with primers. DNA contamination was considered negligible if CT values were not detected until after 32-35 cycles. A control reaction was run in parallel using a known cDNA sample. Transcript abundance for genes at Rhg1 was measured using primers X-X. A total of six primer pairs were tested as reference genes (EF1B, SKIP16, UNK2, ACT11, UNK1, TIP41) (Table 4 39-50). Hu, R. B., C. M. Fan, H. Y. Li, Q. Z. Zhang, and Y. F. Fu, Evaluation of putative reference genes for gene expression normalization in soybean by quantitative real-time RT-PCR. Bmc Molecular Biology, 2009. 10: p. 12. Reference genes were validated using Bestkeeper analysis. Pfaffl, M. W., A. Tichopad, C. Prgomet, and T. P. Neuvians, Determination of stable housekeeping genes, differentially regulated target genes and sample integrity: BestKeeper—Excel-based tool using pair-wise correlations. Biotechnology Letters, 2004. 26(6): p. 509-515. Primer pairs SKP16 and TIP41 were selected and used in subsequent experiments. Transgenic roots expressing empty-vector constructs analogous to the vectors carrying gene silencing or gene expression constructs were included in the experiments as controls and used to standardize gene expression. Results were considered to be at the limits of detection if CT values were >35 (i.e., for Glyma18g02600 transcripts).

DNA Repeat Junction Analysis

The presence of a repeat junction was confirmed using PCR (Table 4 81, 82) and soybean genomic DNA from SCN resistant cultivars Fayette, Hartwig, Newton and SCN susceptible cultivars Williams 82, Essex, Thorne and Sturdy. DNA extraction and PCR were performed as previously described. Possible impacts of retrotransposons on Rhg1 locus evolution were investigated by searching for sequences with similarity to known plant retrotransposons. A 185 bp sequence with 75% identity to the 5' and 3' tong terminal repeat (LTR) regions of Ty1/copia-like retrotransposons RTvr1 and RTvr2 is present within 400 bp of the rhg1-b duplication junction.

Statistical Analysis

Data were analyzed by ANOVA using Minitab (v.14) with the General Linear Model and Tukey Simultaneous Test.

Fosmid Library Construction

Seed of soybean Plant Introduction (PI) 88788 was obtained from the USDA soybean germplasm collection. Plants were grown in a growth chamber set at a photocyle of 18/6 hr (day/night), 23/20° C. (day/night), and 50% relative humidity for 1-2 weeks. Young leaf tissue was collected from six to 15 individuals for each line. Genomic DNA was extracted using cetrimonium bromide (CTAB). Plant samples were ground to fine powder in liquid nitrogen, transferred to 20 ml of CTAB extraction buffer (2% CTAB, 100 mM 8 Tris pH 9.5, 1.4 M NaCl, 1% PEG 6000, 20 mM EDTA, 2% polyvinylpyrrolidone, 2.5% β-mercaptoethanol), and placed at 65° C. for 1 hr. After incubation, an equal volume of Phenol:Chloroform:Isoamyl Alcohol (25:24:1, pH 6.7) was added to the tube, then centrifuged at 8,000 g at 10° C. for 10 min. The aqueous (top) phase was transferred to a new tube and an equal volume of chloroform:isoamyl alcohol (24:1) was added to the aqueous phase and centrifuged. The aqueous (top) phase was then transferred to a new tube and 0.7 volumes of isopropyl alcohol was added to the aqueous phase. After mixing well, the aqueous phase was centrifuged and the pellet resuspended in 70% EtOH, centrifuged at 7,500 g for 10 min. After centrifugation, the pellet was resuspended in 100 ul of TE (10 mM Tris pH 7.5, 1 mM EDTA). The DNA was treated with RNase A by incubating in 20 ug/ml RNase A at 37° C. for 1 hr. The PI 88788 fosmid library was constructed using the CopyControl™ Fosmid Library Production Kit (Epicentre, Madison, Wis.) following the manufacturer's protocol. Briefly, 20 ug of the size-fractionated DNA was used for end-repair. 35-45 kb fragment pools of DNA were cloned in the pCC1FOS™ Vector. Ligated DNA was packaged using the MaxPlax™ Lambda Packaging Extracts and transformed into the Phage T1-Resistant EPI 300™-T1® *E. coli* strain.

Fosmid Clone Sequencing and Assembly

Five candidate fosmid clones were identified by PCR-based pool screening using primers based on the rhg1-b interval of the Williams 82 reference sequence. Once it was confirmed that end sequences matched the anticipated region of the reference soybean genome sequence, they were sequenced using both the Roche 454/GS FLX+ system (Roche) and Illumina MiSeq (Illumina). 1-3 ug of fosmid clone DNA was used for making paired-end sequencing libraries for 454/GS FLX+. After library construction, pooled barcoded libraries were loaded onto one lane of the sequencing flow cell and sequenced. The average read length was 463 bp. The number of reads generated from 454/GS FLX+ is as follows: fosmid clone #1 in FIG. 2A: 10,865, #2: 6,271, #3: 6,648, #4: 6,520, and #5: 9,390. The reads were assembled using Phrap/Cross_match and CAP3. Huang, G. Z., R. Allen, E. L. Davis, T. J. Baum, and R. S. Hussey, Engineering broad root-knot resistance in transgenic plants by RNAi silencing of a conserved and essential root-knot nematode parasitism gene. Proceedings of the National Academy of Sciences of the United States of America, 2006. 103(39): p. 14302-14306. For the MiSeq, 0.3-2 ug of DNA was used for making the sequencing library. Average DNA fragment size was 550 bp (range from 430 to 720 bp). 154 cycles from each end of the fragments were performed using a TruSeq SBS sequencing kit version 1 and analyzed with Casaval 0.8 (pipeline 1.8). Throughout the reads, the average quality scores for each base were over 30. The number of reads generated from MiSeq is as follows: fosmid clone #1 in FIG. 2A: 1,067,403, #2: 814,728, #3: 1,156,784, #4: 1,091,852, and #5: 946,028. ABySS was used to assemble the reads from MiSeq. Simpson, J. T., K. Wong, S. D. Jackman, J. E. Schein, S. J. M. Jones, and I. Birol, ABySS: A parallel assembler for short read sequence data. Genome Research, 2009. 19(6): p. 1117-1123. The result was visualized using Geneious. Homopolymeric sequences and other problematic regions were manually sequenced using Sanger primer walking.

Whole-Genome Shotgun Sequencing and Read Depth in Duplicated Region

Whole-genome shotgun sequencing of a soybean breeding line LD09-15087a, a near-isogenic line (NIL) that harbors rhg1-b from PI 88788, was conducted using Illumina technology. 1.5 ug of genomic DNA was sequenced using the Illumina HiSeq 2000 instrument with 100 bp paired-end sequencing at the University of Illinois Biotechnology Center. The DNA fragment size for the soybean whole-genome shotgun sequencing library was 600 bp; the library was loaded onto one lane of a flow cell and sequenced using version 3 of sequencing kits and Casava 1.8 (pipeline 1.9). 312,909,668 reads (about 28× coverage of the 1.1 gb soybean genome) were generated with all positions having average quality scores 30 or higher. To examine the depth of the coverage within the duplicated region, reads from the sequencing were aligned to the Glyma1 version of the soybean genome assembly. Novoalign (v 2.08.01) with paired end options (PE 600,120) was used to align the reads to the reference genome. Approximately 95.1% of reads were aligned to the reference sequence. The number of reads aligned to the target interval was counted from a BAM file using SAMtools (v 0.1.18). Target interval is as follows: "Block" in FIG. 5B: a 31.2 kb region (1,632,225-1,663,455 on chromosome 18), "Block−1": the same size region as region of interest upstream, and "Block+1": the same size region as region of interest downstream. Homeologous regions on chromosome 11 ("Block" in FIG. 5B: 37,392,345-37,434,356 bp) and 2 ("Block": 47,772,323-47,791,521 bp) were identified using BLASTN. Analogous approaches were used with the soybean NAM parent sequence data.

Fiber-FISH

Soybean nuclei were lysed to release large chromosomal segments and, in contrast to more standard FISH methods, the chromosome segments were decondensed to generate extended DNA fibers before fixing to microscope slides and hybridizing to fluorescently labeled DNA probes. Young leaf tissues were collected from fast growing plants of Williams 82, Peking, and Fayette. Nuclei isolation, DNA fiber preparation, and fiber-FISH were performed following published protocols. Jackson, S. A., M. L. Wang, H. M. Goodman, and J. Jiang, Application of fiber-FISH in physical mapping of *Arabidopsis thaliana*. Genome, 1998. 41(4): p. 566-72. A fosmid clone spanning an rhg1-b repeat from PI 88788 was digested using the exonuclease SmaI (New England Biolabs, Ipswich, Mass.). The products of the restriction digestion were separated in a 0.7% get and isolated using the Qiaex II gel extraction kit (Qiagen, Valencia, Calif.), DNA probes were labeled with either biotin-1641717P or digoxigenin-11-dUTP (Roche Diagnostics, Indianapolis, Ind.) using a standard nick translation reaction. The fiber-FISH images were processed with Meta Imaging Series 7.5 software. The final contrast of the images was processed using Adobe Photoshop CS3 software. The cytological measurements of the fiber-FISH signals were converted into kilobases using a 3.21 kb/μm conversion rate.

Transcript Analysis

To confirm the annotation of transcripts at Rhg1, rapid amplification of cDNA ends (RACE) PCR was performed for Glyma18g02580 (Table 4 95), Glyma18g02590 (Table 4 87-90) and Glyma18g02610 (Table 4 91-94) using the SMARTer RACE cDNA kit per manufacturer protocols (ClonTech, Mountain View, Calif.). Following RACE, PCR products were TA cloned into pCR8/GW/TOPO as previously mentioned. Randomly chosen colonies were sequenced (Table 4 76, 77) as described to confirm the 5' and 3' ends of individual transcripts. To detect potential transcript isoforms, northern analysis was conducted using standard methods. Probes were generated for Glyma18g02570 (Table 4 83, 84). Absence of truncated Glyma18g02570 transcripts (Table 4 85, 86) derived from 31.2 kb repeat junctions was also confirmed by PCR from cDNA, using a 2570 reverse primer and a forward primer in the most strongly predicted exon upstream of the repeat junction. Hebsgaard, S. M., P. G. Korning, N. Tolstrup, J. Engelbrecht, P, Rouze, and S. Brunak, Splice site prediction in *Arabidopsis thaliana* pre-mRNA by combining local and global sequence information. Nucleic Acids Research, 1996. 24(17): p. 3439-3452. Transcript abundance studies using qPCR also indicated that there is not a Glyma18g02570-like transcript produced by the repeated DNA insertion. Glyma18g02570 transcript abundance was measured using primers (Table 4 25, 26) that amplify the final two exons and hence should amplify both the reference genome (full-length; Williams 82-like) Glyma18g02570 transcript and possible hybrid Glyma18g02570 transcripts that are transcribed from DNA that spans the repeat junction. If the repeated DNA produced an alternative transcript, these primers would amplify additional product from genotypes with the repeat. However, no differences in transcript abundance were detected between SCN-resistant vs SCN-susceptible varieties using Glyma18g02570 primers 25 and 26.

Protein Structure Prediction and Comparison

The protein structure for the predicted Glyma18g02610 gene product was modeled and proteins with the most homologous structures were identified using Phyre2, with default settings. Kelley, L. A. and M. J. E. Sternberg, Protein structure prediction on the Web: a case study using the Phyre server. Nature Protocols, 2009. 4(3): p. 363-371.

Methylation Analysis

Figure 11A:
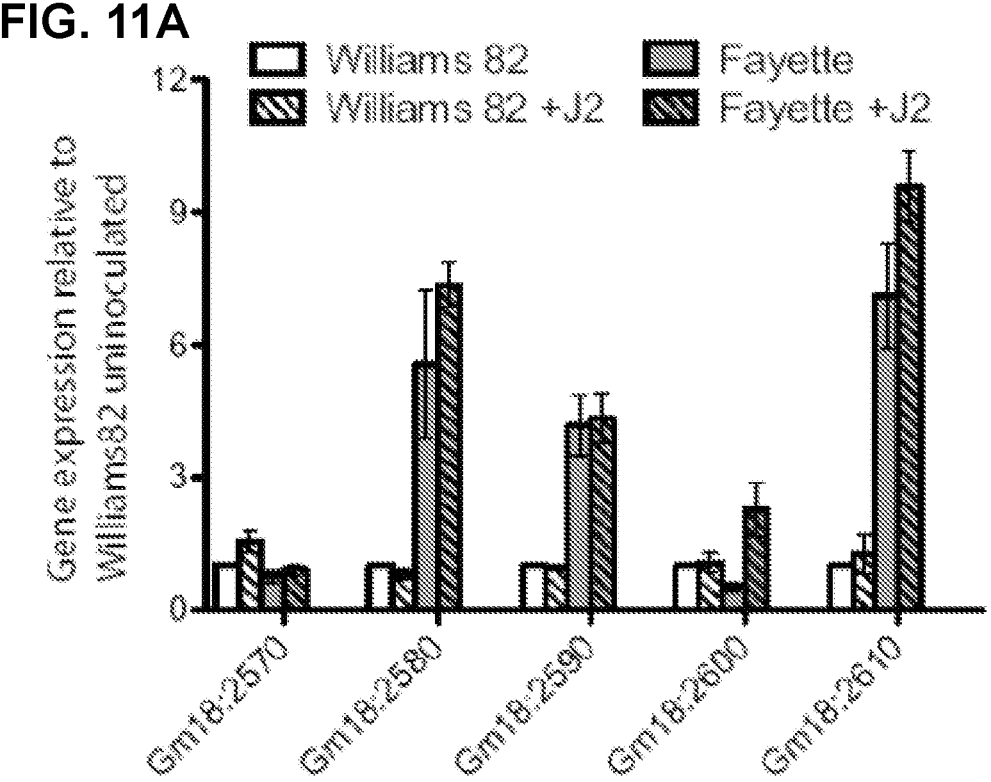
FIG. 11A is a graph showing the quantitative PCR gene expression analysis for genes at the Rhg1 locus in susceptible and resistant roots showing that some of these genes not only are more highly expressed in resistant cultivars (as is also shown in FIG. 11), but also exhibit some upregulation after inoculation with SCN.
Figure 11B:
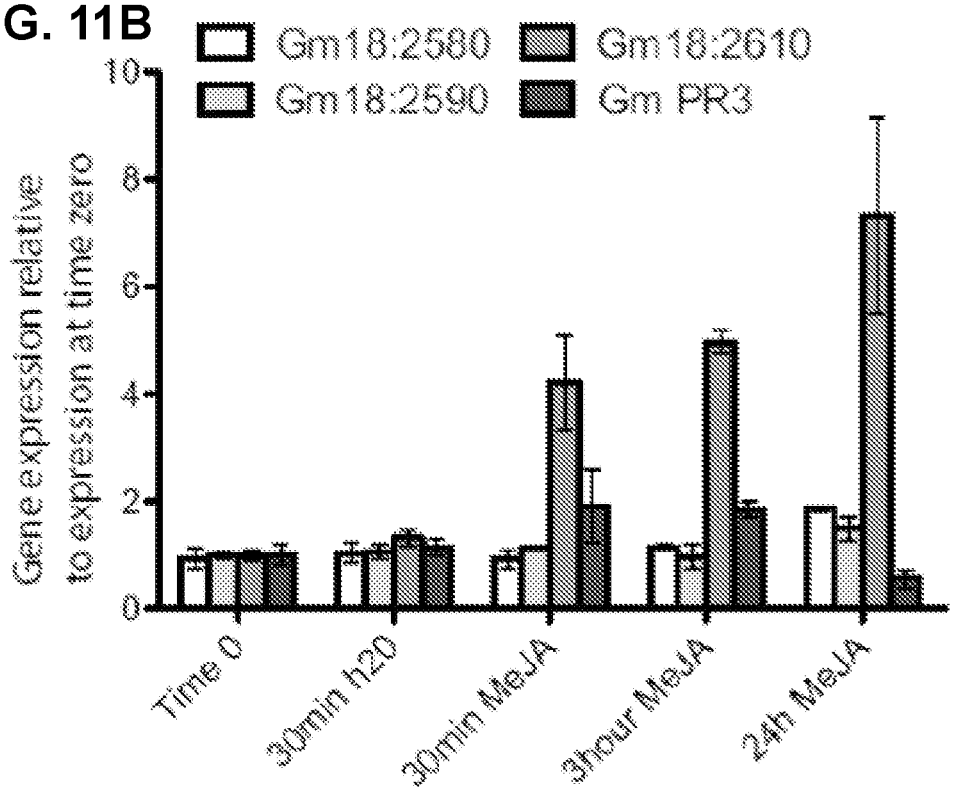
FIG. 11B is a graph showing the quantitative PCR gene expression analysis following methyl jasmonate or water treatment, which reveals that Glyma18g02610 is expressed more highly in response to elevated levels of methyl jasmonate.

Locus specific DNA methylation was analyzed using the methylation specific endonulease McrBC, or the methylation sensitive endonuclease HpaII followed by PCR. (FIGS. 11A-11C.) McrBC (New England Biolabs, Ipswich, Mass.) digests DNA with methylated cytosines in a sequence-independent manner while unmethylated DNA is not digested. HpaII (New England Biolabs, Ipswich, Mass.) digests DNA at the recognition sequence CCGG, but HpaII endonuclese activity is blocked by cytosine methylation. Restriction digestions were performed using 600-700 ng of DNA and manufacturer's protocols. Control reactions were set up by adding the same amount of DNA to the reaction buffer with no restriction enzyme. Samples with and without the restriction enzyme were incubated at 37° C. for 90 minutes, and heat inactivated at 65° C. for 20 minutes. DNA was visualized in a 0.8% ethidium bromide stained gel to ensure DNA digestion. Both digested and control DNA samples were used for subsequent PCR using GoTaq Flexi DNA polymerase (Promega, Madison Wis.). For DNA treated with McrBC, PCR primers that spanned methylated DNA would not produce the intended product following PCR because the template DNA would be digested by McrBC. DNA that was not methylated or not treated with the enzyme yielded a product of the expected size. For DNA treated with HpaII, PCR primers that spanned the DNA sequence CCGG in which either cytosine was methylated yielded a PCR product of the expected size. DNA sequence CCGG that was not methylated was cleaved by HpaII and failed to yield a PCR product. DNA incubated in buffer without HpaII yielded expected PCR products.

Western Blot Analysis

Protein size and abundance were measured using Western blot and immunodetection procedures (Ausubel et al. 1997). Briefly, protein was extracted from roots of transgenic soybeans by homogenizing frozen root tissue and re-suspending the material in 2× Tricine sample buffer (0.1 M TrisCl/0.3% SDS pH6.8, 24% glycerol, 8% SDS, 0.2M DTT) at 1:1 w/v ratio. An equal volume of each protein sample was separated in a Tris-Tricine polyacrylamide gel (9.8% separation gel, 3.9% stacking gel) using electrophoresis in the Biorad Mini Protean3 cassette (Biorad, Hercules Calif.). The samples are separated at 35 volts for roughly one hour, followed by another hour at 160 volts. The gel was moved to a transfer cassette and aqueous transferred to a Protran nitrocellulose membrane (Whatman, Piscataway, N.J.). The transfer was run for an hour at 80 volts at room temperature. Following transfer, membranes were stained for total protein using 0.1% Ponceau S (Sigma-Aldrich, St. Louis, Mo.) in 5% acetic acid and imaged. Ponceau S was destained in ddH$_2$0, and the membrane was blocked over night at 4° C. in TBST (20 mM Tris pH7.5, 8 g/L NaCl, 0.1% Tween) carrying 5% milk. New 5% milk in TBST was added to the membrane and placed on shaker at room temperature for 30 minutes. The membrane was incubated with HA primary antibody directly conjugated to horse radish peroxidase (HRP) at a 1:1000 concentration in 5% milk TBST for 90 minutes. The membrane was washed 3× in TBST at room temperature on a shaker for 20 minutes each. Supersignal West Dura Extended Duration Substrate (Thermo Scientific, Waltham, Mass.) ECL kit was used following manuacture protocols to detect the HA-HRP antibody on the membrane. The memebrane was exposed to Cl-Xposure film (Thermo Scientific, Waltham, Mass.) and developed.

We claim:

1. A method of increasing resistance of plant cells to nematodes comprising:
introducing three or more copies of polynucleotides that encode
a polypeptide according to SEQ ID NO: 1, or a polypeptide with at least 98% identity to SEQ ID NO: 1,
a polypeptide according to SEQ ID NO: 2, SEQ ID NO: 5, or SEQ ID NO: 6, or a polypeptide with at least 95% identity to SEQ ID NO: 2, SEQ ID NO: 5, or SEQ ID NO: 2, and
a polypeptide according to SEQ ID NO: 3,
wherein said plant cells have increased resistance to nematodes relative to plant cells without increased copy number of said polynucleotides,
and wherein said plant cells are soybean, *Arabidopsis* or potato.

2. The method of claim 1, wherein four or more copies of polynucleotides encoding said polypeptides are introduced in the plant cells.

3. The method of claim 1, wherein at least ten copies of polynucleotides encoding said polypeptides are introduced in the plant cells.

4. The method of claim 1, wherein the plant cells comprise a plant, and wherein increased nematode resistance comprises the plant having one or more of:
(a) a lower percentage of invading nematodes that develop past the J2 stage,
(b) a lower rate of cyst formation on the roots,
(c) reduced nematode female index of a plant exposed to nematodes,
(d) reduced SCN egg production within cysts,
(e) reduced overall SCN egg production per plant, or
(f) greater yield of soybean seeds on a per-plant basis or a per-growing-area basis, as compared to a plant without increased copy number of said polynucleotides grown in a similar growth environment.

5. The method of claim 1, further comprising increasing expression of said polynucleotides in the plant cells,
wherein said plant cells have increased resistance to nematodes relative to plant cells without increased expression of said polynucleotides.

6. The method of claim 5, wherein expression of one or more polynucleotides is increased in plant cells in the root of the plant.

7. The method of claim 5, wherein expression of one or more polypeptides is increased by increasing expression of one or more native polynucleotides.

8. The method of claim 5, wherein expression of said polypeptides is increased by introducing a construct comprising a promoter operably linked to a polynucleotide encoding the polypeptide into the plant cells.

9. The method of claim 5, wherein expression of said polypeptides are increased by incorporation of a construct comprising a promoter operably linked to a polynucleotide encoding one of said polypeptides in the plant cells.

10. The method of claim 5 wherein the plant cell exhibits increased expression of each of
a polypeptide according to SEQ ID NO: 1,
a polypeptide according to SEQ ID NO: 2, SEQ ID NO: 5, or SEQ ID NO: 6, and
a polypeptide according to SEQ ID NO: 3.

11. A transgenic plant cell comprising:
three or more copies of polynucleotides encoding polypeptides capable of increasing resistance to nematodes, the polypeptides comprising:
a polypeptide according to SEQ ID NO: 1, or a polypeptide with at least 98% identity to SEQ ID NO: 1,
a polypeptide according to SEQ ID NO: 2, SEQ ID NO: 5, or SEQ ID NO: 6, or a polypeptide with at least 95% identity to SEQ ID NO: 2, SEQ ID NO: 5, or SEQ ID NO: 2, and a polypeptide according to SEQ ID NO: 3,
wherein said plant cell has increased resistance to nematodes relative to plant cells
without increased copy number of said polynucleotides, and wherein said plant cells are soybean, *Arabidopsis* or potato.

12. The transgenic cell of claim 11, wherein the polynucleotides are present in at least four copies in the cell.

13. The transgenic cell of claim 11, wherein the polynucleotides are present in at least ten copies in the cell.

14. A seed comprising the transgenic cell of claim 11.

15. A plant grown from the seed of claim 14.

16. A transgenic plant comprising the cell of claim 11.

17. A part, progeny or asexual propagate of the transgenic plant of claim 16.

18. The transgenic plant cell of claim 11, further comprising increasing expression of the polynucleotides encoding said polypeptides capable of increasing resistance to nematodes,
wherein said plant cells have increased resistance to nematodes relative to plant cells without increased expression of said polynucleotides.

19. The transgenic plant cell of claim 18, wherein the polynucleotides encode at least
a polypeptide according to SEQ ID NO: 1,
a polypeptide according to SEQ ID NO: 2, SEQ ID NO: 5, or SEQ ID NO: 6, and
a polypeptide according to SEQ ID NO: 3.

20. A method of generating a transgenic plant with increased resistance to nematodes comprising introducing into a plant cell or its progeny three or more copies of exogenous polynucleotides encoding one or more polypeptides capable of increasing resistance to nematodes, the polypeptides comprising:
a Glyma18g02580 polypeptide having at least 98% identity to SEQ ID NO: 1,
a Glyma18g02590 polypeptide having at least 95%; identity to SEQ ID NO: 2, 5 or 6, and
a Glyma18g02610 polypeptide according to SEQ ID NO: 3, wherein said plant has increased resistance to nematodes relative to a plant without increased copy number of said polynucleotides, and wherein said plant is soybean, *Arabidopsis* or potato.

21. The method of claim 20, wherein the polynucleotides are present in at least four copies in the plant.

22. The method of claim 20, further comprising increasing expression of the polynucleotides encoding polypeptides capable of increasing resistance to nematodes,
wherein said plant has increased resistance to nematodes relative to a plant without increased expression of said polynucleotides.

23. The method of claim 22, wherein the polynucleotides encode at least a Glyma18g02610 polypeptide according to SEQ ID NO:3, a Glyma18g02590 polypeptide according to SEQ ID NO:2, 5 or 6 and a Glyma18g02580 polypeptide according to SEQ ID NO:1.

* * * * *